(12) United States Patent
Brandl et al.

(10) Patent No.: US 8,354,418 B2
(45) Date of Patent: *Jan. 15, 2013

(54) THIAZOLYL-DIHYDRO-QUINAZOLINES

(75) Inventors: Trixi Brandl, Basel (CH); Udo Maier, Senden (DE); Christoph Hoenke, Ingelheim (DE); Anne T. Joergensen, Copenhagen (DK); Alexander Pautsch, Ulm (DE); Steffen Breitfelder, Attenweiler (DE); Matthias Grauert, Biberach (DE); Matthias Hoffmann, Mittelbiberach (DE); Stefan Scheuerer, Warthausen (DE); Klaus Erb, Mittelbiberach (DE); Michael Pieper, Biberach (DE); Ingo Pragst, Marburg (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 538 days.

This patent is subject to a terminal disclaimer.

(21) Appl. No.: 12/351,017

(22) Filed: Jan. 9, 2009

(65) Prior Publication Data
US 2009/0131424 A1     May 21, 2009

Related U.S. Application Data

(63) Continuation of application No. 11/690,355, filed on Mar. 23, 2007, now abandoned.

(30) Foreign Application Priority Data

Apr. 6, 2006 (EP) .................................. 06112296

(51) Int. Cl.
C07D 239/00 (2006.01)
A01N 43/54 (2006.01)
A61K 31/505 (2006.01)

(52) U.S. Cl. ........................................ 514/267; 544/250
(58) Field of Classification Search .................. 514/267; 544/250
See application file for complete search history.

(56) References Cited

U.S. PATENT DOCUMENTS

| | | | |
|---|---|---|---|
| 4,380,640 A | 4/1983 | Brunner et al. | |
| 7,517,995 B2 | 4/2009 | Breitfelder et al. | |
| 7,691,868 B2 * | 4/2010 | Brandl et al. .................. | 514/267 |
| 7,691,888 B2 | 4/2010 | Betzemeier et al. | |
| 7,893,049 B2 | 2/2011 | McConnell et al. | |
| 7,902,183 B2 | 3/2011 | Steurer et al. | |
| 2002/0151544 A1 | 10/2002 | Hayakawa et al. | |
| 2006/0100254 A1 | 5/2006 | Betzemeier et al. | |
| 2006/0106013 A1 * | 5/2006 | Breitfelder et al. ......... | 514/232.5 |
| 2007/0238718 A1 | 10/2007 | Breitfelder et al. | |
| 2007/0238730 A1 | 10/2007 | Breitfelder et al. | |
| 2007/0259855 A1 | 11/2007 | Maier et al. | |
| 2007/0270401 A1 | 11/2007 | Steurer et al. | |
| 2008/0081802 A1 | 4/2008 | McConnell et al. | |
| 2009/0093474 A1 | 4/2009 | Grauert et al. | |
| 2009/0156554 A1 * | 6/2009 | Breitfelder et al. ............. | 514/63 |

FOREIGN PATENT DOCUMENTS

| WO | WO 57008 A1 | 8/2001 |
|---|---|---|
| WO | WO 072557 A1 | 4/2003 |
| WO | WO 007491 A1 | 1/2004 |
| WO | WO 029055 A1 | 4/2004 |
| WO | WO 052373 A1 | 6/2004 |
| WO | WO 056820 A1 | 7/2004 |
| WO | WO 005438 A1 | 1/2005 |
| WO | 2005/016245 A2 | 2/2005 |
| WO | 2005/037843 A1 | 4/2005 |
| WO | 2006/040281 A1 | 4/2006 |
| WO | WO 040279 A1 | 4/2006 |
| WO | 2007/113245 A1 | 10/2007 |
| WO | 2007/113246 A1 | 10/2007 |
| WO | 2007/115929 A1 | 10/2007 |
| WO | 2007/115930 A1 | 10/2007 |
| WO | 2007/115931 A1 | 10/2007 |
| WO | 2007/115933 A1 | 10/2007 |

OTHER PUBLICATIONS

EP Search Report dated Sep. 11, 2006.
G. Y. Oudit, et al., "Phosphoinositide 3-Kinase Y-Deficient Mice are Protected from Isoproterenol-Induced Heart Failure". Circulation, 2003, vol. 108, No. 17, p. 2147-2152.
B. Vanhaesebroeck, et al., "Synthesis and Function of 3-Phosphorylated Inositol Lipids", Annual Review of Biochemistry, 2001, vol. 70, p. 535-602.
S. Ward, et al., "Isoform-specific phosphoinositide 3-Kinase Inhibitors as Therapeutic Agents. Current Opinion in Pharmacology", 2003, vol. 3, p. 426-434.
A.R. West, et al., Solid State Chemistry and its Applications. Publisher John Wiley & Sons. Department of Chemistry, Undersity of Aberdeen, Mar. 3, 1988.

* cited by examiner

*Primary Examiner* — James O Wilson
*Assistant Examiner* — Erich A Leeser
(74) *Attorney, Agent, or Firm* — Michael P. Morris; Edward S. Lazer

(57) ABSTRACT

The present invention relates to compounds of general formula (I),

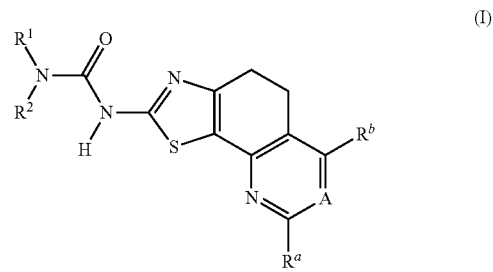

wherein the groups A, $R^1$, $R^2$, $R^a$ and $R^b$ have the meanings given in the claims and specification, the tautomers, racemates, enantiomers, diastereomers and the mixtures thereof, and optionally the pharmacologically acceptable acid addition salts, solvates and hydrates thereof, and processes for preparing these thiazolyl-dihydro-quinazolines and the use thereof as pharmaceutical compositions.

8 Claims, No Drawings

THIAZOLYL-DIHYDRO-QUINAZOLINES

This application is a continuation of U.S. application Ser. No. 11/690,355 filed Mar. 23, 2007 which claims priority benefit to EP 06112296, filed Apr. 6, 2006, the entirety of which is incorporated herein.

The present invention relates to new thiazolyl-dihydro-quinazolines of general formula (I)

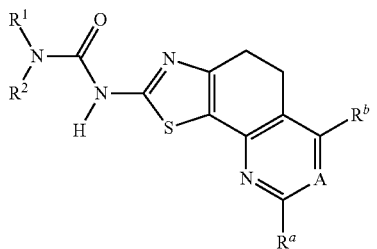

(I)

wherein the groups A, $R^1$, $R^2$, $R^a$ and $R^b$ have the meanings given in the claims and specification, the tautomers, racemates, enantiomers, diastereomers and the mixtures thereof, and optionally the pharmacologically acceptable acid addition salts, solvates and hydrates thereof, and processes for preparing these thiazolyl-dihydro-quinazolines and the use thereof as pharmaceutical compositions.

BACKGROUND TO THE INVENTION

Phosphatidylinositol-3-kinases (PI3-kinases) are a subfamily of the lipid kinases which catalyse the transfer of a phosphate group to the 3'-position of the inositol ring of phosphoinositides.

They have a role in numerous cell processes such as e.g. cell growth and differentiation processes, the control of cytoskeletal changes and the regulation of intracellular transport processes (Vanhaesebroeck et al., Annu Rev Biochem. 2001; 70:535-602).

PI3-kinases may play a part in numerous tumours, such as e.g. breast cancer, ovarian or pancreatic carcinoma, in tumour types such as carcinomas of the colon, breast or lungs, but particularly in autoimmune diseases such as Crohn's disease or rheumatoid arthritis, for example, or in the cardiovascular system, e.g. in the development of cardiac hypertrophy (Oudit et al., Circulation. 2003 Oct. 28; 108(17):2147-52). PI3-kinase modulators may represent a possible method of anti-inflammatory therapy with comparatively minor side effects (Ward and Finan, Curr Opin Pharmacol. 2003 August; 3(4): 426-34).

PI3-kinase inhibitors for treating inflammatory diseases are known in the literature. Thus, WO 03/072557 discloses 5-phenylthiazole derivatives, WO 04/029055 discloses annelated azolopyrimidines and WO 04/007491 discloses azolidinone-vinyl linked benzene derivatives. Moreover, the two specifications WO 04/052373 and WO 04/056820 disclose benzoxazine and benzoxazin-3-one derivatives.

The aim of the present invention is to provide new compounds which by virtue of their pharmaceutical activity as PI3-kinase modulators may be used therapeutically for the treatment of inflammatory or allergic diseases. Examples of these include inflammatory and allergic respiratory complaints, inflammatory and allergic skin complaints, inflammatory eye diseases, diseases of the nasal mucosa, inflammatory or allergic illnesses which involve autoimmune reactions or kidney inflammation.

DETAILED DESCRIPTION OF THE INVENTION

Surprisingly it has been found that the above problem is solved by means of compounds of formula (I), wherein A and the groups $R^1$, $R^2$, $R^a$ and $R^b$ have the meanings given hereinafter.

It has been found, in particular, that compounds of formula (I) act as inhibitors of PI3-kinase, particularly as inhibitors of PI3-kinase gamma. Thus the compounds according to the invention may be used for example for the treatment of respiratory complaints.

The present invention therefore relates to compounds of general formula (I),

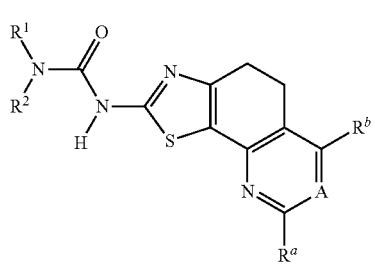

(I)

wherein
A denotes N or CH;
$R^a$ denotes hydrogen or an optionally substituted group selected from among $C_1$-$C_8$-alkyl, $C_2$-$C_8$-alkenyl, $C_2$-$C_8$-alkynyl, $C_3$-$C_8$-cycloalkyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_4$-alkyl, spiro, $C_3$-$C_8$-heterocycloalkyl and $C_3$-$C_8$-heterocycloalkyl-$C_1$-$C_4$-alkyl,
$R^b$ denotes hydrogen, OH or $NH_2$
or an optionally substituted group selected from among $C_1$-$C_8$-alkyl, $C_3$-$C_8$-cycloalkyl, $C_2$-$C_8$-alkenyl, $C_2$-$C_8$-alkynyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_4$-alkyl, spiro, $C_3$-$C_8$-heterocycloalkyl, $CONH_2$, $C_6$-$C_{14}$-aryl-NH, $C_3$-$C_8$-heterocycloalkyl-NH— and O—$C_1$-$C_3$-alkyl,
$R^1$ denotes hydrogen or an optionally substituted group selected from among $C_1$-$C_8$-alkyl, $C_3$-$C_8$-cycloalkyl, $C_2$-$C_8$-alkenyl, $C_2$-$C_8$-alkynyl and $C_6$-$C_{14}$-aryl-$C_1$-$C_5$-alkyl-;
or
$R^2$ denotes hydrogen or an optionally substituted group selected from among $C_1$-$C_8$-alkyl, $C_3$-$C_8$-cycloalkyl, $C_2$-$C_8$-alkenyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_6$-alkyl, $C_9$-$C_{13}$-spiro, $C_3$-$C_8$-heterocycloalkyl, $C_3$-$C_8$-heterocycloalkyl-$C_1$-$C_6$-alkyl- and $C_6$-$C_{14}$-aryl-$C_1$-$C_6$-alkyl-;
or
$R^1$ and $R^2$ together form an optionally substituted five-, six- or seven-membered ring consisting of carbon atoms and optionally 1 to 2 heteroatoms, selected from among oxygen, sulphur and nitrogen.

or

R$^1$ and R$^2$ together form an optionally substituted nine- to thirteen-membered spirocyclic ring, or R$^2$ denotes a group selected from among general formulae (A1) to (A18)

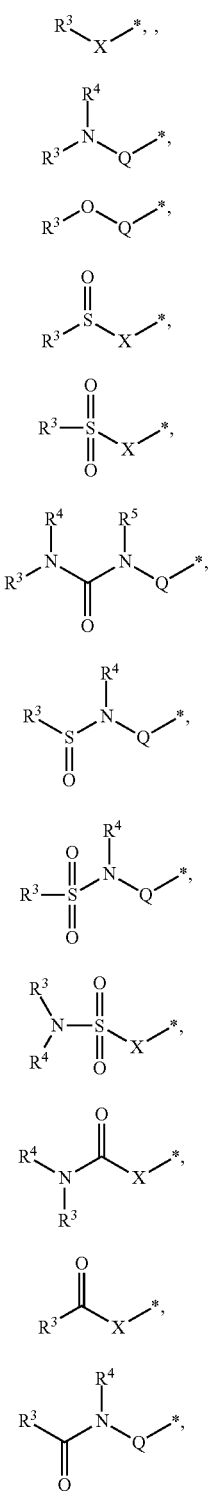

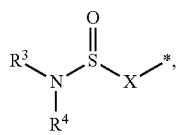

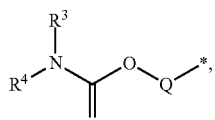

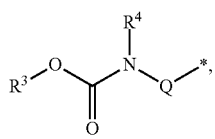

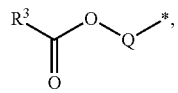

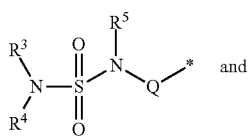

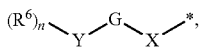

wherein

X and Y may be linked to the same or different atoms of G, and

X denotes a bond or an optionally substituted group selected from among C$_1$-C$_7$-alkylene, C$_3$-C$_7$-alkenylene and C$_3$-C$_7$-alkynylene, or X together with R$^1$, R$^3$ or R$^4$ may form a C$_1$-C$_7$-alkylene bridge;

Y denotes a bond or optionally substituted C$_1$-C$_4$-alkylene;

Q denotes an optionally substituted group selected from among C$_1$-C$_7$-alkylene, C$_3$-C$_7$-alkenylene and C$_3$-C$_7$-alkynylene, or Q together with R$^1$, R$^3$ or R$^4$ may form a C$_1$-C$_7$-alkylene bridge;

R$^3$, R$^4$, R$^5$ which may be identical or different, denote hydrogen or an optionally substituted group selected from among C$_1$-C$_8$-alkyl, C$_3$-C$_8$-cycloalkyl, C$_2$-C$_6$-haloalkyl, C$_1$-C$_4$-alkyl-C$_3$-C$_8$-cycloalkyl, C$_3$-C$_8$-cycloalkyl-C$_1$-C$_4$-alkyl, NR$^7$R$^8$, NR$^7$R$^8$—C$_1$-C$_4$-alkyl, C$_1$-C$_4$-alkoxy, C$_1$-C$_4$-alkoxy-C$_1$-C$_4$-alkyl, C$_6$-C$_{14}$-aryl and C$_5$-C$_{10}$-heteroaryl;

or in each case two of the substituents

R$^3$, R$^4$, R$^5$ together form an optionally substituted five-, six- or seven-membered ring, consisting of carbon atoms and optionally 1-2 heteroatoms, selected from among oxygen, sulphur and nitrogen;

G denotes a saturated, partially saturated or unsaturated ring system consisting of 3-10 C atoms, wherein optionally up to 6 C atoms are replaced by heteroatoms selected from among nitrogen, oxygen and sulphur;

R$^6$ which may be identical or different, denote hydrogen or an optionally substituted group selected from among =O, C$_1$-C$_8$-alkyl, C$_2$-C$_6$-alkenyl C$_3$-C$_8$-cycloalkyl, C$_2$-C$_6$-haloalkyl, C$_6$-C$_{14}$-aryl, C$_5$-C$_{10}$-heteroaryl and C$_3$-C$_8$-heterocycloalkyl, or
a group selected from among NR⁷R⁸, OR⁷, —CO—C₁-C₃-alkyl-NR⁷R⁸, —O—C₁-C₃-alkyl-NR⁷R⁸, CONR⁷R⁸, NR⁷COR⁸, —CO—C₁-C₃-alkyl-NR⁷(CO)OR⁸, —O(CO)NR⁷R⁸, NR⁷(CO)NR⁸R⁹, NR⁷(CO)OR⁸, (CO)OR⁷, —O(CO)R⁷, COR⁷, (SO)R⁷, (SO₂)R⁷, (SO₂)NR⁷R⁸, NR⁷(SO₂)R⁸, NR⁷(SO₂)NR⁸R⁹, CN, —C₁-C₃-alkyl-C₆-C₁₄-aryl, —NH—CO—NH—C₁-C₃-alkyl and halogen;

n denotes 1, 2 or 3

R⁷, R⁸, R⁹ which may be identical or different, denote hydrogen or an optionally substituted group selected from among C₁-C₈-alkyl, C₃-C₈-cycloalkyl, C₁-C₆-haloalkyl, C₁-C₄-alkyl-C₃-C₈-cycloalkyl, C₃-C₈-cycloalkyl-C₁-C₃-alkyl, C₆-C₁₄-aryl, C₁-C₄-alkyl-C₆-C₁₄-aryl, C₆-C₁₄-aryl-C₁-C₄-alkyl, C₃-C₈-heterocycloalkyl, C₁-C₅-alkyl-C₃-C₈-heterocycloalkyl, C₃-C₈-heterocycloalkyl-C₁-C₄-alkyl, C₁-C₄-alkyl(CO)— and C₁-C₄-alkyl-O(CO)—;

or in each case two of the substituents

R⁷, R⁸, R⁹ together form an optionally substituted five-, six- or seven-membered ring, consisting of carbon atoms and optionally 1-2 heteroatoms, selected from among oxygen, sulphur and nitrogen;

optionally in the form of the tautomers, the racemates, the enantiomers, the diastereomers and the mixtures thereof, as well as optionally the pharmacologically acceptable acid addition salts, solvates and hydrates thereof, with the proviso that the following compounds are excluded:

a) 8-phenyl-4,5-dihydro-thiazolo[4,5-h]quinazolin-2-yl)-urea
b) 1-methyl-3-(8-phenyl-4,5-dihydro-thiazolo[4,5-h]quinazolin-2-yl)-urea
c) 1,1-dimethyl-3-(8-phenyl-4,5-dihydro-thiazolo[4,5-h]quinazolin-2-yl)-urea
d) 1-(2-dimethylamino-ethyl)-3-(8-phenyl-4,5-dihydro-thiazolo[4,5-h]quinazolin-2-yl)-urea
e) 4-methyl-piperazine-1-carboxylic acid (8-phenyl-4,5-dihydro-thiazolo[4,5-h]quinazolin-2-yl)-amide
f) piperidine-1-carboxylic acid (8-phenyl-4,5-dihydro-thiazolo[4,5-h]quinazolin-2-yl)-amide
g) pyrrolidine-1-carboxylic acid (8-phenyl-4,5-dihydro-thiazolo[4,5-h]quinazolin-2-yl)-amide
h) 1-methyl-3-(8-o-tolyl-4,5-dihydro-thiazolo[4,5-h]quinazolin-2-yl)-urea
i) (8-o-tolyl-4,5-dihydro-thiazolo[4,5-h]quinazolin-2-yl)-urea
j) 1,1-dimethyl-3-(8-o-tolyl-4,5-dihydro-thiazolo[4,5-h]quinazolin-2-yl)-urea and
k) [8-(2-methoxy-phenyl)-4,5-dihydro-thiazolo[4,5-h]quinazolin-2-yl]-urea and
l) morpholine-4-carboxylic acid (8-phenyl-4,5-dihydro-thiazolo[4,5-h]quinazolin-2-yl)-amide.

Preferred are compounds of formula (I), wherein
X, Y, Q and G may have the meaning specified and
A denotes N,
Rᵃ denotes hydrogen or a group selected from among C₁-C₈-alkyl, C₂-C₈-alkenyl, C₂-C₈-alkynyl, C₃-C₈-cycloalkyl, C₃-C₈-cycloalkenyl, C₁-C₆-haloalkyl, C₆-C₁₄-aryl, C₆-C₁₄-aryl-C₁-C₅-alkyl, C₅-C₁₀-heteroaryl, C₃-C₈-cycloalkyl-C₁-C₄-alkyl, C₃-C₈-cycloalkenyl-C₁-C₄-alkyl, C₅-C₁₀-heteroaryl-C₁-C₄-alkyl, spiro, C₃-C₈-heterocycloalkyl and C₃-C₈-heterocycloalkyl-C₁-C₄-alkyl, which may optionally be substituted by one or more of the groups, which may be identical or different, selected from among C₁-C₆-alkyl, C₂-C₆-alkenyl, C₂-C₆-alkynyl, C₂-C₆-alkynyl-NR⁵R⁶, C₃-C₈-cycloalkyl, C₁-C₆-haloalkyl, halogen, OH, C₁-C₄-alkoxy, CN, NO₂, NR¹⁰R¹¹, OR¹⁰, COR¹⁰, COOR¹⁰, CONR¹⁰R¹¹, NR¹⁰COR¹¹, NR¹⁰(CO)NR¹¹R¹², O(CO)NR¹⁰R¹¹, NR¹⁰(CO)OR¹¹, SO₂R¹⁰, SOR¹⁰, SO₂NR¹⁰R¹¹, NR¹⁰SO₂NR¹¹R¹² and NR¹⁰SO₂R¹¹;

or Rᵃ is optionally substituted by a group of general formula (B)

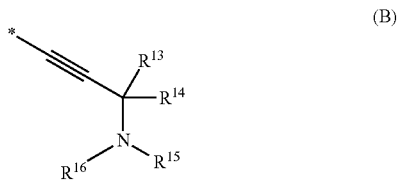

(B)

wherein,
R¹³ to R¹⁶ which may be identical or different, represent hydrogen or C₁-C₆-alkyl,
or two of the substituents
R¹³ to R¹⁶ together form an optionally substituted five-, six- or seven-membered ring, consisting of carbon atoms and optionally 1-2 heteroatoms, selected from among oxygen, sulphur and nitrogen;

R¹⁰, R¹¹, R¹² which may be identical or different, denote hydrogen or a group selected from among
C₁-C₆-alkyl, C₂-C₆-alkenyl, C₂-C₆-alkynyl, C₃-C₈-cycloalkyl and C₁-C₆ haloalkyl;
or
in each case two of the groups
R¹⁰, R¹¹, R¹² together form a five-, six- or seven-membered ring, consisting of carbon atoms and optionally 1-2 heteroatoms, selected from among oxygen, sulphur and nitrogen;

Rᵇ denotes hydrogen, OH or NH₂
or an optionally substituted group selected from among C₁-C₈-alkyl, C₃-C₈-cycloalkyl, C₂-C₈-alkenyl, C₂-C₈-alkynyl, C₃-C₈-cycloalkenyl, C₁-C₆-haloalkyl, C₆-C₁₄-aryl, C₆-C₁₄-aryl-C₁-C₅-alkyl, C₅-C₁₀-heteroaryl, C₃-C₈-cycloalkyl-C₁-C₄-alkyl, C₃-C₈-cycloalkenyl-C₁-C₄-alkyl, C₅-C₁₀-heteroaryl-C₁-C₄-alkyl, spiro, C₃-C₈-heterocycloalkyl, CONH₂, C₆-C₁₄-aryl-NH, C₃-C₈-heterocycloalkyl-NH— and O—C₁-C₃-alkyl,
which may optionally be substituted by one or more of the groups, which may be identical or different, selected from among
C₁-C₆-alkyl, C₂-C₆-alkenyl, C₂-C₆-alkynyl, C₃-C₈-cycloalkyl, C₁-C₆-haloalkyl, halogen, OH, OMe, CN, NH₂, NHMe and NMe₂;

R¹ denotes hydrogen or a group selected from among C₁-C₈-alkyl, C₃-C₈-cycloalkyl, C₂-C₈-alkenyl, C₂-C₈-alkynyl and C₆-C₁₄-aryl-C₁-C₅-alkyl, which may optionally be substituted by one or more of the groups, which may be identical or different, selected from among halogen, COOH, NH₂, OH, CN, C₁-C₆-alkyl, OMe, —NH(CO)-alkyl and —(CO)O-alkyl, R² denotes hydrogen or a group selected from among C₁-C₈ alkyl, C₃-C₈-cycloalkyl, C₂-C₈-alkenyl, C₃-C₈-cycloalkenyl, C₁-C₆-haloalkyl, C₆-C₁₄-aryl, C₆-C₁₄-aryl-C₁-C₅-alkyl, C₅-C₁₀-heteroaryl, C₃-C₈-cycloalkyl-C₁-C₄-alkyl, C₃-C₈-cycloalkenyl-C₁-C₄-alkyl, C₅-C₁₀-heteroaryl-C₁-C₆-alkyl, C₉-C₁₃-spiro, C₃-C₈-heterocycloalkyl, C₃-C₈-heterocycloalkyl-C₁-C₆-alkyl- and C₆-C₁₄-aryl-C₁-C₆- alkyl, which may optionally be substituted by one or more of the groups, which may be identical or different, selected from among halogen, NH$_2$, OH, CN, C$_1$-C$_6$-alkyl, OMe, —NH(CO)-alkyl, =O, COOH and —(CO)O-alkyl.
or R$^1$ and R$^2$ together form a five-, six- or seven-membered ring consisting of carbon atoms and optionally 1 to 2 heteroatoms, selected from among oxygen, sulphur and nitrogen, which may optionally be substituted by one or more of the groups, which may be identical or different, selected from among halogen, NH$_2$, OH, CN, C$_1$-C$_6$-alkyl, OMe, —NH(CO)—C$_1$-C$_4$-alkyl, and —(CO)O—C$_1$-C$_4$-alkyl.
or R$^1$ and R$^2$ together form an optionally substituted nine- to thirteen-membered spirocyclic ring,
or R$^2$ denotes a group selected from among general formulae (A1) to (A18)

(A1)

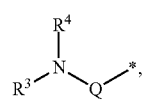
(A2)

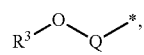
(A3)

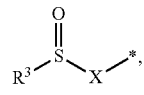
(A4)

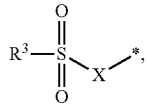
(A5)

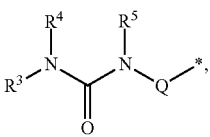
(A6)

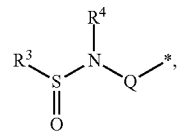
(A7)

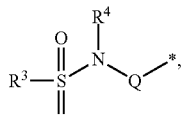
(A8)

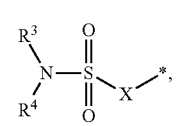
(A9)

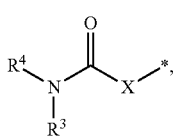
(A10)

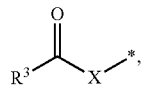
(A11)

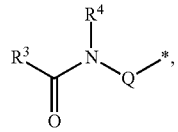
(A12)

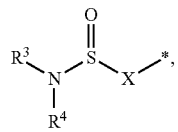
(A13)

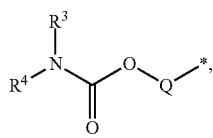
(A14)

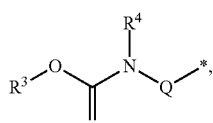
(A15)

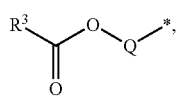
(A16)

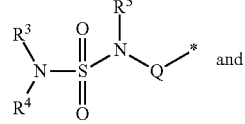
(A17)
and

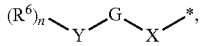
(A18)

wherein

R$^3$, R$^4$, R$^5$ which may be identical or different, denote hydrogen or a group selected from among C$_1$-C$_8$-alkyl, C$_3$-C$_8$-cycloalkyl, C$_2$-C$_6$-haloalkyl, C$_1$-C$_4$-alkyl-C$_3$-C$_8$-cycloalkyl, C$_3$-C$_8$-cycloalkyl-C$_1$-C$_4$-alkyl, NR$^7$R$^8$, NR$^7$R$^8$—C$_1$-C$_4$-alkyl, C$_1$-C$_4$-alkoxy, C$_1$-C$_4$-alkoxy-C$_1$-C$_4$-alkyl, C$_6$-C$_{14}$-aryl and C$_5$-C$_{10}$-heteroaryl, which may optionally be substituted by one or more of the groups, which may be identical or different, selected from among halogen, NH$_2$, OH, CN, NR$^9$R$^{10}$, —NH(CO)—C$_1$-C$_4$-alkyl and MeO, or in each case two of the substituents R$^3$, R$^4$, R$^5$ together form a five-, six- or seven-membered ring, consisting of carbon atoms and optionally 1-2 heteroatoms, selected from among oxygen, sulphur and nitrogen; which may optionally be substituted by one or more of the groups, which may be identical or different, selected from among halogen, NH$_2$, OH, CN, NR$^9$R$^{10}$, —NH(CO)—C$_1$-C$_4$-alkyl and MeO, R$^6$ which may be identical or different, denote hydrogen or a group, selected from among C$_1$-C$_8$-alkyl, C$_2$-C$_6$-alkenyl C$_3$-C$_8$-cycloalkyl, C$_2$-C$_6$-haloalkyl, C$_6$-C$_{14}$-aryl, C$_5$-C$_{10}$-heteroaryl and C$_3$-C$_8$-heterocycloalkyl, which may optionally be substituted by one or more of the groups, which may be identical or different, selected from among NH$_2$, NHMe, NMe$_2$, OH, OMe, CN, —C$_1$-C$_3$-alkyl-C$_6$-C$_{14}$-aryl, —NH—CO—NH—C$_1$-C$_3$-alkyl, C$_1$-C$_6$-alkyl and —(CO)O—C$_1$-C$_6$-alkyl or a group selected from among =O, NR$^7$R$^8$, OR$^7$, —CO—C$_1$-C$_3$-alkyl-NR$^7$R$^8$—O—C$_1$-C$_3$-alkyl-NR$^7$R$^8$, CONR$^7$R$^8$, NR$^7$COR$^8$, —CO—C$_1$-C$_3$-alkyl-NR$^7$(CO)OR$^8$, —O(CO)NR$^7$R$^8$, NR$^7$(CO)NR$^8$R$^9$, NR$^7$(CO)OR$^8$, (CO)OR$^7$, —O(CO)R$^7$, COR$^7$, (SO)R$^7$, (SO$_2$)R$^7$, (SO$_2$)NR$^7$R$^8$, NR$^7$(SO$_2$)R$^8$, NR$^7$(SO$_2$)NR$^8$R$^9$, CN and halogen;

n denotes 1, 2 or 3

R$^7$, R$^8$, R$^9$ which may be identical or different, denote hydrogen or a group selected from among C$_1$-C$_8$-alkyl, C$_3$-C$_8$-cycloalkyl, C$_2$-C$_6$-haloalkyl, C$_1$-C$_4$-alkyl-C$_3$-C$_8$-cycloalkyl, C$_3$-C$_8$-cycloalkyl-C$_1$-C$_3$-alkyl, C$_6$-C$_{14}$-aryl, C$_1$-C$_4$-alkyl-C$_6$-C$_{14}$-aryl, C$_6$-C$_{14}$-aryl-C$_1$-C$_4$-alkyl, C$_3$-C$_8$-heterocycloalkyl, C$_1$-C$_5$-alkyl-C$_3$-C$_8$-heterocycloalkyl, C$_3$-C$_8$-heterocycloalkyl-C$_1$-C$_4$-alkyl, C$_1$-C$_4$-alkyl(CO)— and C$_1$-C$_4$-alkyl-O(CO), which may optionally be substituted by one or more of the groups, which may be identical or different, selected from among halogen, NH$_2$, OH, CN, OMe, NHMe, NMe$_2$, C$_1$-C$_6$-alkyl and (CO)O C$_1$-C$_6$-alkyl, or in each case two of the substituents R$^7$, R$^8$, R$^9$ together form a five-, six- or seven-membered ring, consisting of carbon atoms and optionally 1-2 heteroatoms, selected from among oxygen, sulphur and nitrogen; which may optionally be substituted by one or more of the groups, which may be identical or different, selected from among halogen, NH$_2$, OH, CN, OMe, NH Me, NMe$_2$, C$_1$-C$_6$-alkyl and (CO)O C$_1$-C$_6$-alkyl.

Also preferred are compounds of formula (I), wherein
A, R$^a$ and R$^1$ to R$^{16}$ may have the meaning specified and R$^b$ denotes hydrogen.

Also preferred are compounds of formula (I), wherein
R$^1$ to R$^{16}$ may have the meaning specified and
R$^a$ denotes C$_6$-C$_{14}$-aryl or C$_1$-C$_6$-alkyl
wherein R$^a$ may optionally be substituted by one or more of the groups, which may be identical or different, selected from among
C$_1$-C$_6$-alkyl, C$_2$-C$_6$-alkenyl, C$_2$-C$_6$-alkynyl, C$_3$-C$_8$-cycloalkyl, C$_1$-C$_6$-haloalkyl, halogen, OH, C$_1$-C$_4$-alkoxy, CN, NO$_2$, NR$^{10}$R$^{11}$, OR$^{10}$, COR$^{10}$, COOR$^{10}$, CONR$^{10}$R$^{11}$, NR$^{10}$COR$^{11}$, NR$^{10}$(CO)NR$^{11}$R$^{12}$, O(CO)NR$^{10}$R$^{11}$, NR$^{10}$(CO)OR$^{11}$, SO$_2$R$^{10}$, SOR$^{10}$, SO$_2$NR$^{10}$R$^{11}$, NR$^{10}$SO$_2$NR$^{11}$R$^{12}$ and NR$^{10}$SO$_2$R$^{11}$;
and
R$^b$ denotes hydrogen.

Also preferred are compounds of formula (I), wherein
A, R$^a$ and R$^b$ may have the meaning specified and
R$^1$ denotes hydrogen, C$_1$-C$_5$-alkyl or C$_3$-C$_8$-cycloalkyl,
R$^2$ denotes hydrogen, C$_1$-C$_5$-alkyl or C$_3$-C$_8$-cycloalkyl, phenyl or R$^1$ and R$^2$ together form an optionally substituted five- or six-membered ring consisting of carbon atoms and optionally 1 to 2 nitrogen atoms, or R$^1$ and R$^2$ together form an optionally substituted nine- to thirteen-membered spirocyclic ring, or R$^1$, R$^2$ which may be identical or different, denote a group selected from among general formulae (A1)-A(17), wherein X denotes a bond or an optionally substituted C$_1$-C$_3$-alkylene, or X together with R$^1$, R$^3$ or R$^4$ may form a C1-7 alkylene bridge;

Q denotes an optionally substituted C$_1$-C$_3$-alkylene,

Q together with R$^1$, R$^3$ or R$^4$ may form a C$_1$-C$_7$-alkylene bridge;

R$^3$, R$^4$, R$^5$ which may be identical or different, denote hydrogen or an optionally substituted group selected from among C$_1$-C$_4$-alkyl, C$_1$-C$_4$-alkoxy, C$_3$-C$_6$-cycloalkyl, C$_3$-C$_8$-heterocycloalkyl, —C$_1$-C$_3$-alkyl-C$_3$-C$_6$-cycloalkyl, phenyl and C$_5$-C$_{10}$-heteroaryl or in each case two of the substituents R$^3$, R$^4$, R$^5$ together form an optionally substituted five- or six-membered ring, consisting of carbon atoms and optionally 1-2 heteroatoms, selected from among oxygen and nitrogen.

Particularly preferred are compounds of formula (I), wherein
A, R$^a$ and R$^b$ may have the meaning specified and
R$^1$ denotes H, Me
R$^2$ denotes hydrogen or a group of general formulae (A18), wherein
X denotes a bond or an optionally substituted group selected from among C$_1$-C$_7$-alkylene, C$_3$-C$_7$-alkenylene and C$_3$-C$_7$-alkynylene, or X together with R$^1$ may form a C$_{1-7}$-alkylene bridge;
Y denotes a bond or methylene, ethylene;
X and Y may be linked to the same or different atoms of G, and
G denotes a saturated, partially saturated or unsaturated ring system consisting of 3-10 C atoms, wherein optionally up to 6 C atoms are replaced by heteroatoms selected from among nitrogen, oxygen and sulphur;
R$^6$ which may be identical or different, denote hydrogen or an optionally substituted group selected from among =O, C$_1$-C$_4$-alkyl, C$_2$-C$_6$-alkenyl, C$_3$-C$_6$-cycloalkyl, C$_6$-C$_{14}$-aryl, C$_5$-C$_6$-heterocycloalkyl, and C$_5$-C$_6$-heteroaryl or a group selected from among NR$^7$R$^8$, OR$^7$, —O—C$_1$-C$_3$-alkyl-NR$^7$R$^8$, CONR$^7$R$^8$, CO—C$_1$-C$_3$-alkyl-NR$^7$R$^8$NR$^7$COR$^8$, NR$^7$(CO)OR$^8$, —CO—C$_1$-C$_3$-alkyl-NR$^7$(CO)OR$^8$, NR$^7$(CO)NR$^8$R$^9$, NR$^7$(CO)OR$^8$, (CO)OR$^7$, COR$^7$, (SO$_2$)R$^7$, —C$_1$-C$_3$-alkyl-C$_6$-C$_{14}$-aryl, —NH—CO—NH—C$_1$-C$_3$-alkyl and CN, n denotes 1 or 2

R$^7$, R$^8$, R$^9$ which may be identical or different, denote hydrogen or an optionally substituted group selected from among C$_1$-C$_5$-alkyl, C$_1$-C$_4$-alkyl-C$_6$-C$_{14}$-aryl, C$_3$-C$_6$-heterocycloalkyl, C$_1$-C$_5$-alkyl-C$_3$-C$_8$-heterocycloalkyl and C$_3$-C$_6$-cycloalkyl, or in each case two of the substituents R$^7$, R$^8$, R$^9$ together form an optionally substituted five- or six-membered ring, consisting of carbon atoms and optionally 1-2 heteroatoms, selected from among oxygen and nitrogen.

The invention further relates to compounds of formula (I) for use as pharmaceutical compositions.

The invention further relates to the use of the compounds of formula (I) for preparing a pharmaceutical composition for the treatment of diseases in whose pathology an activity of PI3-kinases is implicated, wherein therapeutically effective doses of the compounds of formula (I) may confer a therapeutic benefit.

The invention further relates to the use of the compounds of formula (I), for preparing a pharmaceutical composition for the treatment of inflammatory and allergic diseases of the airways.

The invention further relates to the use of the compounds of formula (I), for preparing a pharmaceutical composition for the treatment of a disease, which is selected from among chronic bronchitis, bronchitis caused by bacterial or viral infections or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha1-antitrypsin deficiency, coughing, pulmonary emphysema, interstitial lung diseases, alveolitis, hyperreactive airways, nasal polyps, pulmonary oedema, pneumonitis of various causes, such as radiation-induced or caused by aspiration or infection, collagenoses such as lupus erythematodes, systemic scleroderma, sarcoidosis and Boeck's disease.

The invention further relates to the use of the compounds of formula (I), for preparing a pharmaceutical composition for the treatment of inflammatory and allergic diseases of the skin.

The invention further relates to the use of the compounds of formula (I), for preparing a pharmaceutical composition for the treatment of a disease which is selected from among psoriasis, contact dermatitis, atopical dermatitis, alopecia areata (circular hair loss), erythema exsudativum multiforme (Stevens-Johnson Syndrome), dermatitis herpetiformis, scleroderma, vitiligo, nettle rash (urticaria), lupus erythematodes, follicular and surface pyoderma, endogenous and exogenous acne, acne rosacea and other inflammatory and allergic or proliferative skin complaints.

The invention further relates to the use of the compounds of formula (I), for preparing a pharmaceutical composition for the treatment of inflammation of the eye.

The invention further relates to the use of the compounds of formula (I), for preparing a pharmaceutical composition for the treatment a disease which is selected from among conjunctivitis of various kinds, such as e.g. caused by fungal or bacterial infections, allergic conjunctivitis, irritable conjunctivitis, conjunctivitis caused by drugs, keratitis and uveitis.

The invention further relates to the use of the compounds of formula (I), for preparing a pharmaceutical composition for the treatment of diseases of the nasal mucosa.

The invention further relates to the use of the compounds of formula (I), for preparing a pharmaceutical composition for the treatment of a disease, which is selected from among allergic rhinitis, allergic sinusitis and nasal polyps.

The invention further relates to the use of the compounds of formula (I), for preparing a pharmaceutical composition for the treatment of inflammatory or allergic conditions involving autoimmune reactions.

The invention further relates to the use of the compounds of formula (I), for preparing a pharmaceutical composition for the treatment of a disease which is selected from among Crohn's disease, ulcerative colitis, systemic lupus erythematodes, chronic hepatitis, multiple sclerosis, rheumatoid arthritis, psoriatic arthritis, osteoarthritis, rheumatoid spondylitis.

The invention further relates to the use of the compounds of formula (I), for preparing a pharmaceutical composition for the treatment of kidney inflammation.

The invention further relates to the use of the compounds of formula (I), for preparing a pharmaceutical composition for the treatment of a disease which is selected from among glomerulonephritis, interstitial nephritis and idiopathic nephrotic syndrome.

Of particular importance according to the invention is a pharmaceutical formulation containing a compound of formula (I).

Preferred is an inhaled pharmaceutical formulation containing a compound of formula (I).

Also preferred is an orally administered pharmaceutical formulation containing a compound of formula (I).

TERMS AND DEFINITIONS USED

By alkyl groups as well as alkyl groups which are part of other groups are meant branched and unbranched alkyl groups with 1 to 10 carbon atoms, preferably 1-6, particularly preferably 1-4 carbon atoms, are meant for example: methyl, ethyl, propyl, butyl, pentyl, hexyl, heptyl, octyl, nonyl and decyl. Unless stated otherwise, the above terms propyl, butyl, pentyl, hexyl, heptyl, octyl, nonyl and decyl include all the possible isomeric forms. For example the term propyl includes the two isomeric groups n-propyl and iso-propyl, the term butyl includes n-butyl, iso-butyl, sec. butyl and tert.-butyl, the term pentyl includes isopentyl, neopentyl etc.

In the above-mentioned alkyl groups, unless otherwise specified, one or more hydrogen atoms may be replaced by other groups. For example these alkyl groups may be substituted by the halogen atoms fluorine, chlorine, bromine or iodine. The substituents fluorine or chlorine are preferred. It is also possible for all the hydrogen atoms of the alkyl group to be replaced.

By alkyl bridge is meant, unless stated otherwise, branched and unbranched double-bonded alkyl groups with 4 to 7 carbon atoms, for example, n-butylene, iso-butylene, sec. butylene and tert.-butylene, pentylene, iso-pentylene, neopentylene, etc. bridges. Particularly preferred are n-butylene or n-pentylene bridges. In the above-mentioned alkyl bridges 1 to 2 C atoms may optionally be replaced by one or more heteroatoms selected from among oxygen or sulphur.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Preferred are alkylene groups with 1 to 4 carbon atoms. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

Examples of alkenyl groups (including those which are part of other groups) are branched and unbranched alkenyl groups with 2 to 10 carbon atoms, preferably 2-6 carbon atoms, particularly preferably 2-3 carbon atoms, provided that they have at least one double bond. Examples include: ethenyl, propenyl, butenyl, pentenyl etc. Unless stated otherwise, the above-mentioned terms propenyl, butenyl etc. include all the possible isomeric forms. For example the term butylene includes n-butenyl, 1-methylpropenyl, 2-methylpropenyl, 1,1-dimethylethenyl, 1,2-dimethylethenyl etc.

In the above-mentioned alkenyl groups, unless otherwise stated, optionally one or more hydrogen atoms may optionally be replaced by other groups. For example these alkyl groups may be substituted by the halogen atoms fluorine, chlorine, bromine or iodine. The substituents fluorine and chlorine are preferred. Particularly preferred is the substituent chlorine. Optionally all the hydrogen atoms of the alkenyl group may be replaced.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

Examples of alkynyl groups (including those which are part of other groups) are branched and unbranched alkynyl groups with 2 to 10 carbon atoms, provided that they have at least one triple bond, for example ethynyl, propargyl, butynyl, pentynyl, hexynyl etc., preferably ethynyl or propynyl.

Preferred are alkynyl groups with 2 to 4 carbon atoms. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus, for example propynyl includes 1-propynyl and 2-propynyl, butynyl includes 1-, 2- and 3-butynyl, 1-methyl-1-propynyl, 1-methyl-2-propynyl etc.

In the above-mentioned alkynyl groups one or more hydrogen atoms may optionally be substituted by other groups unless stated otherwise. For example these alkyl groups may be substituted by the halogen atoms fluorine, chlorine, bromine or iodine. The substituents fluorine and chlorine are preferred. Optionally all the hydrogen atoms of the alkynyl group may be replaced.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Preferred are alkynylene groups with 2 to 4 carbon atoms. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the groups in question with the same number of carbons. Thus, for example propynyl also includes 1-methylethynylene and butynylene includes 1-methylpropynylene, 1,1-dimethylethynylene, 1,2-dimethylethynylene.

By cycloalkyl groups (including those which are part of other groups) are meant saturated cycloalkyl groups with 3-8 carbon atoms, for example cyclopropyl, cyclobutyl, cyclopentyl, cyclohexyl, cycloheptyl or cyclooctyl, preferably cyclopropyl, cyclopentyl or cyclohexyl, while each of the above-mentioned cycloalkyl groups may optionally carry one or more substituents or be anellated to a benzene ring. Moreover the cycloalkyl groups may form, in addition to monocyclic groups, bicyclic, bridged or spirocyclic ring systems.

By cycloalkenyl (including those which are part of other groups) are meant cyclic alkyl groups with 5 to 8, preferably 5 or 6 carbon atoms, which contain one or two double bonds. Examples include: cyclopentenyl, cyclopentadienyl, cyclohexenyl, cyclohexadienyl, cycloheptenyl, cycloheptadienyl, cyclooctenyl or cyclooctadienyl. Moreover the cycloalkenyl groups may form, in addition to monocyclic groups, bicyclic, bridged or spirocyclic ring systems.

By cycloalkynyl (including those which are part of other groups) are meant cyclic alkyl groups with 5 to 8, preferably 5 or 6 carbon atoms, which contain one or two triple bonds. Examples of these include: cyclopentynyl, cyclopentadienyl, cyclohexenyl, cyclohexadienyl, cycloheptenyl, cycloheptadienyl, cyclooctenyl or cyclooctadienyl. Moreover the cycloalkynyl groups may form, in addition to monocyclic ring systems, bicyclic, bridged or spirocyclic ring systems.

By haloalkyl (including those which are part of other groups) are meant branched and unbranched alkyl groups with 1 to 6 carbon atoms, wherein one or more hydrogen atoms are replaced by a halogen atom selected from among fluorine, chlorine or bromine, preferably fluorine and chlorine. By the term "$C_{1-4}$-haloalkyl" are meant correspondingly branched and unbranched alkyl groups with 1 to 4 carbon atoms, wherein one or more hydrogen atoms are replaced as described above. $C_{1-4}$-haloalkyl is preferred. Examples of these include: $CH_2F$, $CHF_2$, $CF_3$.

The term aryl denotes an aromatic ring system with 6 to 14 carbon atoms, preferably 6 or 10 carbon atoms, for example phenyl or naphthyl, preferably phenyl, which, unless otherwise described, may have one or more substituents, for example. Moreover each of the above-mentioned aryl systems may optionally be anellated to a heterocycloalkyl group or a cycloalkyl group. Examples include: 2,3-dihydro-benzo[1,4]dioxine, benzo[1,3]dioxole, 1,2,3,4-tetrahydro-naphthalene and 3,4-dihydro-1H-quinolin-2-one.

By heterocycloalkyl groups are meant, unless otherwise described in the definitions, 5-, 6- or 7-membered, saturated or unsaturated, bridged, mono- or bicyclic heterocycles wherein up to four C atoms may be replaced by one or more heteroatoms selected from among oxygen, nitrogen or sulphur, for example tetrahydrofuran, tetrahydrofuranone, γ-butyrolactone, α-pyran, γ-pyran, dioxolane, tetrahydropyran, dioxane, dihydrothiophene, thiolane, dithiolane, pyrroline, pyrrolidine, pyrazoline, pyrazolidine, imidazoline, imidazolidine, tetrazole, piperidine, pyridazine, pyrimidine, pyrazine, piperazine, triazine, tetrazine, morpholine, thiomorpholine, diazepan, oxazine, tetrahydro-oxazinyl, isothiazole, pyrazolidine, preferably pyrazolyl, pyrrolidinyl, piperidinyl, piperazinyl or tetrahydro-oxazinyl, while the heterocycle may optionally be substituted, preferably by fluorine or methyl. The ring may be linked to the molecule through a carbon atom or if available through a nitrogen atom.

Unless otherwise mentioned, a heterocyclic ring may be provided with a keto group. Examples of these include.

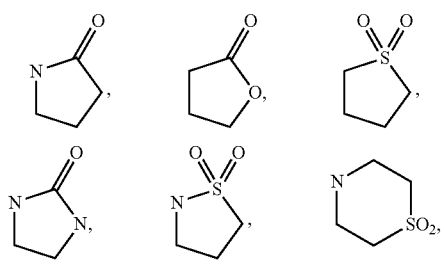

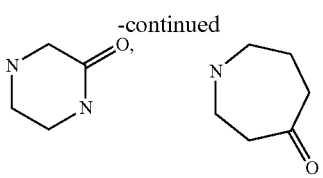

Examples of 5-10-membered bicyclic heterorings include pyrrolizine, indole, indolizine, isoindole, indazole, purine, quinoline, isoquinoline, benzimidazole, benzofuran, benzopyran, benzothiazole, benzothiazole, benzisothiazole, pyridopyrimidine, pteridine, pyrimidopyrimidine,

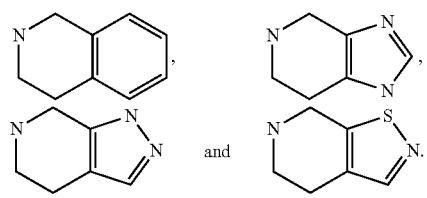

Examples of heteroaryl include 5-10-membered mono- or bicyclic heteroaryl rings in which up to three C atoms may be replaced by one or more heteroatoms selected from among oxygen, nitrogen or sulphur, while these may contain so many conjugated double bonds that an aromatic system is formed. Each of the above-mentioned heterocycles may optionally also be anellated to a benzene ring. Preferred examples of anellated heteroaryl groups are: benzimidazole, indole and pyrimidopyrimidine. Moreover each of the above-mentioned heterocycles may optionally be anellated to a heterocycloalkyl group or a cycloalkyl group.

The heteroaryl rings may, for example, unless otherwise described, carry one or more substituents, preferably halogen or methyl.

The ring may be linked to the molecule through a carbon atom or if present through a nitrogen atom. The following are examples of five- or six-membered heterocyclic aromatic groups:

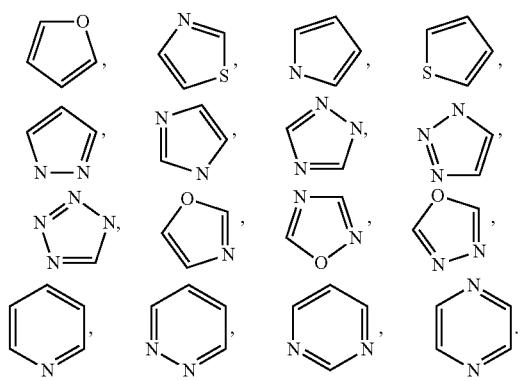

Examples of 5-10-membered bicyclic heteroaryl rings include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine.

By the term heterocyclic spiro rings ("spiro") are meant 5-10 membered, spirocyclic rings which may optionally contain one, two or three heteroatoms, selected from among oxygen, sulphur and nitrogen, while the ring may be connected to the molecule via a carbon atom or, if present, via a nitrogen atom. Unless otherwise stated, a spirocyclic ring may be provided with a keto group. Examples include:

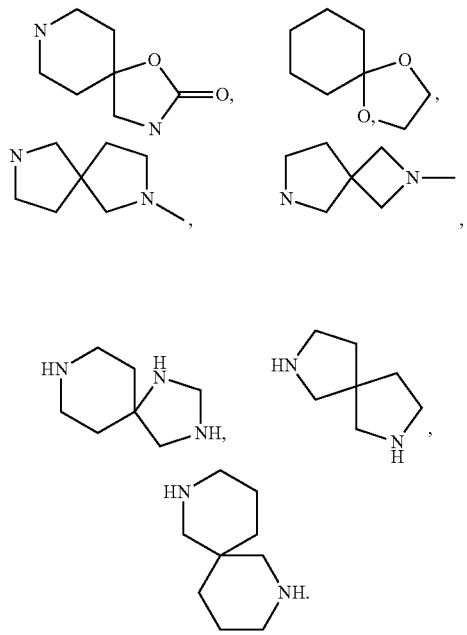

By the term "optionally substituted" is meant, unless stated otherwise, within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

"=O" denotes an oxygen atom linked by a double bond.

The term halogen generally denotes fluorine, chlorine, bromine or iodine.

The compounds according to the invention may occur in the form of the individual optical isomers, mixtures of the individual enantiomers, diastereomers or racemates, in the form of the tautomers as well as in the form of the free bases or the corresponding acid addition salts with pharmacologically acceptable acids—such as for example acid addition salts with hydrohalic acids, for example hydrochloric or hydrobromic acid, or organic acids, such as for example oxalic, fumaric, diglycolic or methanesulphonic acid.

Where a hyphen open on one side "-" is used in the structural formula of a substituent, this hyphen is to be understood as the linkage point to the remainder of the molecule. The substituent replaces the corresponding groups $R^2$, $R^6$, etc. If no hyphen open on one side is used in the structural formula of a substituent, the linkage point to the remainder of the molecule is clear from the structural formula itself.

The substituent $R^a$ may be hydrogen or an optionally substituted group selected from among $C_1$-$C_8$-alkyl, $C_2$-$C_8$-alkenyl, $C_2$-$C_8$-alkynyl, $C_3$-$C_8$-cycloalkyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_4$-alkyl, spiro, $C_3$-$C_8$-heterocycloalkyl and $C_3$-$C_8$-heterocycloalkyl-$C_1$-$C_4$-alkyl, preferably phenyl, wherein $R^a$ may preferably be substituted by one or more, preferably one or two, groups selected from among $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, halogen, OH, $C_1$-$C_4$-alkoxy, CN, $NO_2$, $NR^{10}R^{11}$, $OR^{10}$, $COR^{10}$, $COOR^{10}$, $CONR^{10}R^{11}$, $NR^{10}COR^{11}$, $NR^{10}(CO)NR^{11}R^{12}$, $O(CO)NR^{10}R^{11}$, $NR^{10}(CO)OR^{11}$, $SO_2R^{10}$, $SOR^{10}$, $SO_2NR^{10}R^{11}$, $NR^{10}SO_2NR^{11}R^{12}$ and $NR^{10}SO_2R^{11}$, preferably $C_1$-$C_6$-haloalkyl, halogen and CONR10R11, particularly preferably $CF_3$, F, Cl, Br and $CONHCH_3$.

Particularly preferably $R^a$ denotes phenyl, substituted by one or more of the groups selected from among $CF_3$, F, Cl, Br and $CONHCH_3$. Also particularly preferably $R^a$ denotes butyl.

The substituents $R^{10}$, $R^{11}$, $R^{12}$, which may be identical or different, may denote hydrogen or a group selected from among
$C_1$-$C_6$-alkyl, $C_2$-$C_6$-alkenyl, $C_2$-$C_6$-alkynyl, $C_3$-$C_8$-cycloalkyl and $C_1$-$C_6$ haloalkyl; or
in each case two of the groups
$R^{10}$, $R^{11}$, $R^{12}$ together form a five-, six- or seven-membered ring, consisting of carbon atoms and optionally 1-2 heteroatoms, selected from among oxygen, sulphur and nitrogen.

The substituent $R^b$ may represent hydrogen, OH or $NH_2$ or an optionally substituted group selected from among $C_1$-$C_8$-alkyl, $C_3$-$C_8$-cycloalkyl, $C_2$-$C_8$-alkenyl, $C_2$-$C_8$-alkynyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_4$-alkyl, spiro, $C_3$-$C_8$-heterocycloalkyl, $CONH_2$, $C_6$-$C_{14}$-aryl-NH, $C_3$-$C_8$-heterocycloalkyl-NH— and O—$C_1$-$C_3$-alkyl, which is preferably unsubstituted or substituted by one or more of the groups, which may be identical or different, selected from among
$C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, halogen, OH, OMe, CN, $NH_2$, NHMe and $NMe_2$.

Preferably $R^b$ denotes hydrogen OH or $NH_2$, or a group selected from among $C_1$-$C_8$-alkyl, $C_2$-$C_8$-alkenyl, $C_2$-$C_8$-alkynyl, $C_3$-$C_8$-cycloalkyl, $C_6$-$C_{14}$-aryl, haloalkyl, $C_5$-$C_{10}$-heteroaryl and $C_6$-$C_{14}$-aryl-NH, which may optionally be substituted by one or more of the groups, which may be identical or different, selected from among $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, halogen, OH, OMe, CN, $NH_2$, NHMe, $NMe_2$.

Particularly preferably $R^b$ denotes hydrogen.

The substituent $R^1$ may represent hydrogen or an optionally substituted group selected from among $C_1$-$C_8$-alkyl, $C_3$-$C_8$-cycloalkyl, $C_2$-$C_8$-alkenyl, $C_2$-$C_8$-alkynyl and $C_6$-$C_{14}$-aryl-$C_1$-$C_5$-alkyl. Preferably $R^1$ denotes hydrogen, $C_1$-$C_5$-alkyl or $C_3$-$C_8$-cycloalkyl. Particularly preferably the substituent $R^1$ denotes hydrogen or a group selected from among methyl, ethyl, propyl, cyclopropyl, cyclobutyl and piperidine; particularly preferably $R^1$ denotes hydrogen or methyl.

The substituent $R^1$ may preferably be substituted by one or more of the groups, which may be identical or different, selected from among halogen, COOH, $NH_2$, OH, CN, $C_1$-$C_6$-alkyl, OMe, —NH(CO)alkyl and —(CO)O—$C_1$-$C_4$-alkyl.

The substituent $R^2$ may represent hydrogen or an optionally substituted group selected from among $C_1$-$C_8$ alkyl, $C_3$-$C_8$-cycloalkyl, $C_2$-$C_8$-alkenyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_6$-alkyl, $C_9$-$C_{13}$-spiro, $C_3$-$C_8$-heterocycloalkyl, $C_3$-$C_8$-heterocycloalkyl-$C_1$-$C_6$-alkyl- and $C_6$-$C_{14}$-aryl-$C_1$-$C_6$-alkyl-. Preferably $R^2$ denotes hydrogen or a group selected from among $C_1$-$C_5$-alkyl, $C_3$-$C_8$-cycloalkyl-$C_1$-$C_4$-alkyl, $C_6$-$C_{14}$-aryl-$C_1$-$C_5$-alkyl, $C_3$-$C_8$-heterocycloalkyl-$C_1$-$C_6$-alkyl- and $C_5$-$C_{10}$-heteroaryl-$C_1$-$C_6$-alkyl-. Particularly preferably $R^2$ denotes hydrogen or a group selected from among methyl, ethyl, propyl, butyl, pentyl, $C_3$-$C_6$-cycloalkyl and phenyl, particularly preferably hydrogen or methyl.

The substituent $R^2$ may preferably be substituted by one or more of the groups, which may be identical or different, selected from among =O halogen, $NH_2$, OH, CN, $C_1$-$C_6$-alkyl, OMe, —NH(CO)alkyl and —(CO)O—$C_1$-$C_4$-alkyl.

The substituents $R^1$ and $R^2$ may together form an optionally substituted, five-, six- or seven-membered ring consisting of carbon atoms and optionally 1 to 2 heteroatoms, selected from among oxygen, sulphur and nitrogen, preferably nitrogen. Particularly preferably the group $NR^1R^2$ denotes an optionally substituted pyrrolidinyl or morpholine group.

The ring formed from the substituents $R^1$ and $R^2$ may preferably be substituted by one or more of the groups, which may be identical or different, selected from among heterocycloalkyl, halogen, $NH_2$, OH, CN, $C_1$-$C_6$-alkyl, OMe, —NH(CO)alkyl and —(CO)O—$C_1$-$C_4$-alkyl.

The substituents $R^1$ and $R^2$ may together form an optionally substituted nine- to thirteen-membered spirocyclic ring, preferably

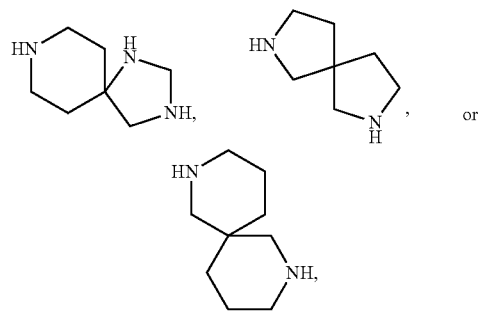

which is preferably substituted by a group selected from among methyl, ethyl, OH, =O and phenyl.

The substituent $R^2$ may furthermore denote a group selected from among general formulae (A1) to (A18)

(A1)

(A2)

-continued

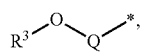 (A3)

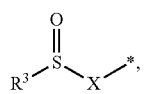 (A4)

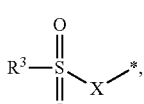 (A5)

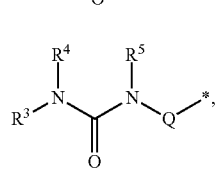 (A6)

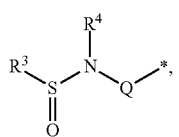 (A7)

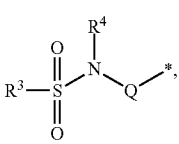 (A8)

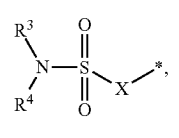 (A9)

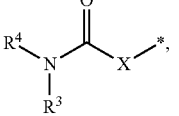 (A10)

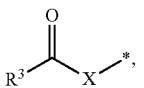 (A11)

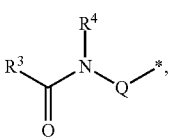 (A12)

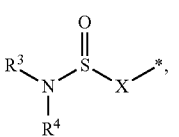 (A13)

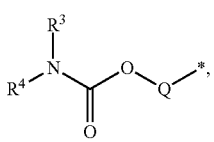 (A14)

-continued

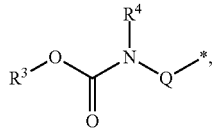 (A15)

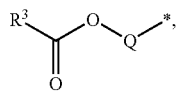 (A16)

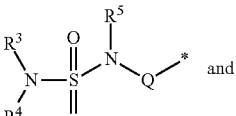 (A17) and

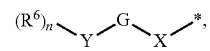 (A18)

preferably (A1), (A2), (A3), (A6), (A8), (A10), (A11), (A17) and (A18).

X and Y may be linked to the same or different atoms of G.

X may denote a bond or an optionally substituted group selected from among $C_1$-$C_7$-alkylene, $C_3$-$C_7$-alkenylene and $C_3$-$C_7$-alkynylene, preferably a bond, methylene and ethylene.

X may form together with $R^1$, $R^3$ or $R^4$ a $C_1$-$C_7$-alkylene bridge, preferably may form a 5- or 6-membered heterocyclic group with $R^1$, $R^3$ or $R^4$, particularly preferably may form a piperidinone or pyrrolidinone ring with $R^3$ or $R^4$, which may optionally be substituted. The substituent R1 and X together preferably form a pyrrolidine or piperidine group.

Y may represent a bond or optionally substituted $C_1$-$C_4$-alkylene, preferably a bond, methylene or ethylene.

Q may denote an optionally substituted group selected from among $C_1$-$C_7$-alkylene, $C_3$-$C_7$-alkenylene and $C_3$-$C_7$-alkynylene; preferably optionally substituted $C_1$-$C_3$-alkylene, particularly preferably ethyl and propyl.

Q together with $R^1$, $R^3$ or $R^4$ may form a $C_1$-$C_7$-alkylene bridge. R1 and Q preferably form a pyrrolidines or piperidine group.

The substituents $R^3$, $R^4$, $R^5$ which may be identical or different, may denote hydrogen or an optionally substituted group selected from among $C_1$-$C_8$-alkyl, $C_3$-$C_8$-cycloalkyl, $C_2$-$C_6$-haloalkyl, $C_1$-$C_4$-alkyl-$C_3$-$C_8$-cycloalkyl, $C_3$-$C_8$-cycloalkyl-$C_1$-$C_4$-alkyl, $NR^7R^8$, $NR^7R^8$—$C_1$-$C_4$-alkyl, $C_1$-$C_4$-alkoxy, $C_1$-$C_4$-alkoxy-$C_1$-$C_4$-alkyl, $C_6$-$C_{14}$-aryl and $C_5$-$C_{10}$-heteroaryl; preferably hydrogen, or an optionally substituted group selected from among $C_1$-$C_4$-alkyl, $C_1$-$C_4$-alkoxy and $C_3$-$C_6$-cycloalkyl, particularly preferably hydrogen, methyl, methoxy, ethoxy, propyloxy, butyloxy, cyclopropyl and cyclopentyl.

Two of the substituents $R^3$, $R^4$, $R^5$ may together form an optionally substituted five-, six- or seven-membered ring, preferably a 5- or 6-membered ring, consisting of carbon atoms and optionally 1-2 heteroatoms, selected from among oxygen, sulphur and nitrogen; preferably from oxygen or nitrogen. Preferably the group $NR^3R^4$ denotes pyrrolidine, piperidine or morpholine.

The substituents $R^3$, $R^4$, $R^5$ or the ring formed from them may preferably be substituted by one or more of the groups, which may be identical or different, selected from among halogen, $NH_2$, OH, CN, $NR^9R^{10}$, —NH(CO)—$C_1$-$C_4$-alkyl and MeO.

A may represent N or CH, preferably N.

G may represent a saturated, partially saturated or unsaturated ring system consisting of 3-10 C atoms, wherein optionally up to 4 C atoms are replaced by heteroatoms selected from among nitrogen, oxygen and sulphur. Preferably G may represent a saturated, partially saturated or unsaturated ring system consisting of 3-8 C atoms, particularly preferably 5-6 C atoms, wherein optionally up to 6 C atoms, particularly preferably up to 4 C atoms are replaced by heteroatoms selected from among nitrogen, oxygen and sulphur. Preferably G denotes a ring system consisting of one or two 5-6-membered rings, particularly preferably selected from among furan, cyclohexyl, cyclopropyl, phenyl, pyrrolidine, piperidine, tetrahydroquinoline, tetrahydroisoquinoline, indole, dihydroisoindole, piperazine, pyrrole, pyrazole, pyridine, imidazolidine, imidazole, thiophene, thiazole, triazole, oxazole, oxadiazole, tetrazole, morpholine, benzimidazole, benzopyrrole, benzodioxole, and dihydro-benzo[1,4]dioxine, particularly preferably furan, cyclohexyl, cyclopropyl, phenyl, pyrrolidine, piperidine, tetrahydroquinoline, tetrahydroisoquinoline, dihydroisoindole, pyrrole, pyrazole, pyridine, imidazolidine, imidazole, thiophene, thiazole, oxazole, oxadiazole, tetrazole, morpholine, benzimidazole, benzodioxole and dihydro-benzo[1,4]dioxine.

The substituent $R^6$, which may be identical or different, may denote hydrogen or an optionally substituted group, selected from among $C_1$-$C_8$-alkyl, $C_2$-$C_6$-alkenyl, $C_3$-$C_8$-cycloalkyl, $C_2$-$C_6$-haloalkyl, $C_6$-$C_{14}$-aryl, $C_5$-$C_{10}$-heteroaryl, $C_3$-$C_8$-heterocycloalkyl, preferably hydrogen or an optionally substituted group selected from among $C_1$-$C_4$-alkyl, $C_3$-$C_6$-cycloalkyl, $C_6$-$C_{14}$-aryl, $C_5$-$C_6$-heterocycloalkyl, and $C_5$-$C_6$-heteroaryl, particularly preferably hydrogen or an optionally substituted group selected from among $C_1$-$C_4$-alkyl, $C_3$-$C_6$-cycloalkyl, $C_5$-$C_6$-heterocycloalkyl, $C_5$-$C_6$-heteroaryl and phenyl, or
denotes a group selected from among =O, $NR^7R^8$, $OR^7$, —CO—$C_1$-$C_3$-alkyl-$NR^7R^8$, —O—$C_1$-$C_3$-alkyl-$NR^7R^8$, $CONR^7R^8$, $NR^7COR^8$, $NR^7(CO)OR^8$, —CO—$C_1$-$C_3$-alkyl-$NR^7(CO)OR^8$, —O(CO)$NR^7R^8$, $NR^7(CO)NR^8R^9$, $NR^7(CO)OR^8$, $(CO)OR^7$, —O(CO)$R^7$, $COR^7$, $(SO)R^7$, $(SO_2)R^7$, $(SO_2)NR^7R^8$, $NR^7(SO_2)R^8$, $NR^7(SO_2)NR^8R^9$, CN and halogen;

preferably it denotes a group selected from among =O, $NR^7R^8$, $OR^7$, —CO—$C_1$-$C_3$-alkyl-$NR^7R^8$, $CONR^7R^8$, $NR^7(CO)OR^8$, $NR^7COR^8$, —CO—$C_1$-$C_3$-alkyl-$NR^7(CO)OR^8$, $NR^7(CO)NR^8R^9$, $NR^7(CO)OR^8$, $(CO)OR^7$, $COR^7$, $(SO_2)R^7$ and CN, particularly preferably =O, OMe, —NMe-CO—NH—$C_1$-$C_3$-alkyl, —NH—CO—$C_1$-$C_4$-alkyl, —NH—COO—$C_1$-$C_4$-alkyl, —COO—$C_1$-$C_4$-alkyl and $C_1$-$C_4$-alkyl.

Particularly preferably the substituent $R^6$ may denote hydrogen or a group selected from among =O, OH, CN, $CF_3$, $NH_2$, $OCF_3$, NHCOMe, NHCO-butyl, NHCO-cyclopentyl, NHCOcyclopropyl, NHCO-morpholine, NHCO—NHMe, NHCO—NHpropyl, NHCO—NMeMe, NHCO-NMepropyl, NHCOpropyl, NHCO-pyrrolidine, $NHSO_2$-Me, $CONH_2$, CONH, COOH, CONHMe, CONHpropyl, $CONMe_2$, CONMe-butyl, CONMe, CONH-cyclohexyl, CONH-cyclopropyl, COO-butyl, $SO_2Me$, $NHSO_2$—NMeMe, $NMe_2$, NMeCOMe, NMeCOObutyl, NMeMe, phenyl, methyl, ethyl, propyl, butyl, methoxy, phenyl, oxazolidine, morpholine, imidazole, imidazolidine, pyrazole, piperazine, piperidine, pyrimidine, pyrrolidine, pyrrolidine-CO, cyclopropyl, cyclopentyl and cyclohexyl.

The substituent $R^6$ may preferably be substituted by one or more of the groups, which may be identical or different, selected from among =O, $NH_2$, NHMe, $NMe_2$, OH, OMe, CN, —$C_1$-$C_3$-alkyl-$C_6$-$C_{14}$-aryl, —NH—CO—NH—$C_1$-$C_3$-alkyl and —(CO)O—$C_1$-$C_4$-alkyl.

n denotes 1, 2 or 3, preferably 1 or 2, particularly preferably 1.

The substituents $R^7$, $R^8$, $R^9$ which may be identical or different, may denote hydrogen or an optionally substituted group selected from among $C_1$-$C_8$-alkyl, $C_3$-$C_8$-cycloalkyl, $C_1$-$C_6$-haloalkyl, $C_1$-$C_4$-alkyl-$C_3$-$C_8$-cycloalkyl, $C_3$-$C_8$-cycloalkyl-$C_1$-$C_3$-alkyl, $C_6$-$C_{14}$-aryl, $C_1$-$C_4$-alkyl-$C_6$-$C_{14}$-aryl, $C_6$-$C_{14}$-aryl-$C_1$-$C_4$-alkyl, $C_3$-$C_8$-heterocycloalkyl, $C_1$-$C_5$-alkyl-$C_3$-$C_8$-heterocycloalkyl, $C_3$-$C_8$-heterocycloalkyl-$C_1$-$C_4$-alkyl, $C_1$-$C_4$-alkyl(CO)— and $C_1$-$C_4$-alkyl-O(CO)—; preferably $C_1$-$C_4$-alkyl, $C_1$-$C_2$-haloalkyl, $C_1$-$C_4$-alkyl-$C_3$-$C_8$-cycloalkyl, $C_3$-$C_8$-cycloalkyl-$C_1$-$C_3$-alkyl, phenyl, $C_1$-$C_4$-alkyl-$C_6$-$C_{14}$-aryl, $C_3$-$C_8$-heterocycloalkyl, $C_1$-$C_5$-alkyl-$C_3$-$C_8$-heterocycloalkyl, $C_1$-$C_4$-alkyl(CO)— and $C_1$-$C_4$-alkyl-O(CO), particularly preferably $C_1$-$C_5$-alkyl, $C_1$-$C_4$-alkyl-$C_6$-$C_{14}$-aryl, $C_3$-$C_6$-heterocycloalkyl and $C_1$-$C_5$-alkyl-$C_3$-$C_8$-heterocycloalkyl, or in each case two of the substituents $R^7$, $R^8$, $R^9$ together form an optionally substituted five-, six- or seven-membered ring, consisting of carbon atoms and optionally 1-2 heteroatoms, selected from among oxygen, sulphur and nitrogen; preferably an optionally substituted five- or six-membered ring, consisting of carbon atoms and optionally 1-2 heteroatoms, selected from among oxygen and nitrogen; particularly preferably nitrogen, The substituents $R^7$, $R^8$, $R^9$ or the ring system formed therefrom may preferably be substituted by one or more of the groups, which may be identical or different, selected from among halogen, $NH_2$, OH, CN, OMe, NHMe, $NMe_2$, $C_1$-$C_6$-alkyl and (CO)O $C_1$-$C_6$-alkyl.

Preparation Processes

The compounds of general formula (I) may be prepared according to the following synthesis schemes (Diagrams 1-5), wherein the substituents of general formula (I) have the above-mentioned meanings. These processes are intended as an illustration of the invention without restricting it to their content.

Diagram 1:

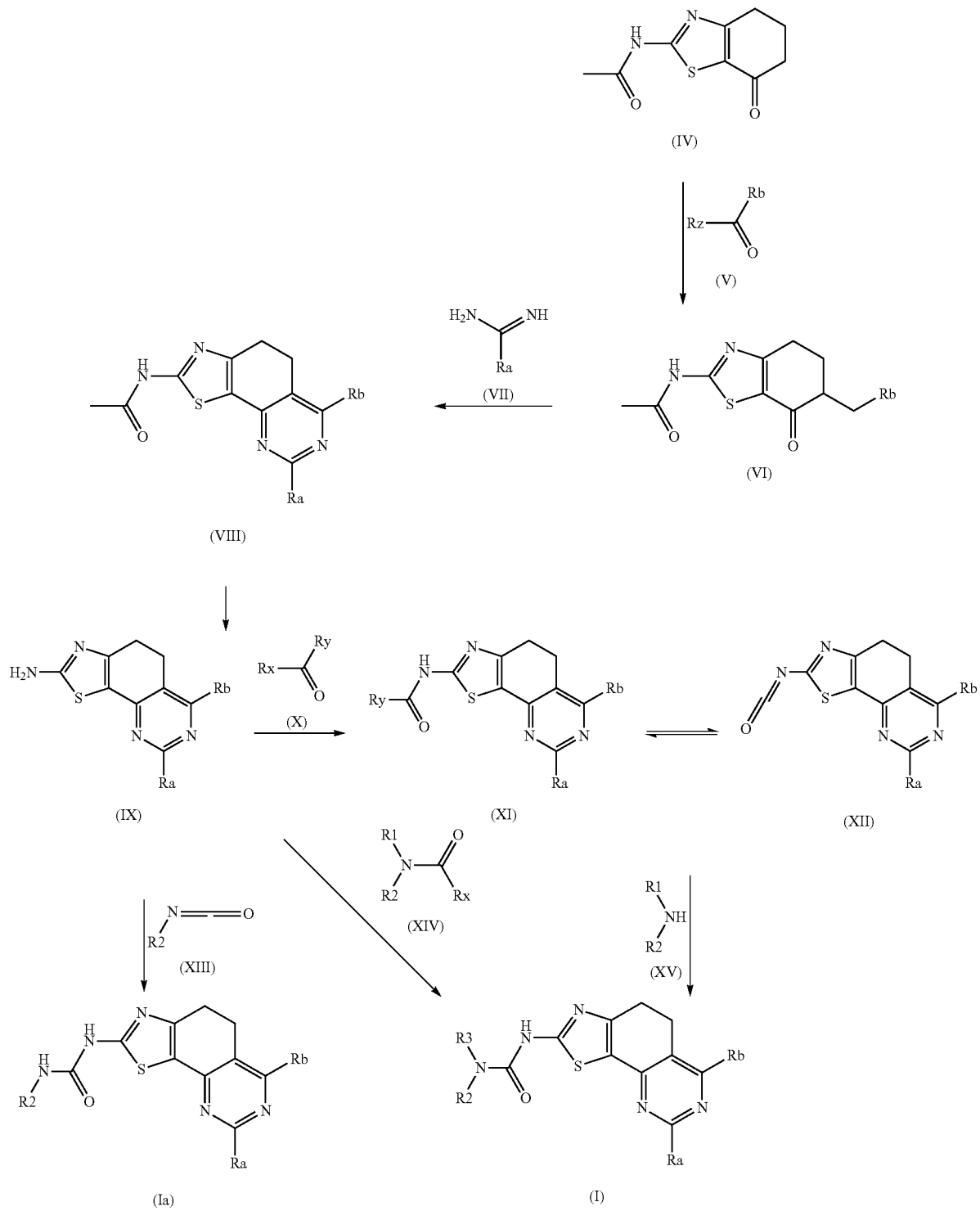

By deprotonation of the intermediate compound (IV) with a suitable base e.g. selected from, but not restricted to, the group comprising sodium methoxide, sodium ethoxide, lithium hexamethylsilazide, sodium hydride, it is converted with a suitable acylating reagent (V) into the intermediate compound (VI). Rb has the meaning given hereinbefore. Rz is a suitable leaving group e.g. selected from, but not restricted to, the group comprising halogen, S-alkyl, S-aryl, O-alkyl-sulphonyl, O-arylsulphonyl, O-alkyl, imidazole, O-hetaryl, O-acyl, O-aryl, wherein O-aryl may optionally be substituted by suitable electron-attracting groups (e.g. nitro). By reacting with a suitable amidine (VII) or one of the salts thereof the intermediate compound (VIII) is obtained. Ra has the meanings given hereinbefore. The compound thus obtained is then converted into the free aminothiazole (IX) by cleaving the acetyl group (e.g. by acidic or basic saponification or reaction with hydrazine hydrate). The reaction to obtain the ureas of general formula (I) or (Ia) is then carried out using one of the following methods: Direct reaction with a suitable isocyanate (XIII) leads directly to compounds of formula (Ia). Reaction with a suitable reagent (XIV) leads to compounds of formula (I), wherein Rx denotes a suitable leaving group selected from, for example, but not restricted to the group comprising halogen, S-alkyl, S-aryl O-alkylsulphonyl, O-arylsulphonyl, O-alkyl, imidazole, O-hetaryl, O-acyl, O-aryl, wherein O-aryl may optionally be substituted by suitable electron-attracting groups (e.g. nitro). Another possibility is to react the aminothiazole (IX) with a reagent of general formula (X) to obtain an activated intermediate compound (XI). Rx and Ry are identical or suitable leaving groups selected from, for example, but not restricted to the group comprising halogen, S-alkyl, S-aryl, O-alkylsulphonyl, O-arylsulphonyl, O-alkyl, imidazole, O-hetaryl, O-acyl, O-aryl, wherein O-aryl may optionally be substituted by durch suitable electron-attracting groups (e.g. nitro). Depending on the nature of the leaving group and the temperature, the intermediate compound (XI) is optionally in equilibrium with the isocyanate (XII), which may be formed by elimination of the leaving group Ry from (XI). The further reaction of the intermediate compound (XI), (XII) or a mixture of the two with suitable amines of general formula (XV) leads to the desired compounds of general formula (I). $R^1$ and $R^2$ have the meanings given hereinbefore.

Diagram 2:

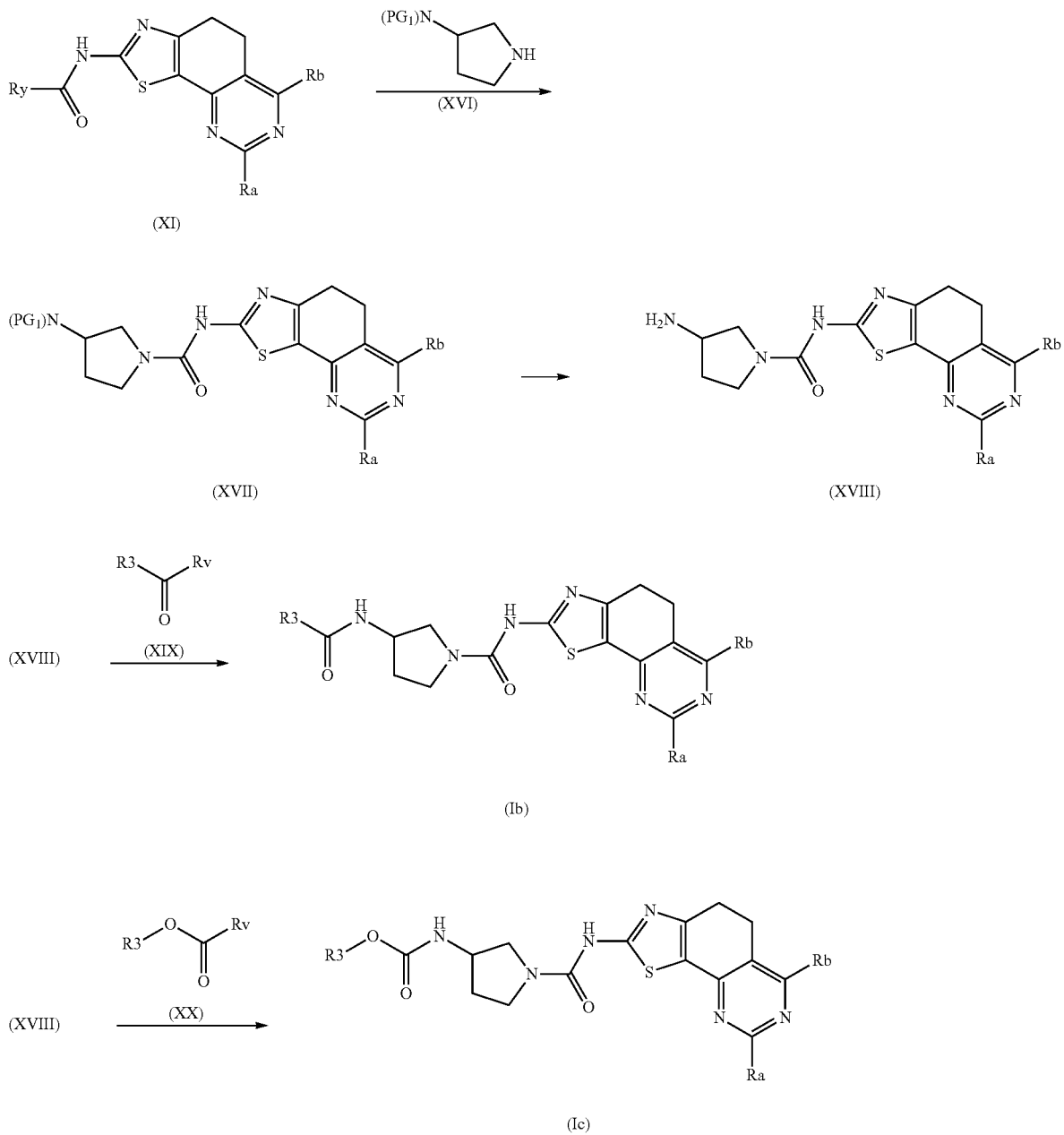

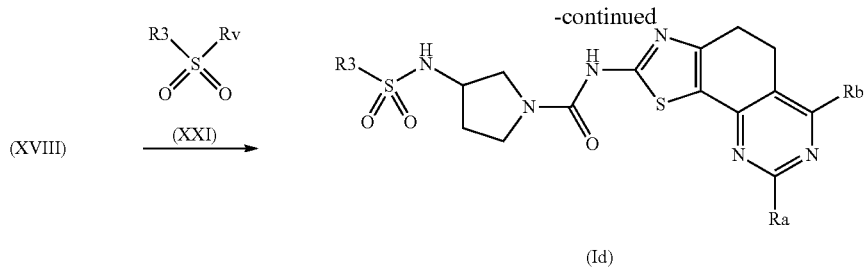

(Id)

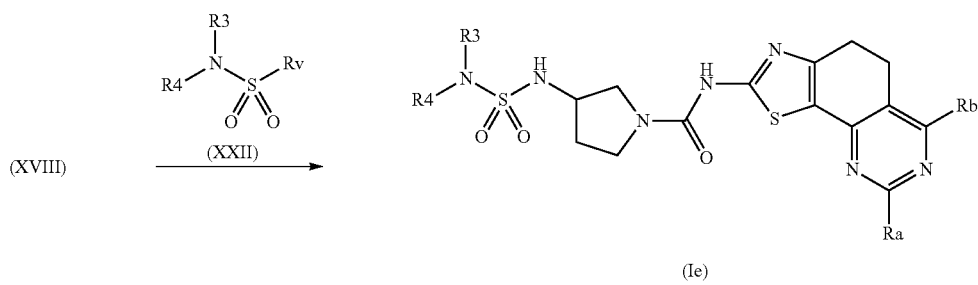

(Ie)

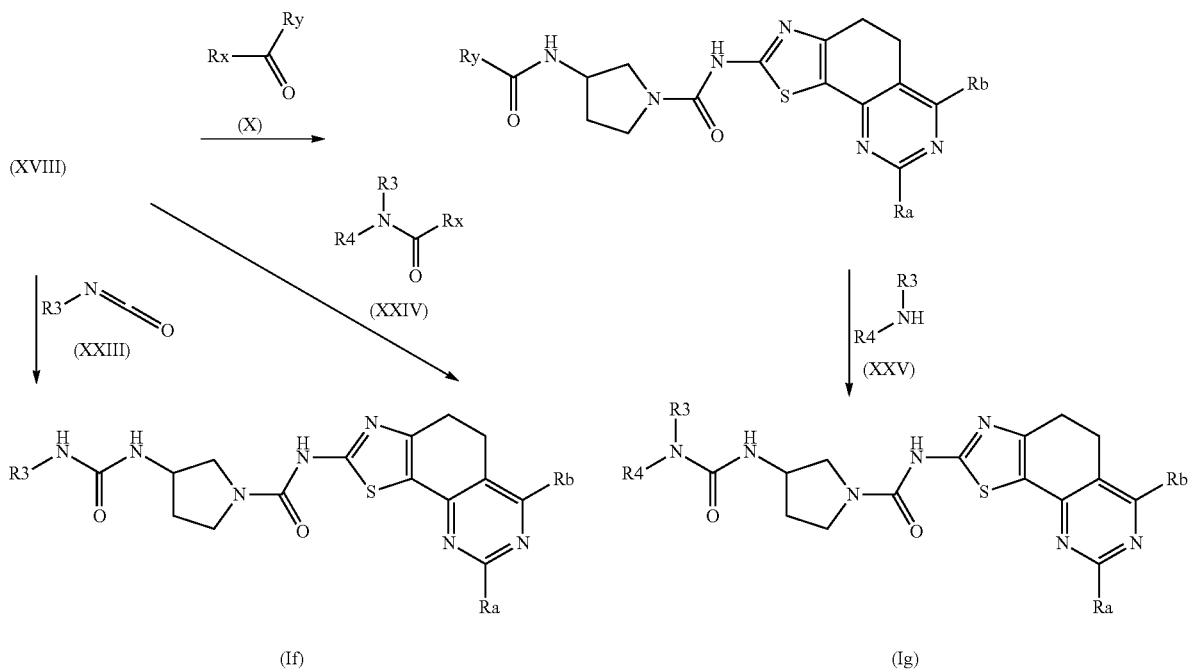

(If)                                                  (Ig)

By reacting the intermediate compound (XI) with a reagent of general formula (XVI), the intermediate compound (XVII) is obtained. PG1 is a suitable nitrogen-protective group selected from, for example, but not restricted to the group comprising alkylcarbonyl-(carbamate), phthalimides, benzyl (optionally substituted e.g. p-methoxybenzyl). The reagent (XVI) may be used as of one of the two possible enantiomers or as a racemate. After the protective group PG1 has been cleaved the intermediate compound (XVIII) is obtained. Reacting this intermediate compound with reagents of the type (XIX), (XX), (XXI), (XXII), (XXIII) or (XXIV) leads to the compounds (Ib), (Ic), (Id), (Ie), (If) or (Ig). $R^5$ and $R^6$ have the meanings described hereinbefore. Rx and Rv are suitable leaving groups selected from, for example, but not restricted to the group comprising halogen, S-alkyl, S-aryl O-alkylsulphonyl, O-arylsulphonyl, O-alkyl, imidazole, O-hetaryl, O-acyl, O-aryl, wherein O-aryl may optionally be substituted by suitable electron-attracting groups (e.g. nitro). Alternatively the compounds of general formula (Ig) may also be obtained, analogously to the method described in Diagram 1, by reacting the intermediate compound (XVIII) with the reagent of formula (X) described previously and subsequently reacting the intermediate compound (XXV) obtained with suitable amines of formula (XXV). $R^3$ and $R^4$ here also have the meanings described hereinbefore.

Diagram 3:

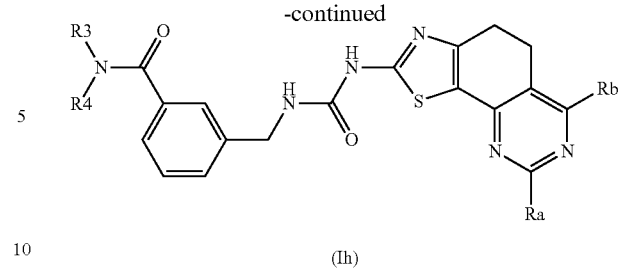
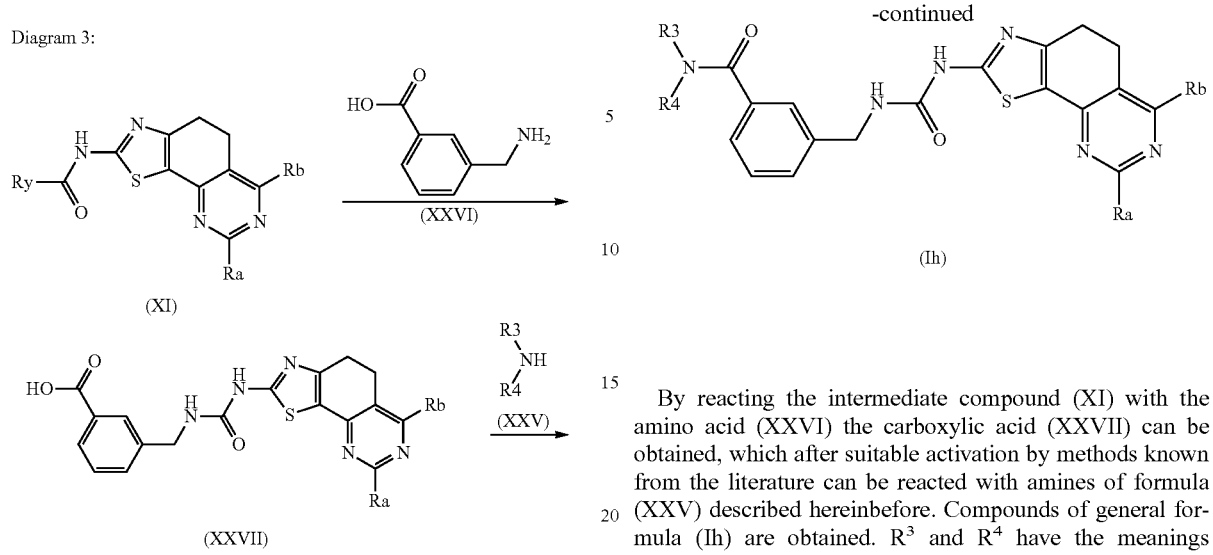

By reacting the intermediate compound (XI) with the amino acid (XXVI) the carboxylic acid (XXVII) can be obtained, which after suitable activation by methods known from the literature can be reacted with amines of formula (XXV) described hereinbefore. Compounds of general formula (Ih) are obtained. $R^3$ and $R^4$ have the meanings described hereinbefore.

Diagram 4:

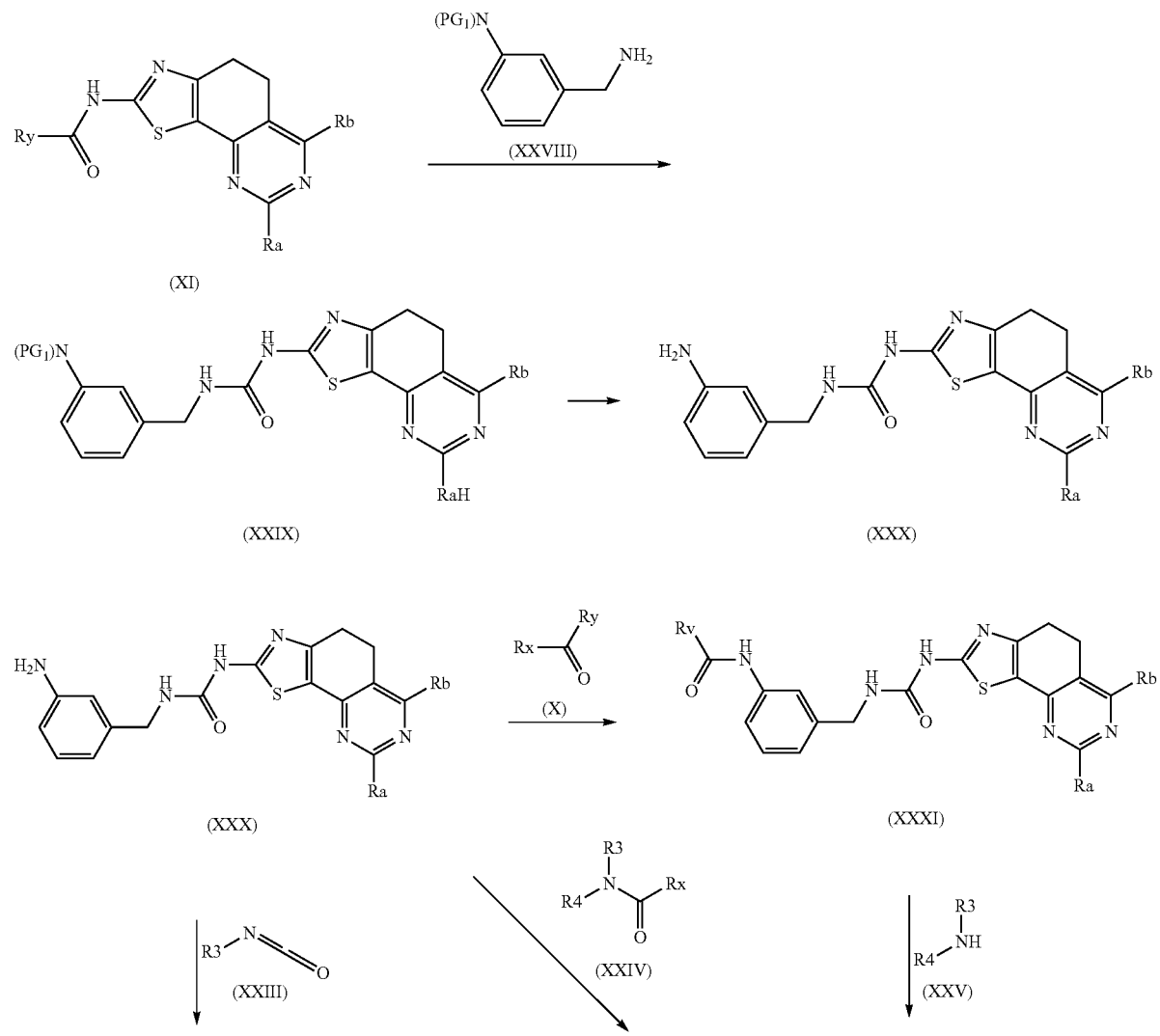

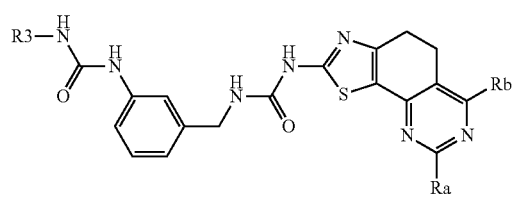

(Ii)

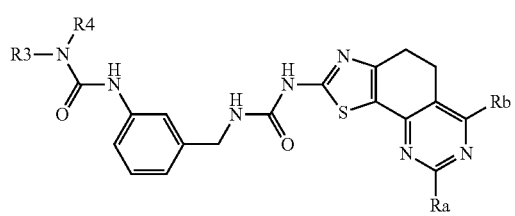

(Ij)

By reacting the intermediate compound (XI) with a reagent of formula (XXVIII) compounds of general formula (XXIX) are obtained. PG1 is a suitable nitrogen protecting group selected from, for example, but not restricted to the group comprising alkylcarbonyl-(carbamates), phthalimides, benzyl (optionally substituted e.g. p-methoxybenzyl). After the protective group PG1 has been cleaved the intermediate compound (XXX) may be obtained. Compounds of general formula (Ii) and (Ij) may be obtained by reacting this intermediate compound (XXX) with the reagents of formula (XXIII) or (XXIV) described hereinbefore. Alternatively the compounds of general formula (Ij) may also be obtained, analogously to the method described in Diagram 1, by reacting the intermediate compound (XXX) with the reagent of formula (X) described hereinbefore and subsequently reacting the intermediate compound (XXXI) obtained with suitable amines of formula (XXV). $R^3$ and $R^4$ here also have the meanings described hereinbefore. $R^5$ and $R^6$ have the meanings described hereinbefore.

Diagram 5:

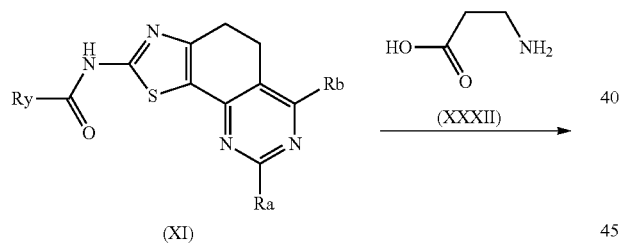

(XI)

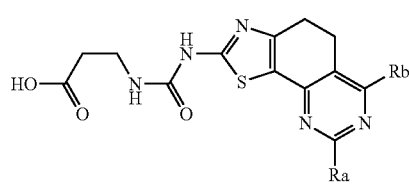 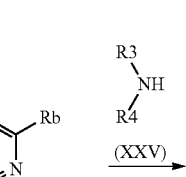

(XXXIII)

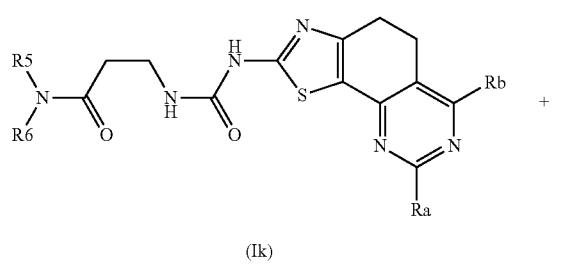

(Ik)

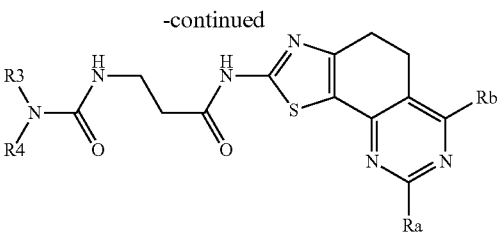

(XXXIV)

By reacting the intermediate compound (XI) with the amino acid (XXXII) the carboxylic acid (XXXIII) can be obtained, which after suitable activation can be reacted by methods known from the literature with amines of formula (XXV) described above. Compounds of general formula (Ik) are obtained as well as by-products of general formula (XXXIV). The latter can be separated from the desired products by chromatographic methods. $R^3$ and $R^4$ have the meanings described hereinbefore.

The new compounds of general formula (I) may be prepared analogously to the following Examples. The Examples described below are intended as an illustration of invention without restricting it.

Synthesis of the Reagents 2-chloro-3-fluoro-benzamidine (VII.1)

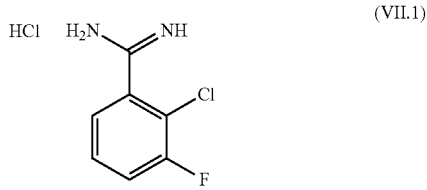 [SMILES: Cl ; N=C(N)c1cccc(F)c1Cl]

320 ml (0.32 mmol) of a 1 molar solution of lithium hexamethyl disilazide (LiHMDS) in hexane are placed in 800 ml diethyl ether and combined at ambient temperature with 25.0 g (0.161) 2-chloro-3-fluoro-benzonitrile. The mixture is stirred for 2 h at ambient temperature and after cooling to 0° C. it is combined with 280 ml 3 normal hydrochloric acid. The precipitate formed is suction filtered, washed with water and dried.

Yield: 16.5 g (49% of theory).

3-isopropyl-benzylamine hydrochloride (XV.1)

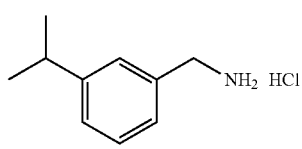

3-isopropyl-benzonitrile

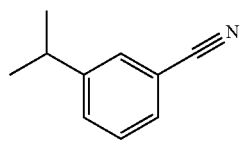

5.15 g (25.87 mmol) m-bromo-isopropyl-benzene and 2.69 g (30.04 mmol) copper cyanide are stirred in 2.50 ml of pyridine for 24 hours at 180° C. Then 15 ml of water, 15 ml of toluene and 15 ml conc. ammonia solution are added, then the mixture is extracted. The organic phase is dried and evaporated to dryness.

Yield: 5.00 g (100% of theoretical)

3-isopropyl-benzylamine hydrochloride (XV.1)

5.00 g (34.43 mmol) 3-isopropyl-benzonitrile and 5.00 g Raney nickel are hydrogenated in 500 ml methanolic ammonia solution for 8 hours at ambient temperature under a pressure of 50 psi. After the catalyst has been filtered off the mixture is evaporated down and the residue is precipitated as the hydrochloride.

Yield: 2.90 g (45% of theoretical)

Synthesis of the Reagent (XV.2)

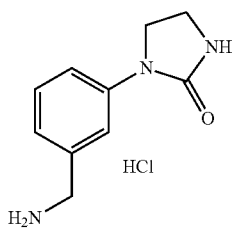

1-(2-chloro-ethyl)-3-(3-cyano-phenyl)-urea

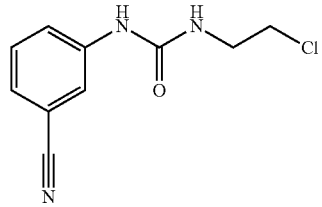 [SMILES: N#Cc1cccc(NC(=O)NCCCl)c1]

65.00 g (550 mmol) 3-amino-benzonitrile are dissolved in 450 ml dioxane, 56 ml (660 mmol) 1-chloro-2-isocyanato-ethane dissolved in 60 ml dioxane are added dropwise. The reaction mixture is stirred for 3 hours at 60° C. and for 16 hours at ambient temperature. Then the precipitate is suction filtered, washed with diethyl ether and dried.

Yield: 110.00 g (90% of theoretical)

mp: 138°-139° C.

3-(2-oxo-imidazolidin-1-yl)-benzonitrile

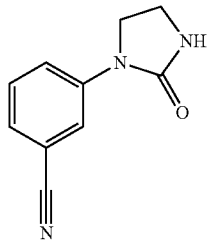 [SMILES: N#Cc1cccc(N2CCNC2=O)c1]

110.00 g (490 mmol) 1-(2-chloro-ethyl)-3-(3-cyano-phenyl)-urea are dissolved in 2000 ml of ethanol at 50° C. and a solution of 42.00 g (640 mmol) potassium hydroxide in 390 ml of ethanol is added within 1.5 hours. The reaction mixture is stirred for 16 hours at ambient temperature, then the precipitate formed is suction filtered, washed with water and dried.

Yield: 68.00 g (75% of theoretical)

mp: 149°-150° C.

1-(3-aminomethyl-phenyl)-imidazolidin-2-one hydrochloride (XV.2)

40.00 g (210 mmol) 3-(2-oxo-imidazolidin-1-yl)-benzonitrile are suspended in 1500 ml of methanol, 53 ml 37% hydrochloric acid are added. The mixture is hydrogenated for 20 hours at ambient temperature under a pressure of 7 bar with 4.00 g palladium/charcoal. The catalyst is filtered off, the filtrate is concentrated and the precipitate formed is suction filtered, washed with acetone and dried.

Yield: 42.00 g (88% of theoretical)

mp: 238°-239° C.

Synthesis of the Reagent (XV.3)

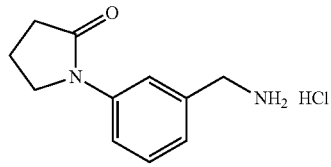

tert-butyl (3-amino-benzyl)-carbamate

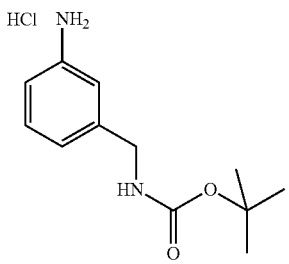 [SMILES: Cl ; CC(C)(C)OC(=O)NCc1cccc(N)c1]

9.35 g (76.49 mmol) 3-aminomethyl-phenylamine are dissolved in 200 ml dichloromethane and 100 ml of tetrahydrofuran, a solution of 17.03 g (78.02 mmol) Boc-anhydride in 200 ml dichloromethane is added dropwise. The mixture is stirred for 2.5 hours at ambient temperature, then evaporated down. The residue is precipitated as the hydrochloride.

Yield: 17.48 g (88% of theoretical)

tert-butyl 3-(4-chloro-butyrylamino)-benzyl]-carbamate

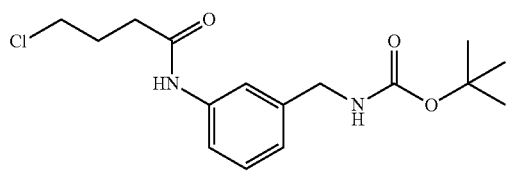 [SMILES: CC(C)(C)OC(=O)NCc1cccc(NC(=O)CCCCl)c1]

1.00 g (4.46 mmol) tert-butyl (3-amino-benzyl)-carbamate are liberated as the base, then placed in 40 ml chloroform, 1.20 ml (8.66 mmol) triethylamine and 0.50 ml (4.46 mmol) 4-chlorobutyryl chloride are added. The reaction mixture is stirred for 16 hours at ambient temperature, then extracted with chloroform and water and sodium carbonate solution. The organic phase is dried and evaporated to dryness.

Yield: 1.20 g (95% of theoretical)

tert-butyl [3-(2-oxo-pyrrolidin-1-yl)-benzyl]-carbamate

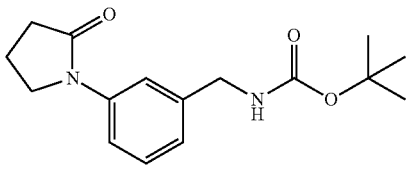 [SMILES: CC(C)(C)OC(=O)NCc1cccc(N2CCCC2=O)c1]

1.20 g (3.67 mmol) tert-butyl 3-(4-chloro-butyrylamino)-benzyl]-carbamate and 0.950 g (8.47 mmol) potassium tert-.butoxide are placed in 40 ml of tetrahydrofuran at 0° C. and stirred for 3 hours at ambient temperature. Then the reaction mixture is added to water and extracted with dichloromethane. The organic phase is dried and evaporated to dryness. The residue is purified by chromatography.

Yield: 0.500 g (47% of theoretical)

1-(3-aminomethyl-phenyl)-pyrrolidin-2-one hydrochloride (XV.3)

500 mg (1.72 mmol) tert-butyl [3-(2-oxo-pyrrolidin-1-yl)-benzyl]-carbamate are placed in 2 ml dichloromethane, 4.00 ml (8 mmol) 2 molar ethereal hydrochloric acid are added. The mixture is stirred for 16 hours at ambient temperature, then evaporated down. The residue is crystallised with acetone/ethanol and diethyl ether.

Yield: 220 mg (56% d. Th)

Synthesis of the Reagent (XV.4)

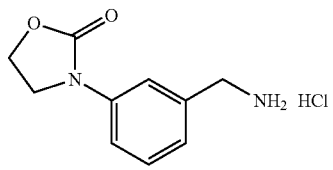

2-chloro-ethyl [3-(tert-butoxycarbonylamino-methyl)-phenyl]-carbamate

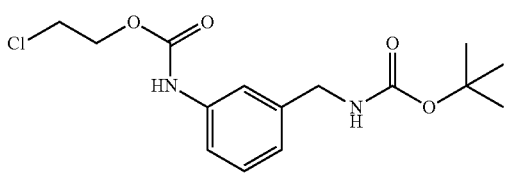 [SMILES: CC(C)(C)OC(=O)NCc1cccc(NC(=O)OCCCl)c1]

900 mg g (3.48 mmol) tert-butyl 3-amino-benzyl)-carbamate are liberated as the base, then placed in 40 ml of tetrahydrofuran, and 1.11 ml (8 mmol) triethylamine and 0.75 ml (6.82 mmol) 2-chloroethylchloroformate are added. The reaction mixture is stirred for 16 hours at ambient temperature, then extracted with dichloromethane and water. The organic phase is separated off using a phase separation cartridge and evaporated to dryness.

Yield: 1.20 g (100% of theoretical)

tert-butyl [3-(2-oxo-oxazolidin-3-yl)-benzyl]-carbamate

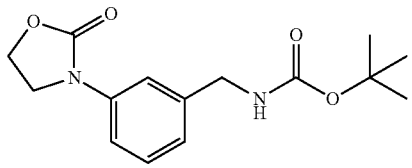 [SMILES: CC(C)(C)OC(=O)NCc1cccc(N2CCOC2=O)c1]

1.20 g (3.65 mmol) 2-chloro-ethyl [3-(tert-butoxycarbonylamino-methyl)-phenyl]-carbamate and 0.850 g (7.58 mmol) potassium tert.butoxide are placed at 0° C. in 30 ml of tetrahydrofuran and the mixture is stirred for 3 hours at ambient temperature. Then the reaction mixture is added to water and extracted with dichloromethane. The organic phase is dried and evaporated to dryness. The residue is purified by chromatography.

Yield: 0.250 g (23% of theoretical)

3-(3-aminomethyl-phenyl)-oxazolidin-2-one hydrochloride (XV.4)

380 mg (1.30 mmol) tert-butyl [3-(2-oxo-oxazolidin-3-yl)-benzyl]-carbamate are placed in 2 ml dichloromethane, 4.00 ml (8 mmol) 2 molar ethereal hydrochloric acid are added. The mixture is stirred for 16 hours at ambient temperature, then evaporated down. The residue is lyophilised.

Yield: 300 mg (100% of theoretical)

Synthesis of the Reagent (XV.5)

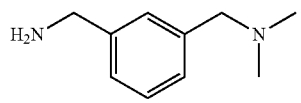 (XV.5)

3-dimethylaminomethyl-benzonitrile

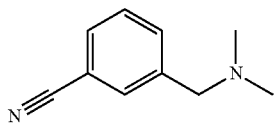

5.00 g (37.37 mmol) 3-cyanobenzaldehyde and 20.00 ml (40 mmol) dimethylamine (2 molar solution in tetrahydrofuran) are placed in 150 ml of tetrahydrofuran and cooled to 0° C. 12.40 g (81.73 mmol) sodium triacetoxyborohydride are added, then the mixture is stirred for 2 hours at 0° C. and 2 hours at ambient temperature. The reaction mixture is combined with 25 ml of 15% potassium carbonate solution and stirred for 0.5 hours. After the addition of ethyl acetate the mixture is extracted. The organic phase is washed with potassium carbonate solution, dried and evaporated to dryness.

Yield: 7.00 g (94% of theoretical)

3-dimethylaminomethyl-benzylamine (XV.5)

7.00 g (34.95 mmol) 3-dimethylaminomethyl-benzonitrile are placed in 100 ml of methanolic ammonia solution and hydrogenated with 1.40 g Raney nickel at ambient temperature under a pressure of 3 bar. The catalyst is suction filtered, the filtrate is evaporated down. The residue is purified by chromatography.

Yield: 2.40 g (42% of theoretical)

Synthesis of the Reagent (XV.6)

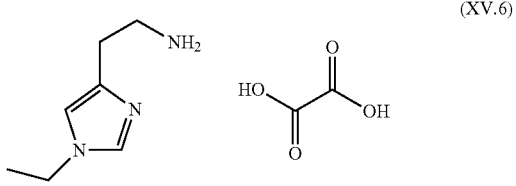 (XV.6)

7,8-dihydro-6H-imidazo[1,5-c]pyrimidin-5-one

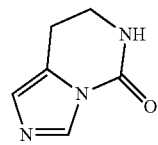

50.00 g (450 mmol) histamine are dissolved in 1500 ml dimethylformamide, 73.87 g (450 mmol) carbonyldiimidazole are added. The reaction mixture is stirred for 5 hours at 70° C. and for 16 hours at ambient temperature. Then it is evaporated down, and the residue is extracted hot from acetonitrile.

Yield: 53.73 g (87% of theoretical)

2-ethyl-5-oxo-5,6,7,8-tetrahydro-imidazo[1,5-c]pyrimidin-2-ium; bromide

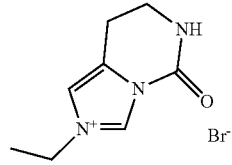

1.00 g (7 mmol) 7,8-dihydro-6H-imidazo[1,5-c]pyrimidin-5-one and 1.57 ml (21 mmol) ethylbromide are stirred in 12 ml acetonitrile for 16 hours at 80° C. After cooling the suspension is suction filtered, washed and dried.

Yield: 1.40 g (78% of theoretical)

2-(1-ethyl-1H-imidazol-4-yl)-ethylamine oxalate (XV.6)

1.16 g (5 mmol) 2-ethyl-5-oxo-5,6,7,8-tetrahydro-imidazo[1,5-c]pyrimidin-2-ium; bromide are refluxed in 7 ml (14 mmol) 2 molar hydrochloric acid for 16 hours with stirring. Then the mixture is evaporated down, the residue is recrystallised from acetonitrile/ethanol. The very hygroscopic crystals obtained are made neutral and evaporated down. The residue is precipitated as the oxalate and recrystallised from ethanol.

Yield: 1.00 g (93% of theoretical)

Synthesis of the Reagent (XV.7)

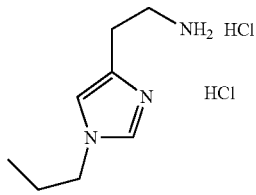

5-oxo-2-propyl-5,6,7,8-tetrahydro-imidazo[1,5-c]
pyrimidin-2-ium; bromide

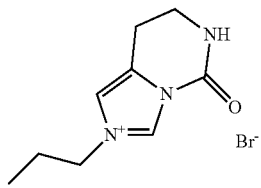

2.00 g (15 mmol) 7,8-dihydro-6H-imidazo[1,5-c]pyrimidin-5-one and 6.83 mmol) (75 mmol) propylbromide are stirred in 20 ml acetonitrile for 72 hours at 85° C. After cooling the suspension is suction filtered, washed and dried.

Yield: 3.48 g 2-(1-propyl-1H-imidazol-4-yl)-ethylamine (XV.7)

100 mg (0.384 mmol) 5-oxo-2-propyl-5,6,7,8-tetrahydro-imidazo[1,5-c]pyrimidin-2-ium; bromide are refluxed in 192 μl (1.15 mmol) 6 molar hydrochloric acid for 16 hours with stirring. Then the solution is lyophilised.

Yield: 81.30 mg (64% of theoretical)

Synthesis of the Reagent (XV.8)

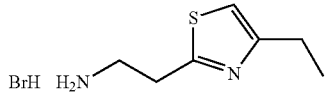

2-(4-ethyl-thiazol-2-yl)-ethylamine hydrobromide
(XV.8)

2.00 g (9.50 mmol) tert.butyl N(3-amino-3-thioxopropyl)carbamate and 1.58 g (10.45 mmol) 1-bromo-2-butanone are refluxed in 40 ml of ethanol for 16 hours with stirring. The reaction mixture is evaporated down, the residue is purified by chromatography.

Yield: 2.00 g (89% of theoretical)

Synthesis of the Reagent (XV.9)

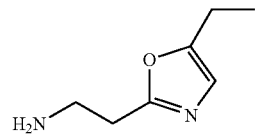

benzyl
[2-(2-hydroxy-butylcarbamoyl)-ethyl]-carbamate

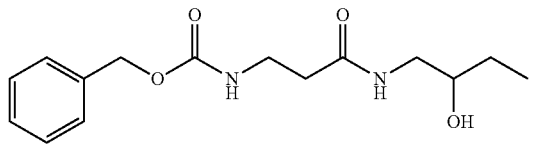 [SMILES: CCC(O)CNC(=O)CCNC(=O)OCc1ccccc1]

23.20 g (103.93 mmol) 3-benzyloxycarbonylamino-propionic acid, 14.10 g (104.35 mmol) 1-hydroxybenzotriazole, 18.80 ml (135.07 mmol) triethylamine and 21.00 g (135.27 mmol) (ethyl-3-(3-dimethylamino)-propylcarbondiimide hydrochloride (EDAC) are placed in 150 ml dichloromethane, cooled to 0° C. and stirred for 0.75 hours at this temperature. Then 10.50 g (114.26 mmol) 1-amino-2-butanol are added, the mixture is stirred for 2.5 hours at 0°-5° C. The reaction mixture is extracted with water and 1 molar sodium carbonate solution, the organic phase is dried and evaporated to dryness. The residue is extracted again with dichloromethane and sodium carbonate solution.

Yield: 12.30 g (40% of theoretical)

benzyl [2-(2-oxo-butylcarbamoyl)-ethyl]-carbamate

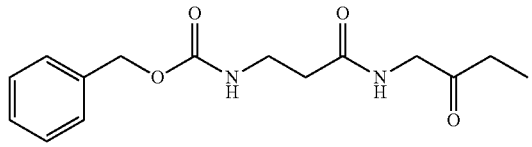 [SMILES: CCC(=O)CNC(=O)CCNC(=O)OCc1ccccc1]

2.20 ml (26.05 mmol) oxalyl chloride are placed in 10 ml dichloromethane, the solution is cooled to −53° C. 2.45 ml (34.49 mmol) dimethylsulphoxide in 5 ml dichloromethane are slowly added dropwise, the mixture is stirred for 0.25 hours, then a solution of 6.30 g (21.40 mmol) benzyl [2-(2-hydroxy-butylcarbamoyl)-ethyl]-carbamate in 30 ml dichloromethane is added. The mixture is stirred for 1.5 hours at −60° C., then 12.60 ml triethylamine are added dropwise. The suspension is stirred for 1 hour at −50° C., then within 16 hours allowed to come up to ambient temperature. The reaction mixture is diluted with dichloromethane and extracted with 1 molar hydrochloric acid, 1 molar sodium carbonate solution and water. The organic phase is dried and evaporated to dryness.

Yield: 5.82 g (93% of theoretical)

benzyl [2-(5-ethyl-oxazol-2-yl)-ethyl]-carbamate

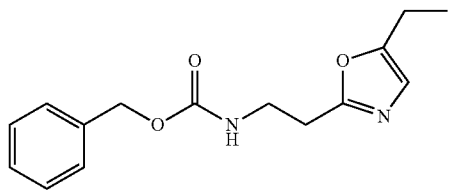 [SMILES: CCc1cnc(CCNC(=O)OCc2ccccc2)o1]

23.07 g (49.60 mmol) PS-triphenylphosphine are suspended in 200 ml dichloromethane, 12.65 g (49.82 mmol) iodine are added. The mixture is stirred for 0.1 hours at ambient temperature, then 13.80 ml (99.28 mmol) triethylamine are added dropwise. 5.80 g (19.84 mmol) benzyl [2-(2-oxo-butylcarbamoyl)-ethyl]-carbamate dissolved in 150 ml dichloromethane are added. The reaction mixture is stirred for 72 hours at ambient temperature, then the precipitate is filtered off. The filtrate is extracted with water, the organic phase is dried and evaporated to dryness.
Yield: 3.35 g (31% of theoretical)

2-(5-ethyl-oxazol-2-yl)-ethylamine (XV.9)

2.86 g (10.43 mmol) benzyl [2-(5-ethyl-oxazol-2-yl)-ethyl]-carbamate are placed in 130 ml of methanol, 0.910 mg palladium/charcoal 10% are added, then the mixture is hydrogenated for 5 hours at ambient temperature under a pressure of 14 psi. Then the catalyst is suction filtered and the solution is evaporated down.
Yield: 1.45 g (99% of theoretical)
Synthesis of the Reagent (XV.10)

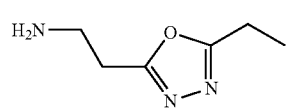 (XV.10)

tert-butyl [3-oxo-3-(N'-propionyl-hydrazino)-propyl]-carbamate

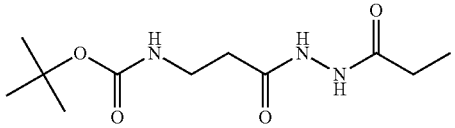 [SMILES: CCC(=O)NNC(=O)CCNC(=O)OC(C)(C)C]

25.00 g (132 mmol) 3-tert-butoxycarbonylamino-propionic acid, 11.45 g (130 mmol) ethanoic acid hydrazide, 50.91 g (159 mmol) O-(1H-benzotriazol-1-yl)-N,N,N',N'-tetramethyluronium tetrafluoroborate (TBTU) and 50 ml diisopropylethylamine are stirred in 500 ml of tetrahydrofuran/dichloromethane for 24 hours at ambient temperature. Then the mixture is evaporated down, the residue is extracted with ethyl acetate and 10% potassium hydrogen carbonate solution. The organic phase is dried and evaporated to dryness. The residue is crystallised from isopropylether.
Yield: 3.20 g (9% of theoretical)

tert-butyl [2-(5-ethyl-[1,3,4]oxadiazol-2-yl)-ethyl]-carbamate

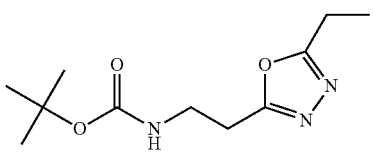

11.49 g (24.70 mmol) PS-triphenylphosphine are placed in 240 ml dichloromethane, 6.27 g (24.70 mmol) iodine are added. The mixture is stirred for 0.1 hours at ambient temperature, then 7.00 ml (50.50 mmol) triethylamine are added dropwise. 3.20 g (12.34 mmol) tert-butyl [3-oxo-3-(N'-propionyl-hydrazino)-propyl]-carbamate dissolved in 150 ml dichloromethane are added. The reaction mixture is stirred for 24 hours at ambient temperature, then the precipitate is filtered off. The filtrate is evaporated down and purified by chromatography.
Yield: 2.95 g (99% of theoretical)

2-(5-ethyl-[1,3,4]oxadiazol-2-yl)-ethylamine (XV.10)

2.95 g (12.23 mmol) tert-butyl [2-(5-ethyl-[1,3,4]oxadiazol-2-yl)-ethyl]-carbamate and 10 ml trifluoroacetic acid are stirred in 100 ml dichloromethane for 24 hours at ambient temperature. Then the mixture is evaporated down, the residue is made basic and extracted with ethyl acetate. The organic phase is dried and evaporated to dryness.
Yield: 0.410 g (24% of theoretical)
Synthesis of the Reagent (XV.11)

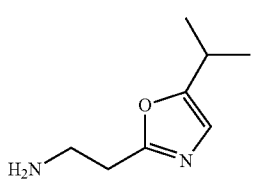 (XV.11)

benzyl [2-(2-hydroxy-3-methyl-butylcarbamoyl)-ethyl]-carbamate

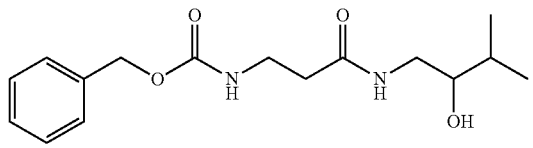 [SMILES: CC(C)C(O)CNC(=O)CCNC(=O)OCc1ccccc1]

46.00 g (206.07 mmol) 3-benzyloxycarbonylamino-propionic acid, 51.37 g (267.95 mmol) 1-(3-dimethylaminopropyl)-3-ethylcarbodiimide hydrochloride, 27.85 g (206.07 mmol) hydroxybenzotriazole (HOBT) and 37.14 ml (267.95 mmol) triethylamine are placed in 700 ml dichloromethane, the mixture is stirred for 0.5 hours at 0°, then 23.70 g (229.73 mmol) 1-amino-3-methyl-butan-2-ol are added. The reaction mixture is stirred for 16 hours at ambient temperature. Then it is extracted with potassium carbonate solution and dichloromethane. The organic phase is washed with 1 molar sodium hydroxide solution, dried and evaporated to dryness. The residue is extracted with diethyl ether, then recrystallised with acetonitrile.

Yield: 32.40 g (51% of theoretical)

benzyl [2-(3-methyl-2-oxo-butylcarbamoyl)-ethyl]-carbamate

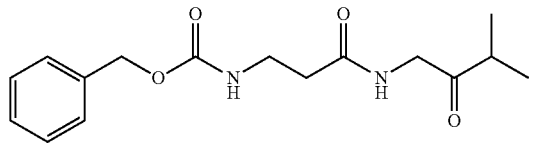 [SMILES: CC(C)C(=O)CNC(=O)CCNC(=O)OCc1ccccc1]

10.81 ml (126.08 mmol) oxalyl chloride are placed in 300 ml dichloromethane and cooled to −70° C. 11.94 ml (168.11 mmol) dimethylsulphoxide are slowly added dropwise. The mixture is stirred for 0.1 hours, then 32.40 g (105.07 mmol) benzyl [2-(2-hydroxy-3-methyl-butylcarbamoyl)-ethyl]-carbamate in 70 ml dichloromethane are added. The mixture is stirred for 1 hour, then 62.48 ml (450.72 mmol) triethylamine are added dropwise. The reaction mixture is stirred for 1.5 hours at −70° C., then slowly allowed to come up to ambient temperature. It is diluted with dichloromethane and washed with 1 molar hydrochloric acid, saturated sodium carbonate solution, water and saturated sodium chloride solution. The organic phase is dried and evaporated to dryness.

Yield: 30.80 g (96% of theoretical)

benzyl [2-(5-isopropyl-oxazol-2-yl)-ethyl]-carbamate

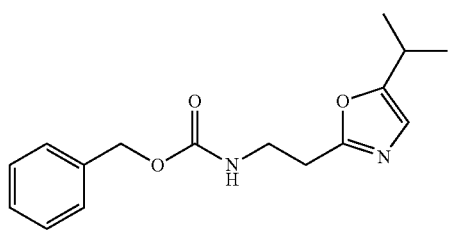 [SMILES: CC(C)c1cnc(CCNC(=O)OCc2ccccc2)o1]

100.00 g (215 mmol) PS-triphenylphosphine are suspended in 1000 ml dichloromethane, 59.92 g (236.06 mmol) iodine are added. The mixture is stirred for 0.1 hours at ambient temperature, then 65.32 ml (470.24 mmol) triethylamine are added dropwise. 28.80 g (94.91 mmol) benzyl [2-(3-methyl-2-oxo-butylcarbamoyl)-ethyl]-carbamate dissolved in 200 ml dichloromethane are added. The reaction mixture is stirred for 16 hours at ambient temperature. If the reaction is incomplete, a further 0.1 eq triphenylphosphine and 0.1 eq iodine are added. The mixture is stirred for 16 hours at ambient temperature, then the precipitate is filtered off. The filtrate is evaporated down, the residue is extracted with water and chloroform, the organic phase is dried and evaporated to dryness. The residue is purified by chromatography.

Yield: 12.50 g (46% of theoretical)

2-(5-isopropyl-oxazol-2-yl)-ethylamine (XV.11)

6.50 g (22.54 mmol) benzyl [2-(5-isopropyl-oxazol-2-yl)-ethyl]-carbamate are placed in 130 ml of methanol, 3.50 g of 10% palladium/charcoal are added, then the mixture is hydrogenated for 5 hours at ambient temperature under a pressure of 14 psi. Then the catalyst is removed by suction filtering and the solution is evaporated down. The residue is extracted with dichloromethane and potassium carbonate solution, the organic phase is dried and evaporated to dryness.

Yield: 3.20 g (92% of theoretical)

Synthesis of the Reagent (XV.12)

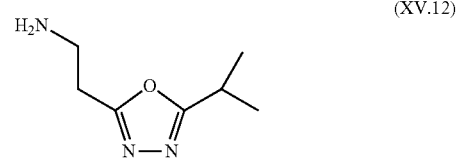

(XV.12)

tert-butyl [3-(N'-isobutyryl-hydrazino)-3-oxo-propyl]-carbamate

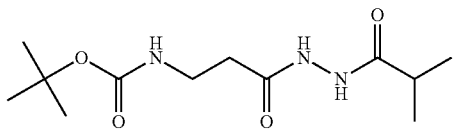 [SMILES: CC(C)C(=O)NNC(=O)CCNC(=O)OC(C)(C)C]

25.00 g (132 mmol) 3-tert-butoxycarbonylamino-propionic acid, 13.50 g (132 mmol) isobutyric acid hydrazide, 50.91 g (159 mmol) O-(1H-benzotriazol-1-yl)-N,N,N',N'-tetramethyluronium tetrafluoroborate (TBTU) and 50 ml diisopropylethylamine are stirred in 500 ml of tetrahydrofuran/dichloromethane for 24 hours at ambient temperature. Then the mixture is evaporated down, the residue is extracted with ethyl acetate and 10% potassium hydrogen carbonate solution. The organic phase is dried and evaporated to dryness. The residue is crystallised from toluene/isopropylether.

Yield: 16.55 g (46% of theoretical)

tert-butyl [2-(5-isopropyl-[1,3,4]oxadiazol-2-yl)-ethyl]-carbamate

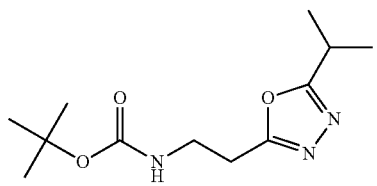 [SMILES: CC(C)c1nnc(CCNC(=O)OC(C)(C)C)o1]

20.00 g (43.00 mmol) PS-triphenylphosphine are placed in 240 ml dichloromethane, 10.88 g (42.87 mmol) iodine are added. The mixture is stirred for 0.1 hours at ambient temperature, then 12.10 ml (87.29 mmol) triethylamine are added dropwise. 5.83 g (21.33 mmol) tert-butyl [3-(N'-isobutyryl-hydrazino)-3-oxo-propyl]-carbamate dissolved in 150 ml dichloromethane are added. The reaction mixture is stirred for 24 hours at ambient temperature, then the precipitate is filtered off. The filtrate is evaporated down and purified by chromatography.

Yield: 5.40 g (99% of theoretical)

2-(5-isopropyl-[1,3,4]oxadiazol-2-yl)-ethylamine (XV.12)

4.00 g (15.67 mmol) tert-butyl [2-(5-isopropyl-[1,3,4]oxadiazol-2-yl)-ethyl]-carbamate and 20 ml trifluoroacetic acid are stirred in 200 ml dichloromethane for 24 hours at ambient temperature. Then the mixture is evaporated down, the residue is made basic and extracted with ethyl acetate. The organic phase is dried and evaporated to dryness.

Yield: 1.440 g (59% of theoretical)

Synthesis of the Reagent (XV.13)

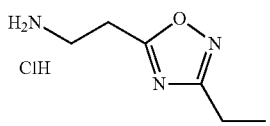

methyl 3-tert-butoxycarbonylamino-propionate

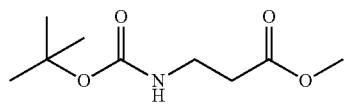

9.90 g (70.93 mmol) β-alaninemethylester hydrochloride are placed in 200 ml acetonitrile, 10 ml (72.14 mmol) triethylamine are added. The mixture is stirred for 0.3 hours at ambient temperature, and first 15.48 g (70.93 mmol) Boc-anhydride, then 1.65 g (7.09 mmol) Zirkon(IV) chloride are added. The reaction mixture is stirred for 2 hours at ambient temperature, then evaporated down. The residue is extracted with ethyl acetate and water. The organic phase is dried and evaporated to dryness.

Yield: 12.50 g (87% of theoretical)

N-hydroxy-propionamidine

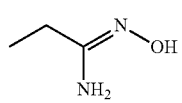

8.00 g (57.88 mmol) potassium carbonate are dissolved in 25 ml of water, 80 ml of ethanol, 4.00 g (57.56 mmol) hydroxylamine and 4.11 ml (57.56 mmol) propionitrile are added. The reaction mixture is stirred for 18 hours at ambient temperature, then evaporated down, and re-evaporated with toluene. The residue is combined with ethanol, suction filtered and the filtrate is evaporated to dryness. Yield: 3.70 g (73% of theoretical)

tert-butyl [2-(3-ethyl-[1,2,4]oxadiazol-5-yl)-ethyl]-carbamate

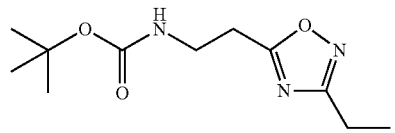 [SMILES: CCc1noc(CCNC(=O)OC(C)(C)C)n1]

2.00 g (22.70 mmol) N-hydroxy-propionamidine are placed in 10 ml dimethylformamide and molecular sieve. 0.999 g (24.97 mmol) sodium hydride (60% in mineral oil) are added. The mixture is stirred for 0.1 hours at 50° C., then 5.00 g (24.60 mmol) methyl3-tert-butoxycarbonylamino-propionate in 20 ml dimethylformamide are added. The reaction mixture is stirred for 3 hours at 50° C. After cooling 15 ml of water are added, and the mixture is suction filtered through Celite. The 2 phases of the filtrate are separated and the organic phase is evaporated down. The residue is purified by chromatography.

Yield: 2.05 g (37% of theoretical)

2-(3-ethyl-[1,2,4]oxadiazol-5-yl)-ethylamine hydrochloride (XV.13)

2.05 g (8.50 mmol) tert-butyl [2-(3-ethyl-[1,2,4]oxadiazol-5-yl)-ethyl]-carbamate are placed in 20 ml dichloromethane and 40 ml of 1 molar ethereal hydrochloric acid are added. The reaction mixture is stirred for 16 hours at ambient temperature and 4 hours at 40° C. After the addition of a further 10 ml ethereal hydrochloric acid stirring is continued for 72 hours at ambient temperature. The suspension is evaporated down.

Yield: 1.50 g (99% of theoretical)

Synthesis of the Reagent (XV.14)

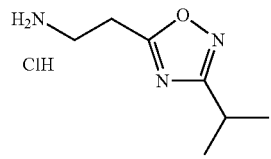

N-hydroxy-isobutyramidine

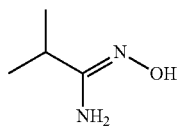

6.00 g (43.41 mmol) potassium carbonate are dissolved in 19 ml of water, 60 ml of ethanol, 3.00 g (43.17 mmol) hydroxylamine and 3.95 ml (43.44 mmol) isobutyronitrile are added. The reaction mixture is stirred for 18 hours at ambient temperature, then evaporated down, and re-evaporated with toluene. The residue is mixed with ethanol, suction filtered and the filtrate is evaporated to dryness.

Yield: 3.70 g (84% of theoretical)

tert-butyl [2-(3-isopropyl-[1,2,4]oxadiazol-5-yl)-ethyl]-carbamate

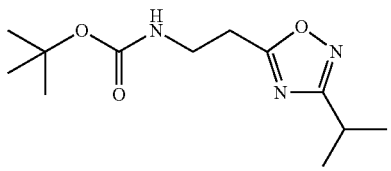 [SMILES: CC(C)c1noc(CCNC(=O)OC(C)(C)C)n1]

2.20 g (21.54 mmol) N-hydroxy-isobutyramidine are placed in 10 ml dimethylformamide and molecular sieve. 0.948 g (23.69 mmol) sodium hydride (60% in mineral oil) are added. The mixture is stirred for 0.1 hours at 50° C., then 6.20 g (30.51 mmol) methyl 3-tert-butoxycarbonylamino-propionate in 20 ml dimethylformamide are added. The reaction mixture is stirred for 3 hours at 50° C. After cooling 15 ml of water are added and the mixture is suction filtered through Celite. The 2 phases of the filtrate are separated, the aqueous phase is extracted with ethyl acetate, the combined organic phases are evaporated down. The residue is purified by chromatography.

Yield: 0.900 g (16% of theoretical)

2-(3-isopropyl-[1,2,4]oxadiazol-5-yl)-ethylamine hydrochloride (XV.14)

900 mg (3.53 mmol) tert-butyl [2-(3-isopropyl-[1,2,4]oxa-diazol-5-yl)-ethyl]-carbamate are placed in 10 ml dichloromethane, 20 ml 1 molar ethereal hydrochloric acid are added. The reaction mixture is stirred for 16 hours at ambient temperature. After the further addition of 10 ml ethereal hydrochloric acid the mixture is stirred for another 72 hours at ambient temperature and 4 hours at 40° C. The suspension is evaporated down. The residue is dissolved in acetone, mixed with diethyl ether and suction filtered.

Yield: 530 mg (78% of theoretical)

Synthesis of the Reagent (XV.15)

(XV.15)

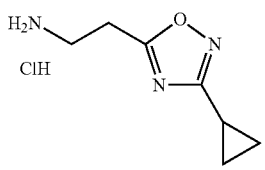

ethyl 3-tert-butoxycarbonylamino-propionate

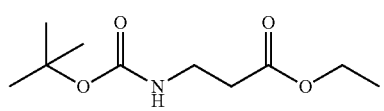

5.00 g (32.55 mmol) β-alanine ethyl ester hydrochloride are placed in 100 ml acetonitrile, 4.75 ml (34.27 mmol) triethylamine are added. The mixture is stirred for 0.3 hours at ambient temperature, and first 7.30 g (33.45 mmol) Boc-anhydride, then 0.759 g (3.26 mmol) zirconium(IV) chloride are added. The reaction mixture is stirred for 2 hours at ambient temperature, then evaporated down. The residue is extracted with ethyl acetate and water. The organic phase is dried and evaporated to dryness.

Yield: 7.50 g (100% of theoretical)

N-hydroxy-cyclopropanecarboxamidine

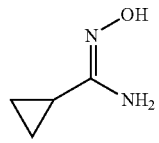

6.00 g (43.41 mmol) potassium carbonate are dissolved in 19 ml of water, 60 ml of ethanol, 3.00 g (43.17 mmol) hydroxylamine and 3.25 ml (43.25 mmol) cyclopropylcyanide are added. The reaction mixture is stirred for 18 hours at ambient temperature, then evaporated down and re-evaporated with toluene. The residue is mixed with ethanol, suction filtered and the filtrate is evaporated to dryness.

Yield: 3.47 g (80% of theoretical)

tert-butyl [2-(3-cyclopropyl-[1,2,4]oxadiazol-5-yl)-ethyl]-carbamate

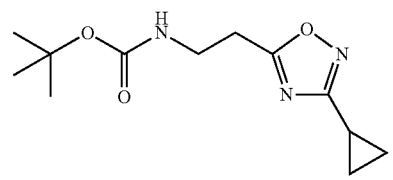 [SMILES: CC(C)(C)OC(=O)NCCc1nc(C2CC2)no1]

3.10 g (30.96 mmol) N-hydroxy-cyclopropanecarboxamidine are placed in 10 ml dimethylformamide and molecular sieve. 1.32 g (34.06 mmol) sodium hydride (60% in mineral oil) are added. The mixture is stirred for 0.1 hours at 50° C., then 7.40 g (34.06 mmol) ethyl 3-tert-butoxycarbonylamino-propionate in 20 ml dimethylformamide are added. The reaction mixture is stirred for 3 hours at 50° C. After cooling 15 ml of water are added, the mixture is suction filtered through Celite. The 2 phases of the filtrate are separated, the aqueous phase is extracted with ethyl acetate, the combined organic phase is evaporated down. The residue is purified by chromatography.

Yield: 4.00 g (51% of theoretical)

2-(3-cyclopropyl-[1,2,4]oxadiazol-5-yl)-ethylamine hydrochloride (XV.15)

4.00 g (15.79 mmol) tert-butyl [2-(3-cyclopropyl-[1,2,4]oxadiazol-5-yl)-ethyl]-carbamate are placed in 40 ml dichloromethane, 80 ml 1 molar ethereal hydrochloric acid are added. The reaction mixture is stirred for 3 hours at reflux temperature and for 72 hours at ambient temperature, then evaporated down. The residue is dissolved in acetone, mixed with diethyl ether and suction filtered.

Yield: 1.30 g (43% of theoretical)

Synthesis of the Intermediate Compounds
Synthesis of Intermediate Compound (IV)

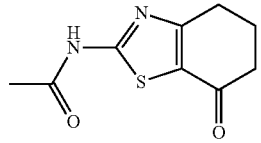

(IV)

112 g (1.0 mol) 1,3-cyclohexanedione are suspended in 700 mL ice water and 51.6 mL (1.0 mol) bromine are added dropwise at 0° C. within 45 minutes. The suspension is stirred for 3.5 hours at max. 10° C. Then it is suction filtered and the solid is stirred in 800 mL water, suction filtered, washed with 3 L water and dried. The solid obtained is recrystallised from ethanol. Yield: 37 g (m.p.: 159-160° C.)

15.5 g (0.2 mol) thiourea are placed in 200 mL ethanol at ambient temperature. To this suspension are added batchwise 37.1 g (0.2 mol) of the intermediate described above, then the mixture is rinsed with 60 mL ethanol. The solution that gradually forms is refluxed for 2 hours with stirring and then evaporated down. The residue is extracted with water and diethyl ether, the aqueous phase is made basic with sodium carbonate solution. The resulting solid is suction filtered, washed with water, then stirred with methanol and evaporated to dryness.

Yield: 22 g (m.p.: 265-268° C.)

230 mL (2.4 mol) acetic anhydride are placed at ambient temperature, 22 g (0.13 mol) of the intermediate described above are added and the mixture is refluxed for 3 hours with stirring. The suspension goes partly into solution. After cooling with ice/common salt bath the solid is solid suction filtered, decocted 2× in 150 mL acetone, suction filtered and dried.

Yield: 25 g (m.p.: 268-272° C.) of the intermediate compound (IV)

Synthesis of Intermediate Compound (VI.1)

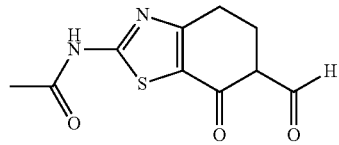

(VI.1)

20 g (0.37 mol) sodium methoxide are suspended in 50 mL dimethylformamide, a suspension of 21 g of the intermediate compound (IV) in 100 mL dimethylformamide is added dropwise. The mixture is stirred for another 15 minutes, then cooled to 0° C. A mixture of 29.9 mL (0.37 mol) ethyl formate (Va) and 60 mL benzene is added dropwise and the reaction mixture is diluted with another 100 mL benzene. Gradually a precipitate is formed and stirring is continued at 0° C. for 3.5 hours. The suspension is hydrolysed with 370 mL 1 molar hydrochloric acid, the solid precipitated is suction filtered. The two phases of the mother liquor are separated, the aqueous phase is extracted with dichloromethane. The resulting organic phase is dried and evaporated to dryness. The solid and the residue from the extraction are recrystallised from acetonitrile.

Yield: 20 g of the intermediate compound (VI.1)

Synthesis of Intermediate Compound (VIII.1)

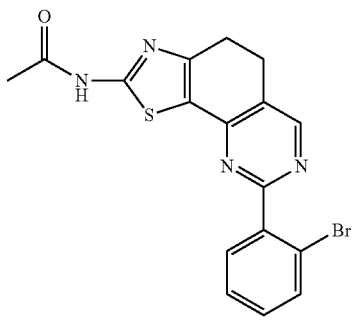

(VIII.1)

4.00 g (16.79 mmol) of intermediate compound (VI.1) are placed in 10 ml of pyridine, 3.95 g (20 mmol) 2-bromobenzamidine are added. The reaction mixture is stirred for 4 hours at 160° C. After cooling the mixture is precipitated with ethanol and water. The precipitate formed is suction filtered and dried.

Yield: 3.50 g (52% of theoretical) of intermediate compound (VIII.1)

The intermediates (VIII.2) to (VIII.6) may also be obtained analogously by reacting the intermediate (VI.1) with the appropriate amidines (VII.2-VII. 6).

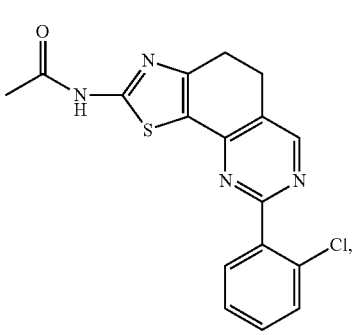

(VIII.2)

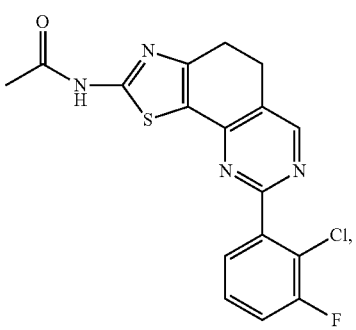

(VIII.3)

(VIII.4)

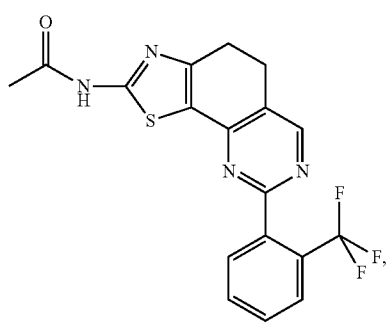

(VIII.5)

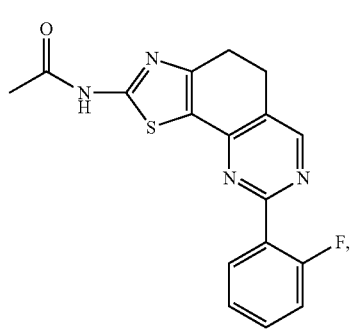

(VIII.6)

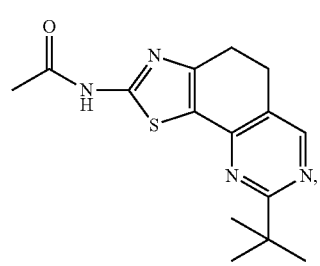

Synthesis of Intermediate Compound (IX.1)

(IX.1)

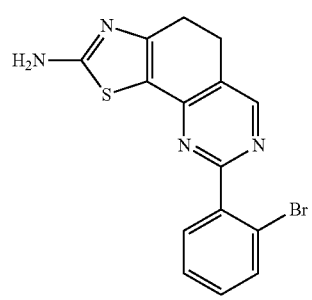

3.50 g (9 mmol) of the intermediate compound (VIII.1) are refluxed in 10 ml conc. hydrochloric acid and 10 ml of water for 2 hours with stirring. Then the precipitate formed is suction filtered and dried.

Yield: 2.40 g (77% of theoretical) of the intermediate compound (IX.1)

The intermediates (IX.2) to (IX.6) may also be prepared analogously by saponification of the intermediates (VIII.2) to (VIII.6).

(IX.2)

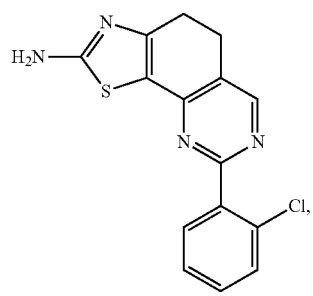

(IX.3)

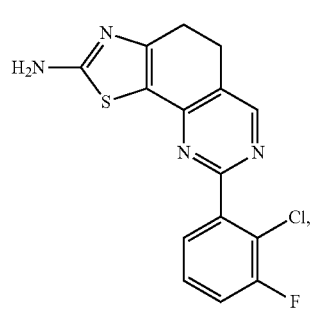

(IX.4)

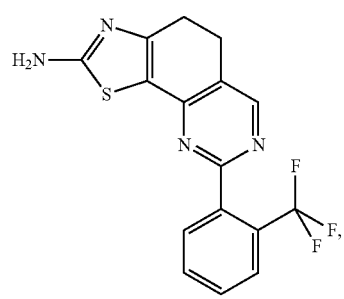

(IX.5)

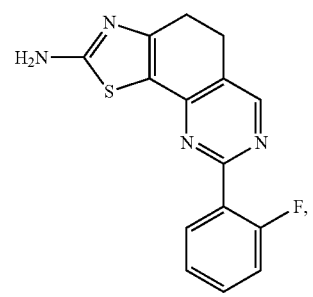

(IX.6)

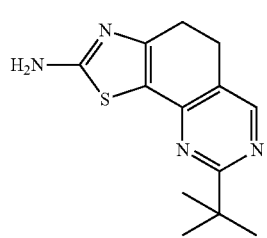

Synthesis of Intermediate Compound (XI.1)

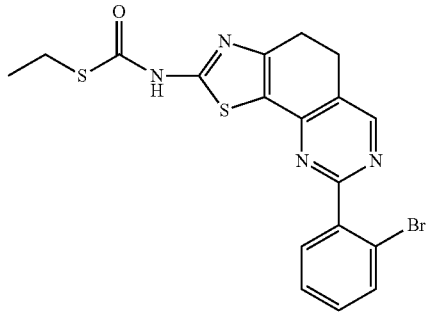
(XI.1)

2.40 g (7 mmol) of the intermediate compound (IX.1) and 0.73 ml (6.72 mmol) ethylchlorothiolformate are stirred in 2 ml of pyridine for 4 hours at 60° C. Then the reaction mixture is extracted with water and dichloromethane, the organic phase is treated with activated charcoal, dried and evaporated to dryness. The residue is purified by chromatography.

Yield: 1.50 g (50% of theoretical) of the intermediate compound (XI.1)

The intermediates (XI.2) to (XI.6) may also be prepared analogously by reacting the intermediates (IX.2) to (IX.6) with ethylchlorothiolformate (X.1).

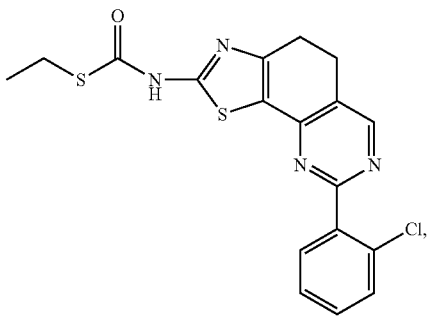
(XI.2)

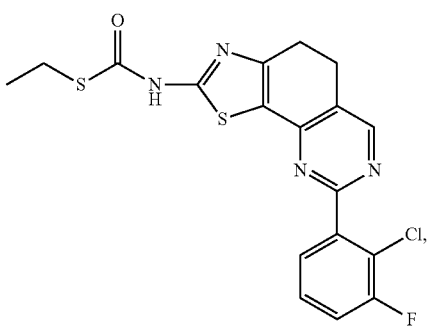
(XI.3)

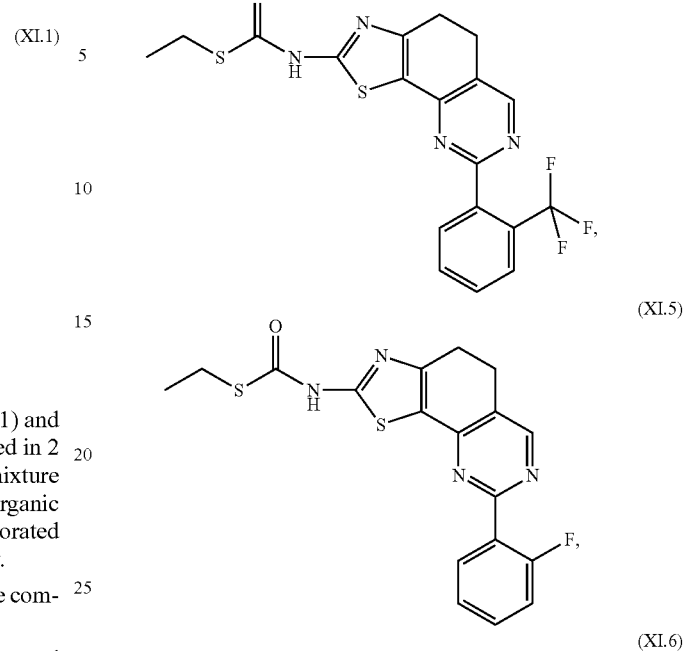
(XI.4)

(XI.5)

(XI.6)

Synthesis of Intermediate Compound (XVII.1)

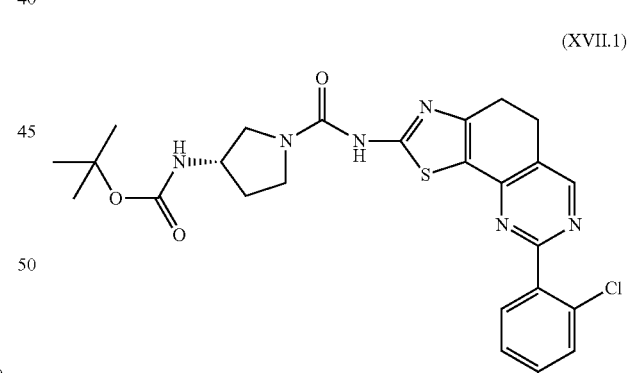
(XVII.1)

2.42 g (6 mmol of intermediate compound (XI.2), 1.12 g (6 mmol) (3S)-(+)-3-(tert.butoxycarbonylamino)pyrrolidine, 2.05 ml (12 mmol) diisopropylethylamine and 10 μl triethylamine are stirred in 30 ml of ethanol for 3 hours at 80° C. Then the mixture is stirred with dichloromethane, water and sodium carbonate, the organic phase is separated off using a phase separation cartridge and evaporated to dryness. The residue is stirred with diethyl ether and suction filtered.

Yield: 2.54 g (80% of theoretical) of the intermediate compound (XVII.1)

The intermediate compound (XVII.2) may also be obtained analogously.

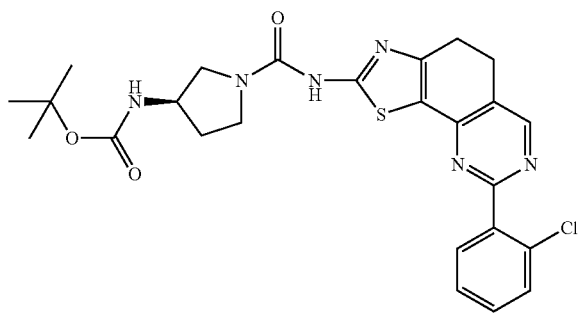

(XVII.2)

Synthesis of Intermediate Compound (XVIII.1)

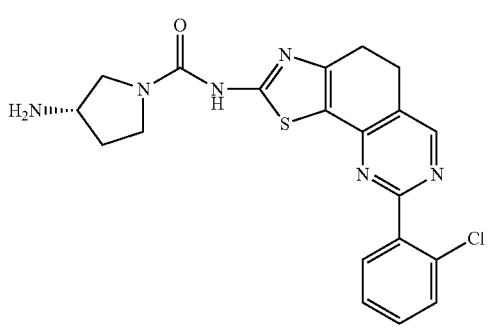

(XVIII.1)

2.60 g (4.92 mmol) of the intermediate compound (XVII.1) are stirred in 30 ml 2 molar ethereal hydrochloric acid for 3 hours at ambient temperature. The reaction mixture is evaporated to dryness.

Yield: 2.60 g (100% of theoretical) of the intermediate compound (XVIII.1)

The intermediate compound may also be obtained analogously (XVIII.2).

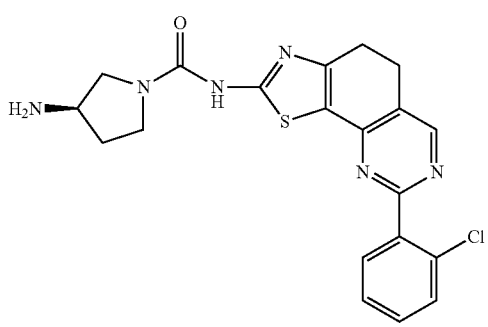

(XVIII.2)

Synthesis of Intermediate Compound (XXVII.1)

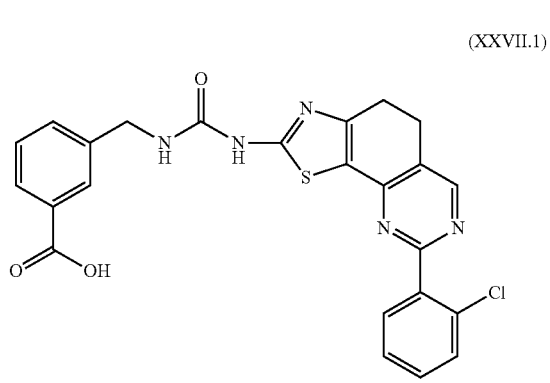 [SMILES: O=C(NCc1cccc(C(=O)O)c1)Nc1nc2c(s1)-c1nc(-c3ccccc3Cl)ncc1CC2]

(XXVII.1)

3.00 g (7.45 mmol) of intermediate compound (XI.2), 1.41 g (7.50 mmol) 3-aminomethyl-benzoic acid hydrochloride and 5.13 ml (30 mmol) triethylamine are stirred in 25 ml of tetrahydrofuran for 7 hours at 80° C. The resulting suspension is mixed with diethyl ether, the precipitate formed is suction filtered. This is stirred with dilute sodium hydrogen carbonate solution and suction filtered.

Yield: 3.30 g (90% of theoretical) of the intermediate compound (XXVII.1)

Synthesis of Intermediate Compound (XXV.1)

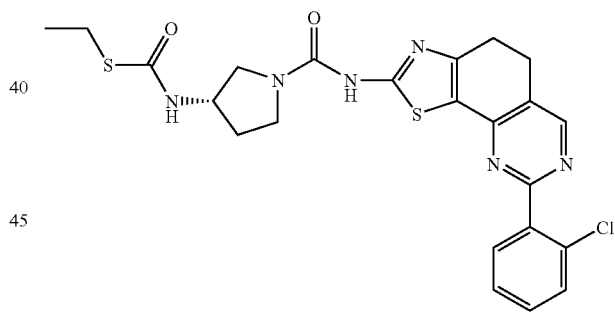

(XXV.1)

800 mg (1.73 mmol) of the intermediate compound (XVIII.1) and 195.49 µl (1.80 mmol) ethylchlorothiolformate are stirred in 5 ml of pyridine for 48 hours at 60° C. Then the reaction mixture is evaporated down, the residue is extracted with water and dichloromethane. The organic phase is dried and evaporated to dryness. The product is crystallised with diethyl ether.

Yield: 510 mg (57% of theoretical) of the intermediate compound (XXV.1)

HPLC-MS: method A, RT=2.82 min, MH+=515/517

Synthesis of Intermediate Compound (XXIX.1)

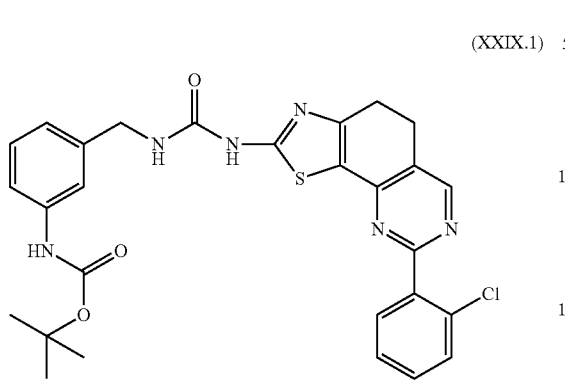

(XXIX.1)

2.25 g (5.79 mmol) of the intermediate compound (XI.2), 1.50 g (6.75 mmol) tert. butyl (3-aminomethyl-phenyl)-carbamate and 3.74 ml (27 mmol) triethylamine are stirred in 20 ml of ethanol for 16 hours at 80° C. Then the reaction mixture is evaporated down, the residue is extracted with water and dichloromethane. The organic phase is dried and evaporated to dryness. The residue is crystallised from ethanol and diethyl ether.

Yield: 2.63 g (81% of theoretical) of the intermediate compound (XXIX.1)

Synthesis of Intermediate Compound (XXX.1)=Example 5

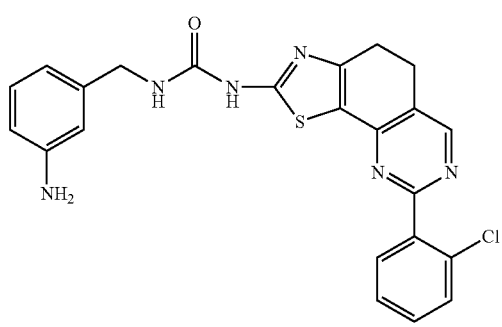

(XXX.1) = Example 5

2.63 g (4.67 mmol) of the intermediate compound (XXIX.1) are suspended in 20 ml ethereal hydrochloric acid, then stirred for 16 hours at ambient temperature. Then the precipitate is suction filtered and dried.

Yield: 2.50 g (100% of theoretical) of the intermediate compound (XXX.1)

Synthesis of intermediate compound (XXXIII.1)

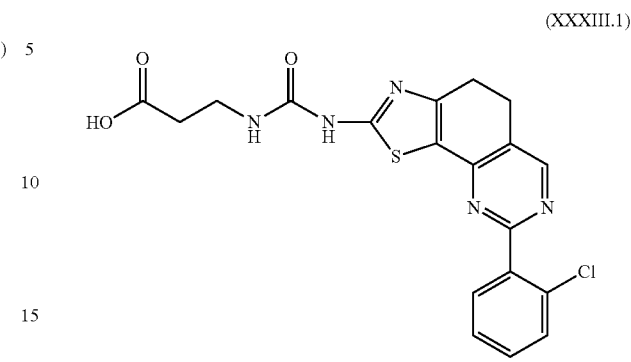

(XXXIII.1)

2.00 g (5.14 mmol) of the intermediate compound (XI.2), 600 mg (6.74 mmol) β-alanine and 0.80 ml (5.77 mmol) triethylamine are stirred in 10 ml of ethanol for 16 hours at 80° C. The precipitate formed is suction filtered, the mother liquor evaporated down. The residue is crystallised with dimethylformamide, water and trifluoroacetic acid.

Yield: 1.00 g (45% of theoretical) of the intermediate compound (XXXIII.1)

Synthesis of Intermediate Compound (XXXI.1)

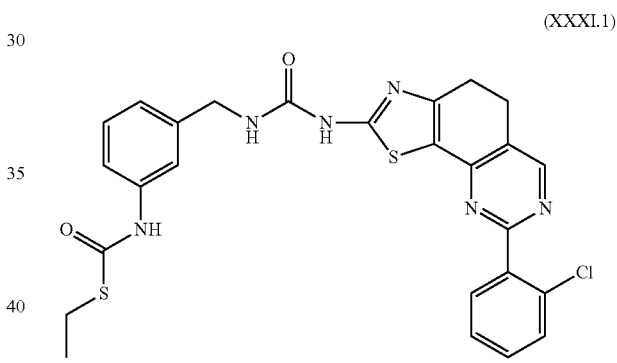

(XXXI.1)

600 mg (1.20 mmol) of the intermediate compound (XXX.1) and 135.76 µl (1.25 mmol) ethylchlorothiolformate are stirred in 12 ml of pyridine for 16 hours at ambient temperature. As the reaction is still incomplete, a further 0.2 eq ethylchlorothiolformate are added, and the mixture is stirred for 3 hours at 60° C. Then the reaction mixture is extracted with water and dichloromethane. The organic phase is dried and evaporated to dryness. The residue is crystallised with diethyl ether.

Yield: 540 mg (82% of theoretical) of the intermediate compound (XXXI.1)

Synthesis of the Compounds of Formula (I)

Methods A and B:

Waters ZMD, Alliance 2690/2695 HPLC, Waters 2700 Autosampler, Waters 996/2996 Diode array detector (wavelength range 210-400 nm).

Stationary phase (column temperature: constant at 25° C.):

method A: column XTerra®, MS $C_{18}$ 2.5 µm, 4.6 mm×30 mm.

method B: column Merck Chromolith™ SpeedROD RP-18e, 4.6 mm×50 mm.

Mobile phase: L1: water with 0.10% TFA; L2: acetonitrile with 0.10% TFA flow rates:

Method A: 1.00 mLl/min

Method B: 2.00 mL/min

| time (min) | % L1 | % L2 |
|---|---|---|
| 0.0 | 95 | 5 |
| 0.1 | 95 | 5 |
| 3.1 | 2 | 98 |
| 4.5 | 2 | 98 |
| 5.0 | 95 | 5 |

Methods C and D:
Waters ZMD, Alliance 2790/2795 HPLC, Waters 2700 Autosampler, Waters 996/2996 Diode array detector (wavelength range 210-500 nm).
Stationary phase (column temperature: constant at 40° C.):
column X-Terra MS C18 4.6×50 mm, 3.5 μm.
Mobile phase: L1: water with 0.10% TFA; L2: acetonitrile with 0.10% TFA
flow rates: 1.00 mL/min

| time (min) | % L1 | % L2 |
|---|---|---|
| 0.0 | 95 | 5 |
| 0.1 | 95 | 5 |
| 5.1 | 2 | 98 |
| 6.5 | 2 | 98 |
| 7.0 | 95 | 5 |

The symbol X used in Table A in the structural formula of the substituent is to be understood as being the linkage point to the remainder of the molecule. The substituent replaces the groups $R^a$ and $R^b$ according to the arrangement of the columns.

EXAMPLES

Synthesis of Example 17

70 mg (0.156 mmol) of intermediate compound (XI.1), 40.82 mg (0.172 mmol) 2-(4-ethyl-thiazol-2-yl)-ethylamine-hydrobromide and 0.10 ml (0.721 mmol) triethylamine are stirred in 1 ml of ethanol for 16 hours at 80° C. The reaction mixture is evaporated down, the residue is purified by chromatography.
Corresponding fractions are lyophilised.
Yield: 73.7 mg (87% of theoretical)
Examples 1, 6-16, 18-153 and 264 may also be obtained analogously by reacting the appropriate intermediate products (XI.1)-(XI.6) in each case with the appropriate amines (either known from the literature or described under "Synthesis of the reagents").

Synthesis of Example 154

20.15 mg (0.050 mmol) of the intermediate compound (XI.2) and 22.77 mg (0.225 mmol) triethylamine are placed in 1 ml of ethanol, 9.62 mg (0.075 mmol) (1-methyl-piperidin-4-yl)-methylamine in 1 ml of ethanol are added. The reaction mixture is stirred for 16 hours at 70° C. Then it is evaporated down, the residue is purified by chromatography (LCMS). Corresponding fractions are lyophilised.
Yield: 24.80 mg (85% of theoretical)
Examples 155-223 may also be obtained analogously by reacting the appropriate intermediate products (XI.1)-(XI.6) with the appropriate amines (either known from the literature or described under "Synthesis of the reagents").

Synthesis of Example 225

60 mg (0.129 mmol) of the intermediate compound (XVIII.1) and 100 μl (0.573 mmol) diisopropylethylamine are placed in 1 ml dimethylformamide, 22.96 μl (0.200 mmol) 4-morpholino-carbonyl chloride are added. The mixture is stirred for 16 hours at ambient temperature, then purified by chromatography (HPLC). Corresponding fractions are lyophilised.
Yield: 47 mg (67% of theoretical)
Examples 224 and 226-237 may also be obtained analogously by reacting the intermediate products (XVIII.1) with the respective appropriate carboxylic acid chlorides, sulphonic acid chlorides, carbamoyl chlorides, sulphamoyl chlorides or chloroformates. Moreover Examples 279 and 280 may be prepared analogously starting from intermediate compound (XXX.1).

Synthesis of Example 238

19.62 μl (0.180 mmol) isovaleric acid are placed in 5 ml dichloromethane, 100 μl (0.585 mmol) diisopropylethylamine and 64.87 mg (0.200 mmol) O-(1H-benzotriazol-1-yl)-N,N,N',N'-tetramethyluronium tetrafluoroborate (TBTU) are added. The mixture is stirred for 0.5 hours at ambient temperature, then 80 mg (0.173 mmol) of the intermediate compound (XVIII.1) are added. The reaction mixture is stirred for 16 hours at ambient temperature, then stirred with dichloromethane, water and potassium carbonate. The organic phase is separated off using a phase separation cartridge and evaporated to dryness. The residue is crystallised with diethyl ether.
Yield: 51 mg (58% of theoretical)
Example 239 may also be prepared analogously by reacting the intermediate products (XVIII.1) with the appropriate carboxylic acid.

Synthesis of Example 241

80 mg (0.173 mmol) of the intermediate compound (XVIII.2) and 150 μl (0.860 mmol) diisopropylethylamine are placed in 1.50 ml dimethylformamide, 26.19 μl (0.200 mmol) isobutyryl chloride are added while cooling. The mixture is stirred for 16 hours at ambient temperature, then purified by chromatography (HPLC). Corresponding fractions are lyophilised.
Yield: 58 mg (68% of theoretical)
Examples 240 and 242-249 may also be obtained analogously by reacting the intermediate compound (XVIII.2) with the respective appropriate carboxylic acid chlorides, sulphonic acid chlorides, carbamoyl chlorides, sulphamoyl chlorides or chloroformates.

Synthesis of Example 250

19.62 μl (0.180 mmol) isovaleric acid are placed in 5 ml dichloromethane, 100 μl (0.585 mmol) diisopropylethylamine and 64.87 mg (0.200 mmol) O-(1H-benzotriazol-1-yl)-N,N,N',N'-tetramethyluronium tetrafluoroborate (TBTU) are added. The mixture is stirred for 0.5 hours at ambient temperature, then 80 mg (0.173 mmol) of the intermediate compound (XVIII.2) are added. The reaction mixture is stirred for 16 hours at ambient temperature, then stirred with dichloromethane, water and potassium carbonate. The organic phase is separated off using a phase separation cartridge and evaporated to dryness. The residue is crystallised with diethyl ether.
Yield: 62 mg (70% of theoretical)
mp: 203°-204° C.

Example 251 may also be prepared analogously by reacting the intermediate compound (XVIII.2) with the appropriate carboxylic acid.

Synthesis of Example 252

100 mg (0.203 mmol) of the intermediate compound (XXVII.1) are placed in 4 ml dichloromethane, 100 µl (0.585 mmol) diisopropylethylamine and 75 mg (0.231 mmol) O-(1H-benzotriazol-1-yl)-N,N,N',N'-tetramethyluronium tetrafluoroborate (TBTU) are added. The mixture is stirred for 0.5 hours at ambient temperature, then 24.84 µl (0.250 mmol) isobutylamine are added. The reaction mixture is stirred for 16 hours at ambient temperature, then stirred with dichloromethane, water and potassium carbonate. The organic phase is separated off using a phase separation cartridge and evaporated to dryness. The residue is purified by chromatography (HPLC), corresponding fractions are lyophilised.

Yield: 53 mg (48% of theoretical)

Examples 253-259 may also be obtained analogously by reacting the intermediate compound (XXVII.1) with the appropriate amines.

Synthesis of Example 260

75 mg (0.146 mmol) of the intermediate compound (XXV.1), 30 ml (0.350 mmol) isopropylamine, 51.29 µl (0.300 mmol) diisopropylethylamine and 10 µl triethylamine are stirred in 1 ml of ethanol for 3 hours at 80° C. Then the reaction mixture is stirred with dichloromethane and water, the organic phase is separated off using a phase separation cartridge and evaporated down. The residue is crystallised with diethyl ether.

Yield: 53 mg (71% of theoretical)

mp: 198-199° C.

HPLC-MS: method A, RT=2.54 min, MH+=512

Examples 261-263 and 265 may also be obtained analogously by reacting the intermediate compound (XXV.1) with the appropriate amines.

Synthesis of Example 266

10 mg (0.100 mmol) cyclopropylacetic acid are placed in 1 ml dimethylformamide, 37 mg (0.113 mmol) O-(1H-benzotriazol-1-yl)-N,N,N',N'-tetramethyluronium tetrafluoroborate (TBTU) and 90 ml (0.516 mmol) diisopropylethylamine are added. The mixture is stirred for 0.5 hours at ambient temperature, then combined with 60 mg (0.141 mmol) of the intermediate compound (XVIII.1). The reaction mixture is stirred for 24 hours at ambient temperature, then extracted with potassium carbonate solution and dichloromethane. The organic phase is dried and evaporated to dryness. The residue is purified by chromatography (HPLC). Corresponding fractions are lyophilised.

Yield: 35.5 mg (70% of theoretical)

HPLC-MS: method A, RT=2.65 min, MH+=509

Examples 267-273 may also be obtained analogously by reacting the intermediate products of the intermediate compound (XVIII.1) with the respective appropriate carboxylic acids.

Synthesis of Example 274

14.43 mg (0.240 mmol) acetic acid, 92.59 mg (0.288 mmol) O-(1H-benzotriazol-1-yl)-N,N,N',N'-tetramethyluronium tetrafluoroborate (TBTU) and 213.90 µl (1.25 mmol) diisopropylethylamine are placed in 2 ml dimethylformamide, and the mixture is stirred for 0.5 hours at ambient temperature. 120 mg (0.240 mmol) of the intermediate compound (XXX.1) are added and the mixture is stirred for 16 hours at ambient temperature. Then the reaction mixture is purified by chromatography (HPLC). Corresponding fractions are lyophilised.

Yield: 77 mg (63% of theoretical)

Examples 275-278 may also be obtained analogously by reacting the intermediate compound (XXX.1) with the respective appropriate carboxylic acids.

Synthesis of Example 281

70 mg (0.163 mmol) of the intermediate compound (XXXIII.1), 62.74 mg (0.195 mmol) O-(1H-benzotriazol-1-yl)-N,N,N',N'-tetramethyluronium tetrafluoroborate (TBTU) and 144.96 µl diisopropylethylamine are suspended in 2 ml dimethylformamide and the mixture is stirred for 0.5 hours at ambient temperature. 10.59 mg (0.179 mmol) isopropylamine are added and the mixture is stirred for 16 hours at ambient temperature. Then the reaction mixture is purified by chromatography (HPLC). Corresponding fractions are lyophilised.

Yield: 22 mg (29% of theoretical)

Examples 282-293 may also be obtained analogously by reacting the intermediate compound (XXXIII.1) with the appropriate amines.

Synthesis of Example 294

80 mg (0.145 mmol) of the intermediate compound (XXXI.1) and 200 µl (0.400 mmol) 2 molar dimethylamine solution in tetrahydrofuran are stirred in 1 ml of ethanol for 3 hours at 80° C. Then the mixture is evaporated down, the residue is extracted with water and dichloromethane. The organic phase is dried and evaporated to dryness. The product is crystallised with diethyl ether.

Yield: 50 mg (64% of theoretical)

Examples 295-299 may also be obtained analogously by reacting the intermediate compound (XXXI.1) with the appropriate amines.

Synthesis of Example 3

20 mg (0.032 mmol) of the Example compound 133 are stirred in 20 ml ethereal hydrochloric acid for 16 hours at ambient temperature. Then the precipitate is suction filtered and dried.

Yield: 10 mg (56% of theoretical)

MP: 240° C.

Analogously, Examples 2 and 4 may be obtained from the Example compounds 132 and 135, respectively.

The following compounds are prepared analogously:

TABLE A

| Ex. No. | Rc = ![R1,R2 substituent with N-X amide] | Ra | mp [° C.] | HPLC method | RT [min] |
|---|---|---|---|---|---|
| 1 | X-NH-C(O)-N(CH₃)-CH₂CH₂-OCH₃ | 2-chlorophenyl | | B | 1.83 |
| 2 | X-NH-C(O)-NH-CH₂-(S)-pyrrolidin-2-yl | 2-chlorophenyl | 149 | | |
| 3 | X-NH-C(O)-NH-CH₂-pyrrolidin-2-yl | 2-chlorophenyl | | | |
| 4 | X-NH-C(O)-NH-(4-piperazin-1-yl-phenyl) | 2-chlorophenyl | 240 | | |
| 5 | X-NH-C(O)-NH-CH₂-(3-aminophenyl) | 2-chlorophenyl | 210-250 | | |
| 6 | X-NH-C(O)-NH-CH₂-(3-isopropylphenyl) | 2-chlorophenyl | | B | 2.26 |
| 7 | X-NH-C(O)-NH-CH₂-(3-(2-oxopyrrolidin-1-yl)phenyl) | 2-chlorophenyl | | A | 2.81 |

TABLE A-continued
(IA)
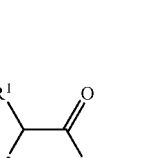
| Ex. No. | Rc =  | Ra | mp [° C.] | HPLC method | RT [min] |
|---|---|---|---|---|---|
| 8 |  |  | 240-241 | | |
| 9 |  |  | | | |
| 10 | 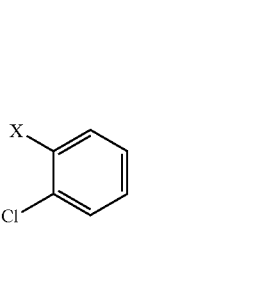 |  | | A | 2.77 |
| 11 | | | | | |

TABLE A-continued

| Ex. No. | Rc = | Ra | mp [° C.] | HPLC method | RT [min] |
|---|---|---|---|---|---|
| 12 | | 2-Cl-phenyl | | | |
| 13 | | 2-Br-phenyl | | | |
| 14 | | 2-Cl-phenyl | 230 | | |
| 15 | | 2-Br-phenyl | | | |
| 16 | | 2-Cl-phenyl | | | |
| 17 | | 2-Br-phenyl | | | |
| 18 | | 2-CF₃-phenyl | | | |
| 19 | | 2-Cl-phenyl | | | |

TABLE A-continued (IA)

| Ex. No. | Rc = | Ra | mp [° C.] | HPLC method | RT [min] |
|---|---|---|---|---|---|
| 20 | | 2-F-phenyl | | | |
| 21 | | tert-butyl | | | |
| 22 | | 2-Br-phenyl | | | |
| 23 | | 2-Cl-phenyl | | | |
| 24 | | 2-F-phenyl | | A | 2.68 |
| 25 | | 2-Br-phenyl | | | |
| 26 | | 2-CF3-phenyl | | | |
| 27 | | 2-Cl-phenyl | | | |
| 28 | | 2-F-phenyl | | | |

TABLE A-continued (IA)

| Ex. No. | Rc = | Ra | mp [° C.] | HPLC method | RT [min] |
|---|---|---|---|---|---|
| 29 | urea-CH2CH2-(5-isopropyloxazol-2-yl) | 2-Br-C6H4 | | | |
| 30 | urea-CH2CH2-(5-isopropyloxazol-2-yl) | 2-Cl-C6H4 | | | |
| 31 | urea-CH2CH2-(5-isopropyl-1,3,4-oxadiazol-2-yl) | 2-Br-C6H4 | | | |
| 32 | urea-CH2CH2-(5-isopropyl-1,3,4-oxadiazol-2-yl) | 2-CF3-C6H4 | | A | 2.90 |
| 33 | urea-CH2CH2-(5-isopropyl-1,3,4-oxadiazol-2-yl) | 2-Cl-C6H4 | | | |
| 34 | urea-CH2CH2-(5-isopropyl-1,3,4-oxadiazol-2-yl) | 2-F-C6H4 | | | |
| 35 | urea-CH2CH2-(3-ethyl-1,2,4-oxadiazol-5-yl) | 2-Br-C6H4 | | | |

TABLE A-continued
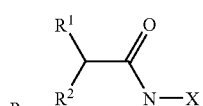
(IA)
| Ex. No. | Rc = 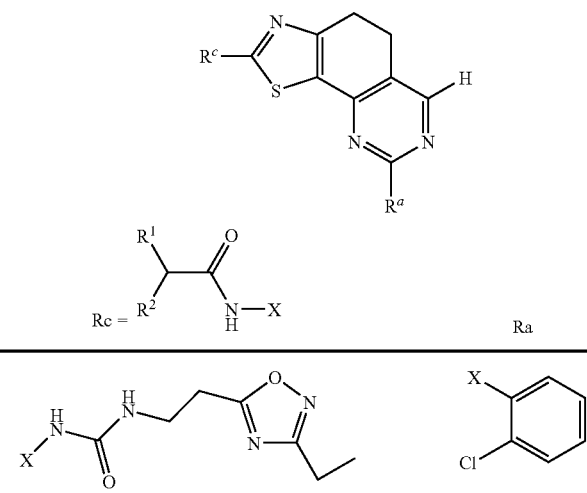 | Ra | mp [° C.] | HPLC method | RT [min] |
|---|---|---|---|---|---|
| 36 | 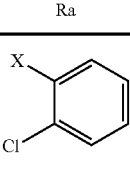 | 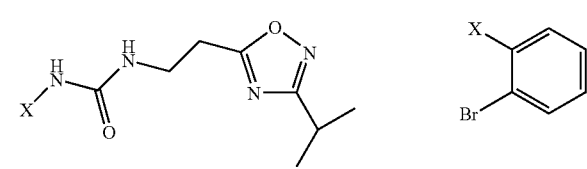 | | | |
| 37 | 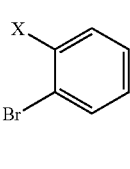 | 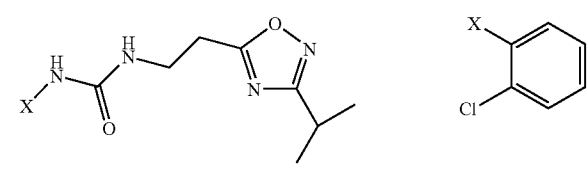 | | | |
| 38 | 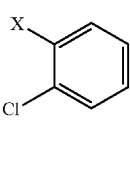 | 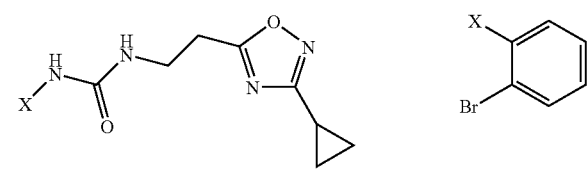 | | | |
| 39 | 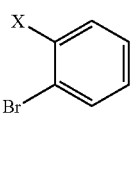 | 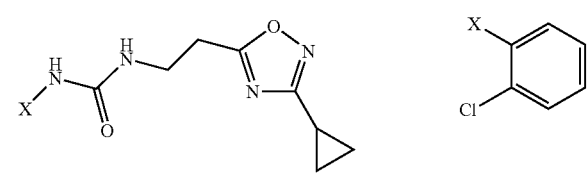 | | | |
| 40 | 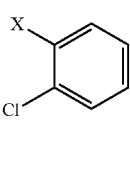 | 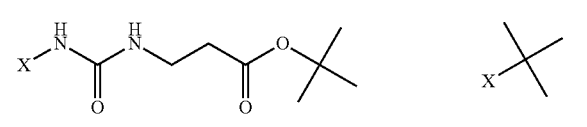 | | | |
| 41 | 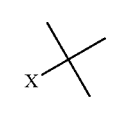 | 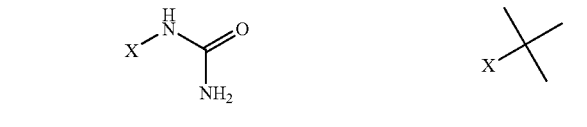 | | | |
| 42 | 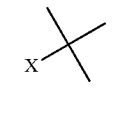 |  | | | |
| 43 | 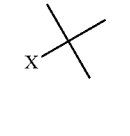 | | 331-333 | | |

TABLE A-continued
(IA)
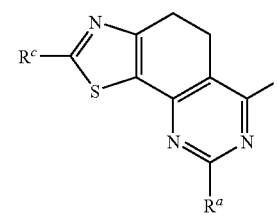
| Ex. No. | Rc = 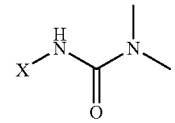 | Ra | mp [° C.] | HPLC method | RT [min] |
|---|---|---|---|---|---|
| 44 |  | 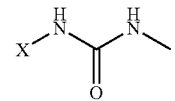 | | | |
| 45 | 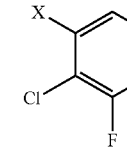 | 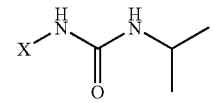 | | A | 2.73 |
| 46 | 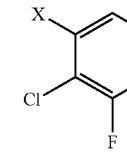 | 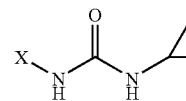 | 135 | A | 3.04 |
| 47 | 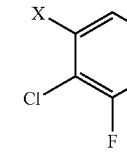 | 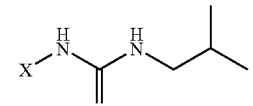 | 218 | A | 2.90 |
| 48 | 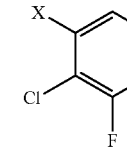 | 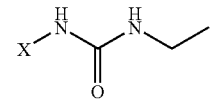 | 139 | A | 3.19 |
| 49 | 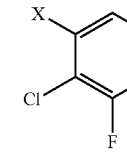 | 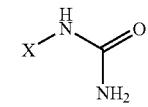 | 138 | | |
| 50 | 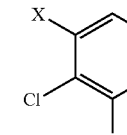 | 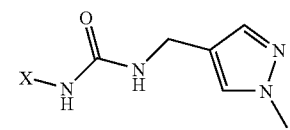 | 153-155 | A | 2.64 |
| 51 | 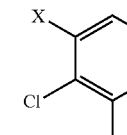 | | | A | 2.72 |

TABLE A-continued
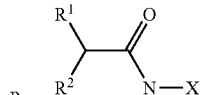
(IA)
| Ex. No. | Rc = 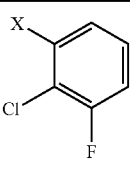 | Ra | mp [° C.] | HPLC method | RT [min] |
|---|---|---|---|---|---|
| 52 | 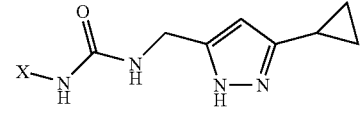 | 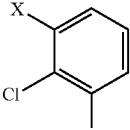 | | A | 2.84 |
| 53 | 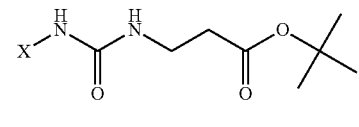 | 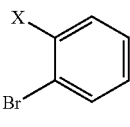 | | B | 1.83 |
| 54 | 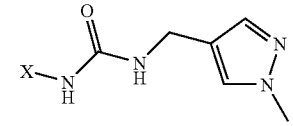 | 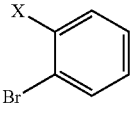 | | | |
| 55 | 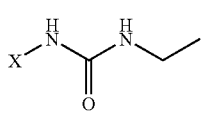 | 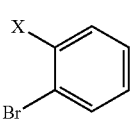 | | A | 2.51 |
| 56 | 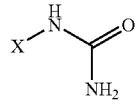 | 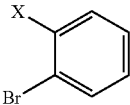 | >300 | | |
| 57 | 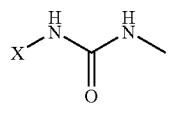 | 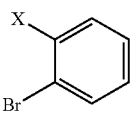 | >300 | | |
| 58 | 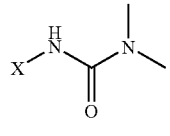 | 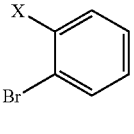 | >300 | A | 2.59 |
| 59 | 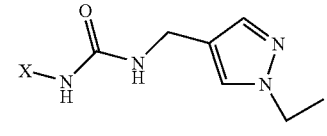 | 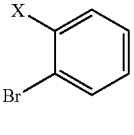 | 251 | | |
| 60 | | | | A | 2.71 |

TABLE A-continued

| Ex. No. | Rc = | Ra | mp [° C.] | HPLC method | RT [min] |
|---|---|---|---|---|---|
| 61 | urea-CH2-(5-cyclopropyl-1H-pyrazol-3-yl) | 2-bromophenyl | | B | 2.02 |
| 62 | urea-CH2-(1-methyl-1H-pyrazol-4-yl) | 2-(trifluoromethyl)phenyl | | A | 2.72 |
| 63 | urea (NH2) | 2-(trifluoromethyl)phenyl | | | |
| 64 | N-methylurea | 2-(trifluoromethyl)phenyl | | | |
| 65 | N,N-dimethylurea | 2-(trifluoromethyl)phenyl | | | |
| 66 | urea-CH2-(5-cyclopropyl-1H-pyrazol-3-yl) | 2-(trifluoromethyl)phenyl | | B | 1.81 |
| 67 | N-benzylurea | 2-chlorophenyl | | | |
| 68 | N-(3-methylbenzyl)urea | 2-chlorophenyl | | | |

TABLE A-continued
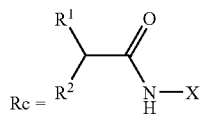
(IA)
| Ex. No. | Rc = | Ra | mp [° C.] | HPLC method | RT [min] |
|---|---|---|---|---|---|
| 69 | 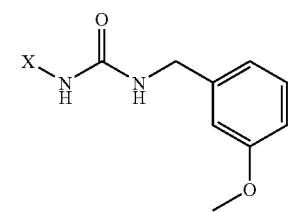 | 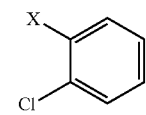 | | | |
| 70 | 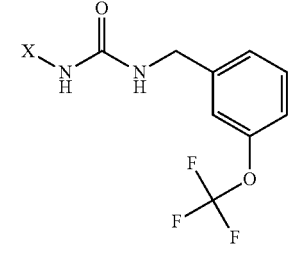 | 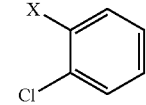 | | | |
| 71 | 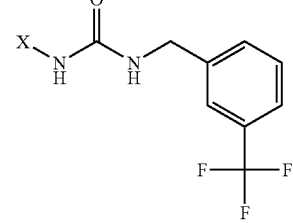 | 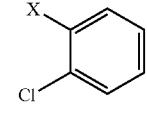 | | | |
| 72 | 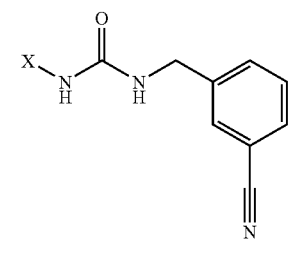 | 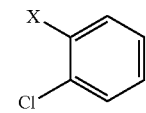 | | | |
| 73 | 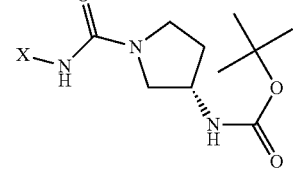 | 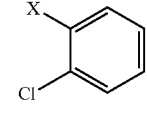 | 194-196 | | |

TABLE A-continued
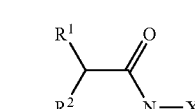
(IA)
| Ex. No. | Rc = 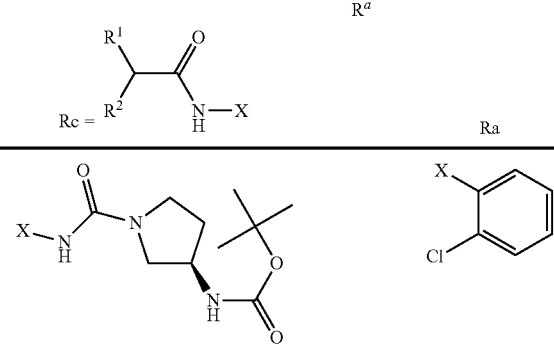 | Ra | mp [° C.] | HPLC method | RT [min] |
|---|---|---|---|---|---|
| 74 | 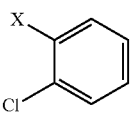 | 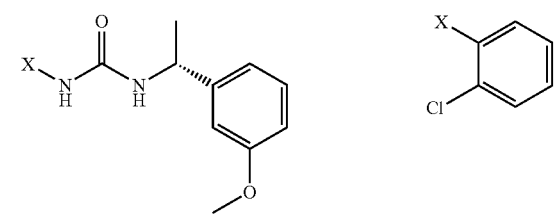 | 203-205 | A | 2.98 |
| 75 | 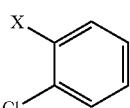 | 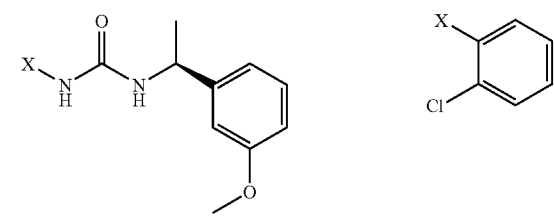 | 125-127 | | |
| 76 | 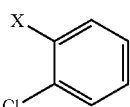 | 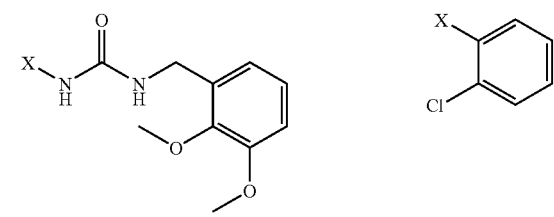 | 129-131 | | |
| 77 | 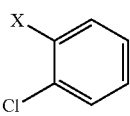 | 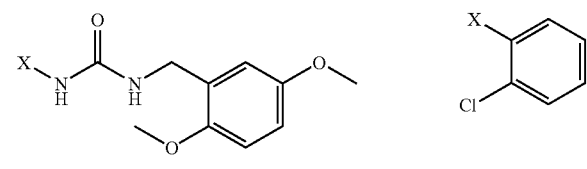 | 206-207 | | |
| 78 | 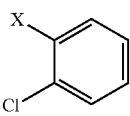 | 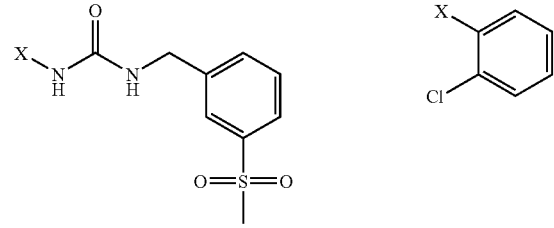 | 126-129 | | |
| 79 | 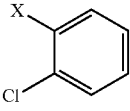 | | | A | 2.76 |

TABLE A-continued
(IA)
| Ex. No. | Rc = 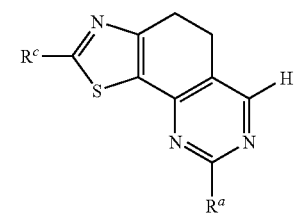 | Ra | mp [° C.] | HPLC method | RT [min] |
|---|---|---|---|---|---|
| 80 | 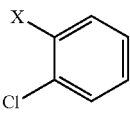 | 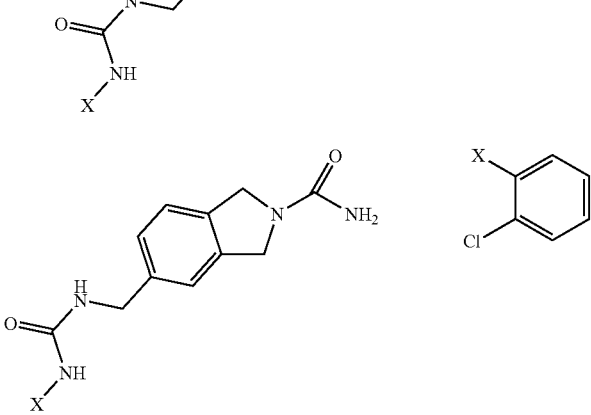 | | B | 2.00 |
| 81 | 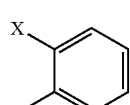 |  | 271-273 | B | 1.73 |
| 82 | 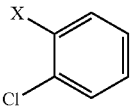 | 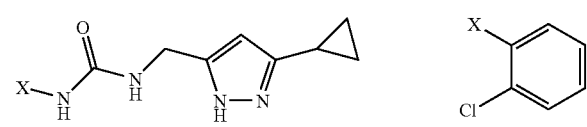 | | A | 2.81 |
| 83 | 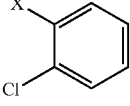 | 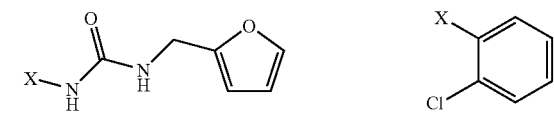 | | A | 2.54 |
| 84 | 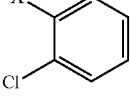 | 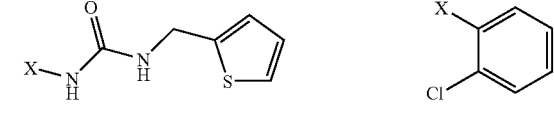 | | A | 2.91 |
| 85 | 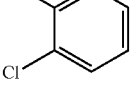 | 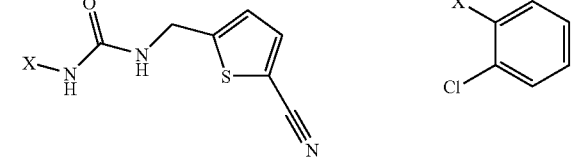 | | A | 3.01 |
| 86 | 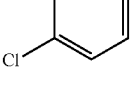 |  | | A | 1.97 |

TABLE A-continued

| Ex. No. | Rc = | Ra | mp [° C.] | HPLC method | RT [min] |
|---|---|---|---|---|---|
| 87 | | 2-Cl-C6H4 | | A | 2.37 |
| 88 | | 2-Cl-C6H4 | | | |
| 89 | | 2-Cl-C6H4 | | | |
| 90 | | 2-Cl-C6H4 | | | |
| 91 | | 2-Cl-C6H4 | >300 | | |
| 92 | | 2-Cl-C6H4 | 95-96 | | |
| 93 | | 2-Cl-C6H4 | | A | 2.69 |
| 94 | | 2-Cl-C6H4 | | | |
| 95 | | 2-Cl-C6H4 | 230 | | |

TABLE A-continued (IA)

| Ex. No. | Rc = | Ra | mp [° C.] | HPLC method | RT [min] |
|---|---|---|---|---|---|
| 96 | X-NH-C(O)-NH-CH₂-cyclohexyl | 2-Cl-C₆H₄ | 99 | | |
| 97 | X-NH-C(O)-NH-CH₂-(N-methylpiperidin-4-yl) | 2-Cl-C₆H₄ | 185 | | |
| 98 | X-NH-C(O)-NH-CH₂-cyclopropyl | 2-Cl-C₆H₄ | 184 | | |
| 99 | X-NH-C(O)-NH-CH₂-C(CH₃)₃ | 2-Cl-C₆H₄ | 135 | | |
| 100 | X-NH-C(O)-NH-CH₂-C(O)-N(CH₃)₂ | 2-Cl-C₆H₄ | >300 | | |
| 101 | cyclobutyl-NH-C(O)-NH-X | 2-Cl-C₆H₄ | | | |
| 102 | X-NH-C(O)-NH-CH₂-C(O)-O-CH₃ | 2-Cl-C₆H₄ | 232 | | |
| 103 | X-NH-C(O)-NH-CH₂CH₂-O-CH₂CH₃ | 2-Cl-C₆H₄ | 102 | | |
| 104 | X-NH-C(O)-NH-CH₂CH₂-O-CH(CH₃)₂ | 2-Cl-C₆H₄ | 142 | | |

TABLE A-continued (IA)

| Ex. No. | Rc = | Ra | mp [° C.] | HPLC method | RT [min] |
|---|---|---|---|---|---|
| 105 | urea-CH₂CH₂-O-tBu | 2-Cl-phenyl | | | |
| 106 | urea-CH₂CH₂CH₂-OMe | 2-Cl-phenyl | | | |
| 107 | urea-CH₂-(tetrahydropyran-4-yl) | 2-Cl-phenyl | 108 | | |
| 108 | urea-CH₂CH₂CH₂-O-iPr | 2-Cl-phenyl | | | |
| 109 | urea-CH₂CH₂-C(O)O-tBu | 2-Cl-phenyl | | | |
| 110 | urea-CH₂CH₂-C(O)NHMe | 2-Cl-phenyl | | | |
| 111 | urea-CH₂CH₂-C(O)NMe₂ | 2-Cl-phenyl | | | |
| 112 | urea-CH₂CH₂-C(O)-morpholine | 2-Cl-phenyl | 269 | | |

TABLE A-continued
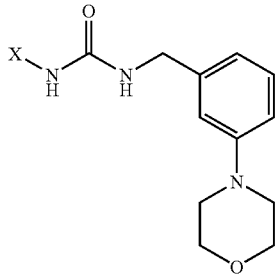
(IA)
| Ex. No. | Rc = 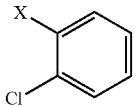 | Ra | mp [° C.] | HPLC method | RT [min] |
|---|---|---|---|---|---|
| 113 | 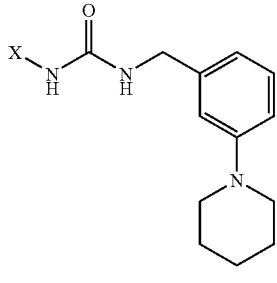 | 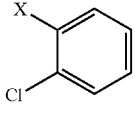 | 285 | | |
| 114 | 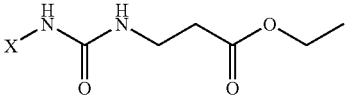 | 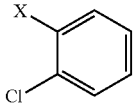 | 186 | | |
| 115 | 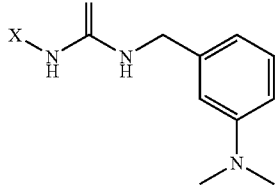 | 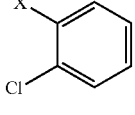 | | | |
| 116 | 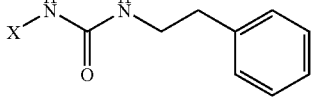 | 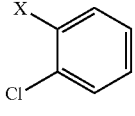 | | A | 2.36 |
| 117 | 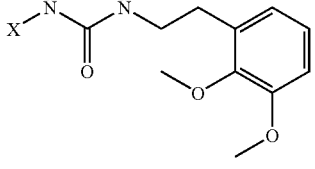 | 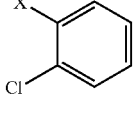 | | A | 3.16 |
| 118 | | | | A | 3.12 |

US 8,354,418 B2
TABLE A-continued
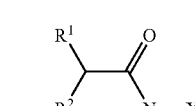
(IA)
| Ex. No. | Rc = 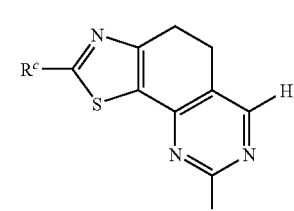 | Ra | mp [° C.] | HPLC method | RT [min] |
|---|---|---|---|---|---|
| 119 | 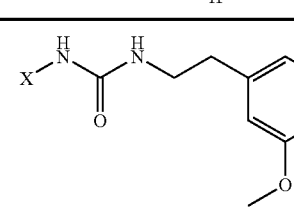 | 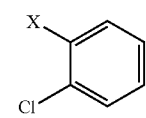 | | A | 3.14 |
| 120 | 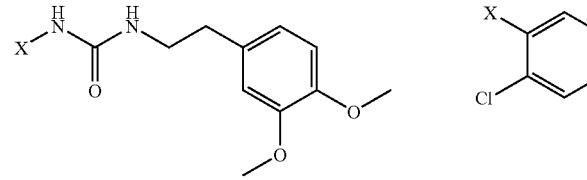 | 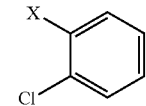 | | A | 2.99 |
| 121 | 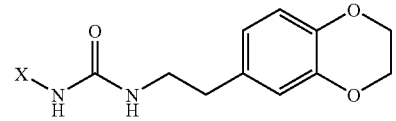 | 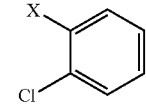 | | A | 3.09 |
| 122 | 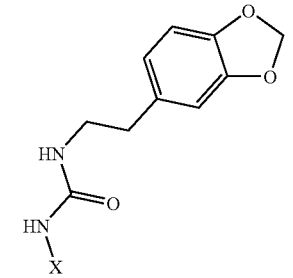 | 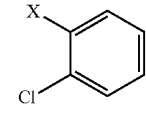 | | A | 3.11 |
| 123 | 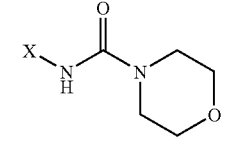 | 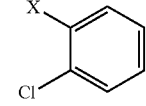 | | | |
| 124 | 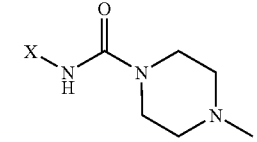 | 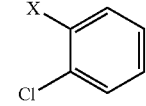 | | | |
| 125 | 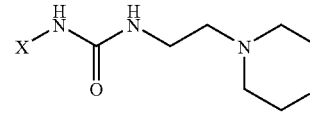 | 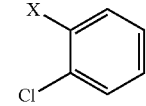 | Decomposn at 230 | | |

TABLE A-continued (IA)

| Ex. No. | Rc = | Ra | mp [° C.] | HPLC method | RT [min] |
|---|---|---|---|---|---|
| 126 | X-NH-C(O)-NH-CH₂CH₂-(pyrrolidin-1-yl) | 2-Cl-C₆H₄-X | Decomposn at 195 | | |
| 127 | X-NH-C(O)-NH-(CH₂)₄-N(CH₃)₂ | 2-Cl-C₆H₄-X | Decomposn at 182 | | |
| 128 | X-NH-C(O)-NH-CH₂CH₂-(imidazol-1-yl) | 2-Cl-C₆H₄-X | 210 | | |
| 129 | X-NH-C(O)-NH-CH₂CH₂-N(Et)₂ | 2-Cl-C₆H₄-X | | | |
| 130 | X-NH-C(O)-NH-C₆H₄-4-CH₂-(4-methylpiperazin-1-yl) | 2-Cl-C₆H₄-X | | | |
| 131 | X-NH-C(O)-NH-C₆H₄-3-CH₂-(4-methylpiperazin-1-yl) | 2-Cl-C₆H₄-X | | | |
| 132 | X-NH-C(O)-NH-CH₂-[(2S)-1-Boc-pyrrolidin-2-yl] | 2-Cl-C₆H₄-X | | | |

TABLE A-continued

| Ex. No. | Rc = | Ra | mp [° C.] | HPLC method | RT [min] |
|---|---|---|---|---|---|
| 133 | | 2-Cl-phenyl | | | |
| 134 | | 2-Cl-phenyl | | | |
| 135 | | 2-Cl-phenyl | | | |
| 136 | | 2-Cl-phenyl | | | |
| 137 | | 2-Cl-phenyl | | | |
| 138 | | 2-Cl-phenyl | | | |
| 139 | | 2-Cl-phenyl | | | |

TABLE A-continued
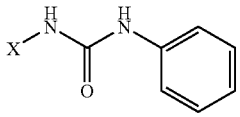
(IA)
| Ex. No. | Rc = 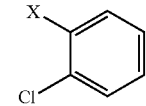 | Ra | mp [° C.] | HPLC method | RT [min] |
|---|---|---|---|---|---|
| 140 | 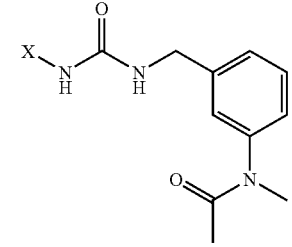 | 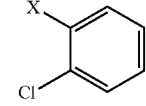 | | | |
| 141 | 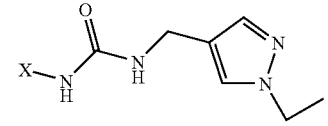 | 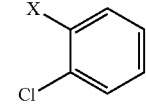 | | A | 2.68 |
| 142 | 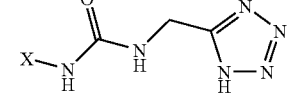 | 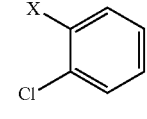 | | A | 2.67 |
| 143 | 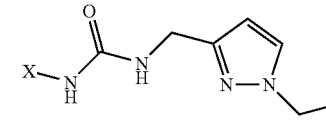 | 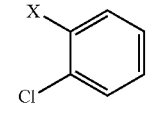 | | B | 1.61 |
| 144 | 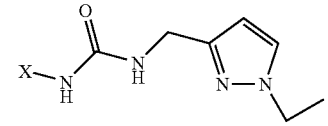 | 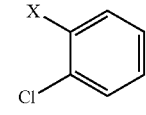 | | A | 2.82 |
| 145 | 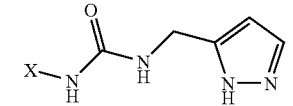 | 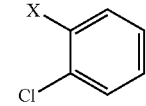 | | B | 1.82 |
| 146 | 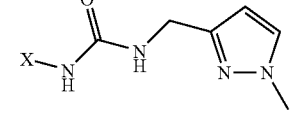 | 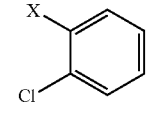 | | B | 1.65 |
| 147 |  |  | | B | 1.74 |

TABLE A-continued
(IA)
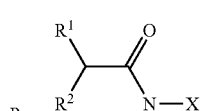
| Ex. No. | Rc = | Ra | mp [° C.] | HPLC method | RT [min] |
|---|---|---|---|---|---|
| 148 | 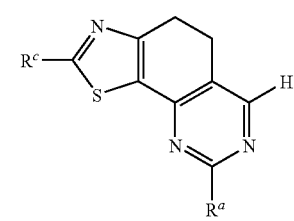 | 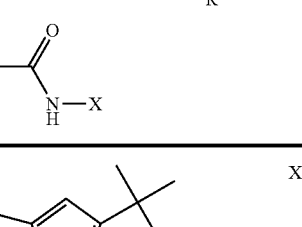 | | A | 2.72 |
| 149 | 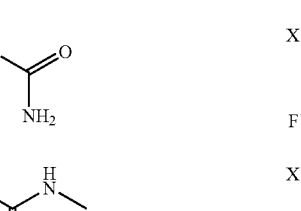 | 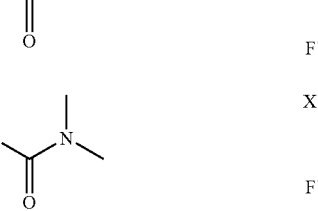 | 347-349 | | |
| 150 | 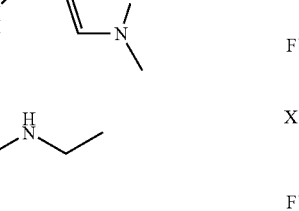 | 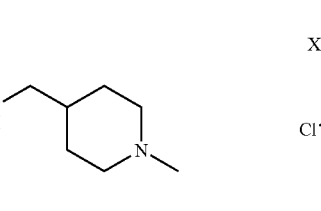 | 340-343 | | |
| 151 | 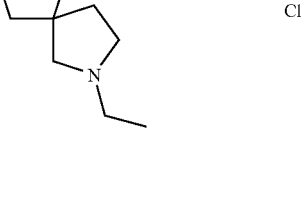 |  | | | |
| 152 | | | | A | 1.66 |
| 153 | | | 351-353 | | |
| 154 | | | | C | 3.23 |
| 155 | | | | C | 3.29 |

TABLE A-continued (IA)

| Ex. No. | Rc = | Ra | mp [° C.] | HPLC method | RT [min] |
|---|---|---|---|---|---|
| 156 | | 2-Cl-phenyl | | C | 3.28 |
| 157 | | 2-Cl-phenyl | | C | 3.73 |
| 158 | | 2-Cl-phenyl | | C | 3.38 |
| 159 | | 2-Cl-phenyl | | C | 3.73 |
| 160 | | 2-Cl-phenyl | | C | 4.31 |

TABLE A-continued
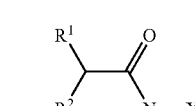
(IA)
| Ex. No. | Rc = 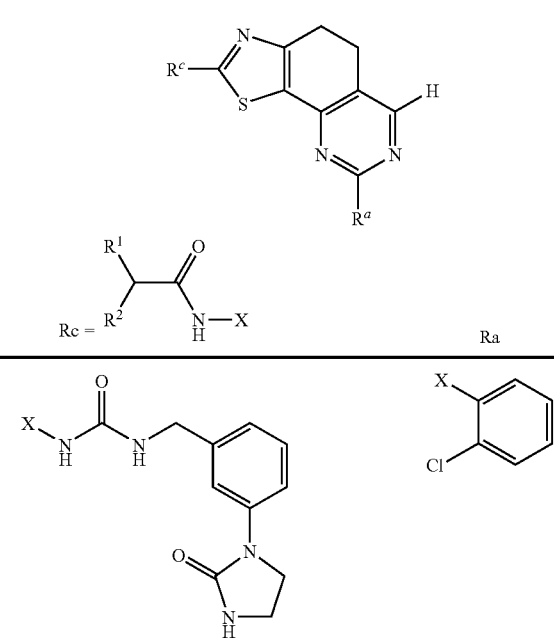 | Ra | mp [° C.] | HPLC method | RT [min] |
|---|---|---|---|---|---|
| 161 | 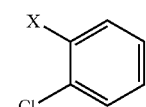 | 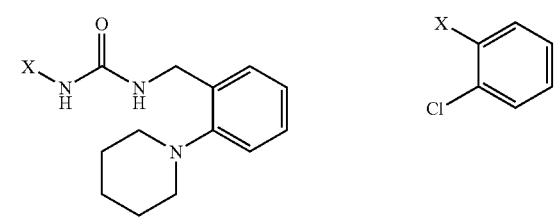 | | C | 3.95 |
| 162 | 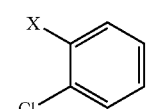 | 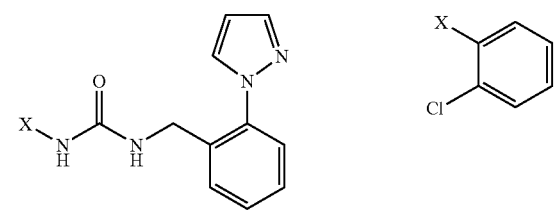 | | C | 3.88 |
| 163 | 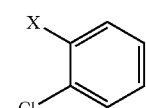 | 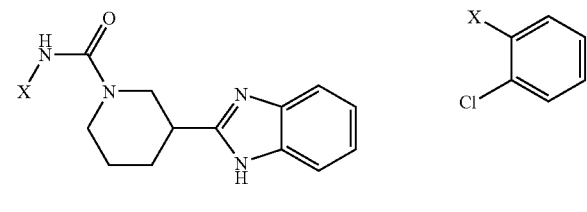 | | C | 4.41 |
| 164 | 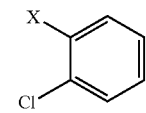 | 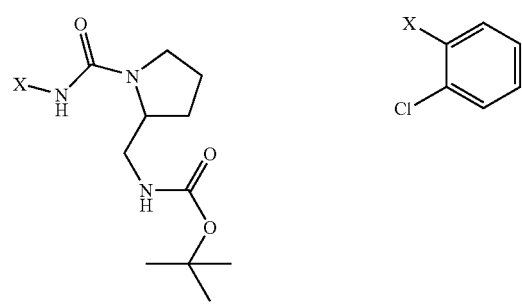 | | C | 3.62 |
| 165 | 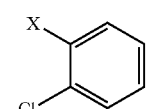 | | | C | 4.54 |

TABLE A-continued

| Ex. No. | Rc = | Ra | mp [° C.] | HPLC method | RT [min] |
|---|---|---|---|---|---|
| 166 | | 2-Cl-C6H4 | | C | 4.58 |
| 167 | | 2-Cl-C6H4 | | C | 4.59 |
| 168 | | 2-Cl-C6H4 | | C | 4.61 |
| 169 | | 2-Cl-C6H4 | | C | 4.63 |
| 170 | | 2-Cl-C6H4 | | C | 4.28 |
| 171 | | 2-Cl-C6H4 | | C | 4.34 |

TABLE A-continued (IA)

| Ex. No. | Rc = | Ra | mp [° C.] | HPLC method | RT [min] |
|---|---|---|---|---|---|
| 172 | | 2-Cl-phenyl | | C | 4.58 |
| 173 | | 2-Cl-phenyl | | C | 3.38 |
| 174 | | 2-Cl-phenyl | | C | 4.84 |
| 175 | | 2-Cl-phenyl | | C | 4.3 |
| 176 | | 2-Cl-phenyl | | C | 4.28 |

TABLE A-continued

| Ex. No. | Rc = | Ra | mp [° C.] | HPLC method | RT [min] |
|---|---|---|---|---|---|
| 177 | (spiro piperidine-imidazolidinone with N-phenyl, N-carboxamide to X) | 2-chlorophenyl (X) | | C | 4.31 |
| 178 | X-NH-C(O)-NH-CH₂-(3-substituted phenyl)-NH-C(O)-O-tBu | 2-chlorophenyl (X) | | C | 4.66 |
| 179 | X-NH-C(O)-NH-CH₂-(3-substituted phenyl)-CH₂-NH-C(O)-O-tBu | 2-chlorophenyl (X) | | C | 4.58 |
| 180 | X-NH-C(O)-NH-CH₂-(3-piperidinyl), N-Boc | 2-chlorophenyl (X) | | C | 4.69 |
| 181 | X-NH-C(O)-NH-CH₂-(2-piperidinyl), N-Boc | 2-chlorophenyl (X) | | C | 4.7 |

TABLE A-continued

| Ex. No. | Rc = [structure with R¹, R², N-X, C=O] | Ra | mp [°C.] | HPLC method | RT [min] |
|---|---|---|---|---|---|
| 182 | X-NH-C(=O)-N(piperidine)-N(imidazolidin-2-one) | 2-chlorophenyl-X | | C | 3.64 |
| 183 | X-NH-C(=O)-N(2,2-dimethyl-3-phenylpyrrolidine) | 2-chlorophenyl-X | | C | 5.14 |
| 184 | X-NH-C(=O)-N(3-phenylpyrrolidine-2-carboxylic acid) | 2-chlorophenyl-X | | C | 4.23 |
| 185 | X-NH-C(=O)-NH-CH₂-(p-phenylene)-CH₂-N(imidazolidin-2-one) | 2-chlorophenyl-X | | C | 3.95 |
| 186 | (1H-indol-3-yl)-piperidin-4-yl-N(C=O)-NH-X | 2-chlorophenyl-X | | C | 4.74 |

TABLE A-continued (IA)

| Ex. No. | Rc = | Ra | mp [° C.] | HPLC method | RT [min] |
|---|---|---|---|---|---|
| 187 | urea-ethyl-imidazolidinone | 2-chlorophenyl | | C | 3.5 |
| 188 | pyrrolidine carboxamide-CH2O-dibromoaniline | 2-chlorophenyl | | C | 5.02 |
| 189 | pyrrolidine carboxamide-dihydroquinazolinone | 2-chlorophenyl | | C | 4.16 |
| 190 | urea-ethyl-N-methylpyrrole | 2-chlorophenyl | | D | 4.07 |
| 191 | piperidine carboxamide-C(OH)-CH2-CO2tBu | 2-chlorophenyl | | C | 4.41 |
| 192 | urea-CH2-phenyl-CH2-dimethylhydantoin | 2-chlorophenyl | | D | 3.79 |

TABLE A-continued

| Ex. No. | Rc = | Ra | mp [° C.] | HPLC method | RT [min] |
|---|---|---|---|---|---|
| 193 | | 2-Cl-phenyl | | C | 3.71 |
| 194 | | 2-Cl-phenyl | | C | 3.72 |
| 195 | | 2-Cl-phenyl | | C | 3.81 |
| 196 | | 2-Cl-phenyl | | C | 4.05 |
| 197 | | 2-Cl-phenyl | | C | 3.68 |
| 198 | | 2-Cl-phenyl | | C | 3.24 |

TABLE A-continued

| Ex. No. | Rc = (structure) | Ra | mp [° C.] | HPLC method | RT [min] |
|---|---|---|---|---|---|
| 199 | pyrrolidine with trifluoroacetamide | 2-Cl-phenyl | | C | 4.04 |
| 200 | ethyl-(1-methylpyrazol-4-yl) urea | 2-Cl-phenyl | | C | 3.72 |
| 201 | 3-(N-cyclohexylcarbamoyl)benzyl urea | 2-Cl-phenyl | | C | 4.54 |
| 202 | ethyl-(4-methylimidazol-2-yl) urea | 2-Cl-phenyl | | D | 2.99 |
| 203 | pyrrolidinyl-methyl-(1-oxo-tetrahydroisoquinolin-2-yl) urea | 2-Cl-phenyl | | C | 4.38 |
| 204 | 3-((N-Boc-N-methylamino)methyl)benzyl urea | 2-Cl-phenyl | | C | 4.82 |

TABLE A-continued

| Ex. No. | Rc = | Ra | mp [° C.] | HPLC method | RT [min] |
|---|---|---|---|---|---|
| 205 | | 2-Cl-phenyl | | C | 4.33 |
| 206 | | 2-Cl-phenyl | | D | 3.24 |
| 207 | | 2-Cl-phenyl | | C | 4.83 |
| 208 | | 2-Cl-phenyl | | C | 3.92 |
| 209 | | 2-Cl-phenyl | | C | 4.63 |
| 210 | | 2-Cl-phenyl | | C | 3.45 |

TABLE A-continued (IA)

| Ex. No. | Rc = | Ra | mp [° C.] | HPLC method | RT [min] |
|---|---|---|---|---|---|
| 211 | (urea-CH(CH3)-phenyl-NH-Boc) | 2-Cl-phenyl | | C | 4.76 |
| 212 | (urea-C(CH3)2-CH2-NH-phenyl-tBu) | 2-Cl-phenyl | | C | 4.55 |
| 213 | (urea-C(CH3)2-CH2-NH-pyrimidin-2-yl) | 2-Cl-phenyl | | C | 3.64 |
| 214 | (urea-(CH2)3-imidazolidin-2-one) | 2-Cl-phenyl | | C | 3.58 |
| 215 | (benzimidazol-1-yl-piperidine-1-carboxamide) | 2-Cl-phenyl | | C | 3.56 |
| 216 | (urea-CH2CH2-pyridin-2-yl) | 2-Cl-phenyl | | C | 3.23 |

TABLE A-continued
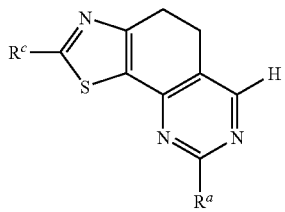
(IA)
| Ex. No. | Rc = | Ra | mp [° C.] | HPLC method | RT [min] |
|---|---|---|---|---|---|
| 217 | | 2-Cl-C6H4 | | C | 3.23 |
| 218 | | 2-Cl-C6H4 | | C | 3.24 |
| 219 | | 2-Cl-C6H4 | | C | 4.43 |
| 220 | | 2-Cl-C6H4 | | C | 4.63 |
| 221 | | 2-Cl-C6H4 | | C | 3.62 |
| 222 | | 2-Cl-C6H4 | | C | 3.46 |
| 223 | | 2-Cl-C6H4 | | C | 4.44 |

TABLE A-continued (IA)

| Ex. No. | Rc = | Ra | mp [° C.] | HPLC method | RT [min] |
|---|---|---|---|---|---|
| 224 | | 2-Cl-C6H4 | | A | 2.76 |
| 225 | | 2-Cl-C6H4 | | | |
| 226 | | 2-Cl-C6H4 | | | |
| 227 | | 2-Cl-C6H4 | | A | 2.84 |
| 228 | | 2-Cl-C6H4 | | A | 2.67 |
| 229 | | 2-Cl-C6H4 | | | |

TABLE A-continued

| Ex. No. | Rc = | Ra | mp [° C.] | HPLC method | RT [min] |
|---|---|---|---|---|---|
| 230 | | 2-Cl-phenyl | | | |
| 231 | | 2-Cl-phenyl | | | |
| 232 | | 2-Cl-phenyl | | | |
| 233 | | 2-Cl-phenyl | | | |
| 234 | | 2-Cl-phenyl | | | |
| 235 | | 2-Cl-phenyl | | | |

TABLE A-continued

| Ex. No. | Rc = | Ra | mp [° C.] | HPLC method | RT [min] |
|---|---|---|---|---|---|
| 236 | | 2-Cl-C6H4 | | | |
| 237 | | 2-Cl-C6H4 | | | |
| 238 | | 2-Cl-C6H4 | 207-209 | | |
| 239 | | 2-Cl-C6H4 | | | |
| 240 | | 2-Cl-C6H4 | | | |
| 241 | | 2-Cl-C6H4 | | | |

TABLE A-continued
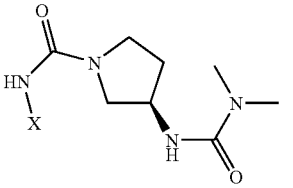
(IA)
| Ex. No. | Rc = 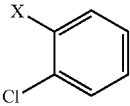 | Ra | mp [° C.] | HPLC method | RT [min] |
|---|---|---|---|---|---|
| 242 | 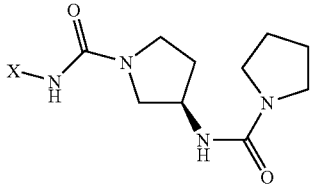 | 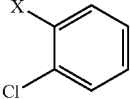 | | | |
| 243 | 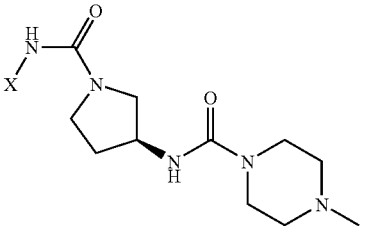 | 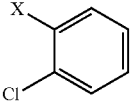 | | | |
| 244 | 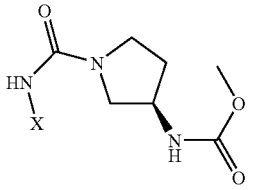 | 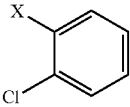 | | | |
| 245 | 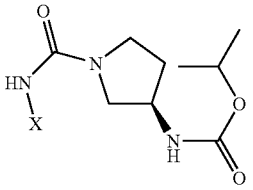 | 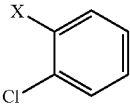 | | | |
| 246 | 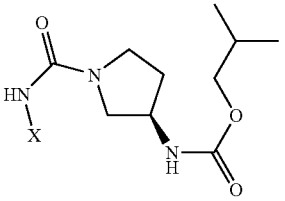 | | | | |
| 247 | 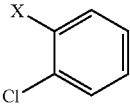 | | | | |

TABLE A-continued

| Ex. No. | Rc = | Ra | mp [° C.] | HPLC method | RT [min] |
|---|---|---|---|---|---|
| 248 | pyrrolidine with X-NH-C(O)- at N1 and NH-S(O)2-N(CH3)2 at C3 | 2-chlorophenyl (X) | | | |
| 249 | pyrrolidine with X-NH-C(O)- at N1 and NH-S(O)2-CH3 at C3 | 2-chlorophenyl (X) | | | |
| 250 | octahydropyrrolo-pyridinone with X-NH-C(O)- | 2-chlorophenyl (X) | 203-204 | | |
| 251 | pyrrolidine with X-NH-C(O)- at N1 and NH-C(O)-CH2-C(CH3)3 at C3 | 2-chlorophenyl (X) | 204-205 | | |
| 252 | 3-(X-NH-C(O)-NH-CH2-)-benzamide with N-isobutyl | 2-chlorophenyl (X) | | | |

TABLE A-continued
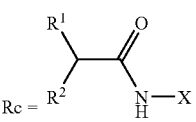
(IA)
| Ex. No. | Rc = 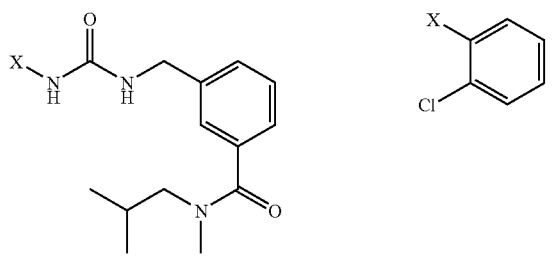 | Ra | mp [° C.] | HPLC method | RT [min] |
|---|---|---|---|---|---|
| 253 | 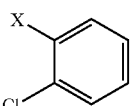 | 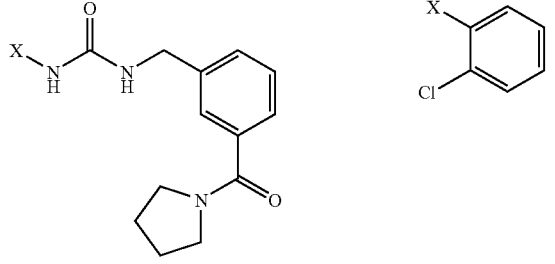 | 217-218 | | |
| 254 | 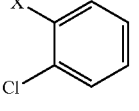 | 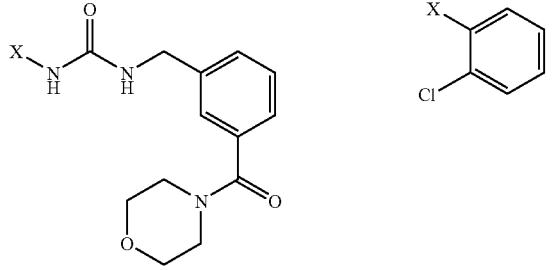 | 178-182 | | |
| 255 | 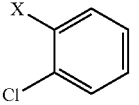 | 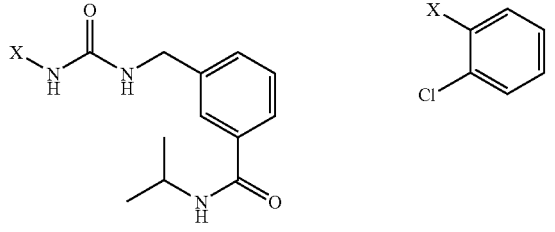 | | | |
| 256 | 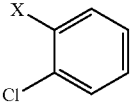 | | | | |

TABLE A-continued
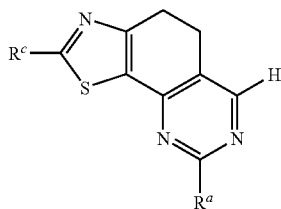
(IA)
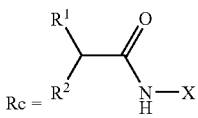
| Ex. No. | Rc = | Ra | mp [° C.] | HPLC method | RT [min] |
|---|---|---|---|---|---|
| 257 | | 2-Cl-C6H4 | 225-226 | | |
| 258 | | 2-Cl-C6H4 | 140-148 | | |
| 259 | | 2-Cl-C6H4 | 204-206 | | |
| 260 | | 2-Cl-C6H4 | 198-199 | A | 2.54 |
| 261 | | 2-Cl-C6H4 | 189-190 | A | 2.63 |

TABLE A-continued

| Ex. No. | Rc = | Ra | mp [° C.] | HPLC method | RT [min] |
|---|---|---|---|---|---|
| 262 | | 2-Cl-C6H4 | 168-169 | A | 2.65 |
| 263 | | 2-Cl-C6H4 | 171-172 | A | 2.78 |
| 264 | | 2-Cl-C6H4 | | B | 1.56 |
| 265 | | 2-Cl-C6H4 | | B | 1.73 |
| 266 | | 2-Cl-C6H4 | | A | 2.65 |
| 267 | | 2-Cl-C6H4 | | A | 2.46 |

TABLE A-continued

| Ex. No. | Rc = | Ra | mp [° C.] | HPLC method | RT [min] |
|---|---|---|---|---|---|
| 268 | | 2-Cl-C6H4 | | A | 2.58 |
| 269 | | 2-Cl-C6H4 | | A | 2.48 |
| 270 | | 2-Cl-C6H4 | | B | 1.67 |
| 271 | | 2-Cl-C6H4 | | B | 1.54 |
| 272 | | 2-Cl-C6H4 | | B | 1.74 |
| 273 | | 2-Cl-C6H4 | | B | 1.86 |

TABLE A-continued (IA)

| Ex. No. | Rc = structure with R¹, R² and N-X amide | Ra | mp [° C.] | HPLC method | RT [min] |
|---|---|---|---|---|---|
| 274 | X-NH-C(O)-NH-CH₂-(3-acetamidophenyl) | 2-Cl-C₆H₄- | | | |
| 275 | X-NH-C(O)-NH-CH₂-(3-isobutyramidophenyl) | 2-Cl-C₆H₄- | | | |
| 276 | X-NH-C(O)-NH-CH₂-(3-(3-methylbutanamido)phenyl) | 2-Cl-C₆H₄- | | A | 2.96 |
| 277 | X-NH-C(O)-NH-CH₂-(3-(cyclopentanecarboxamido)phenyl) | 2-Cl-C₆H₄- | | A | 3.03 |

TABLE A-continued
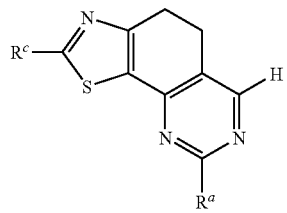
(IA)
| Ex. No. | Rc = <br> ![Rc structure] | Ra | mp [° C.] | HPLC method | RT [min] |
|---|---|---|---|---|---|
| 278 | 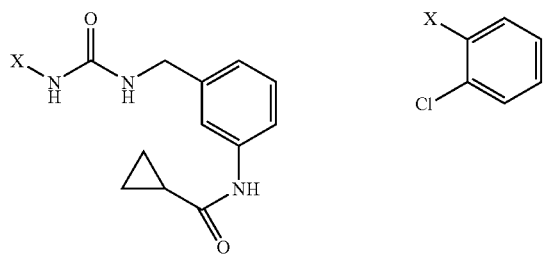 | ![2-Cl phenyl] | | A | 2.82 |
| 279 | 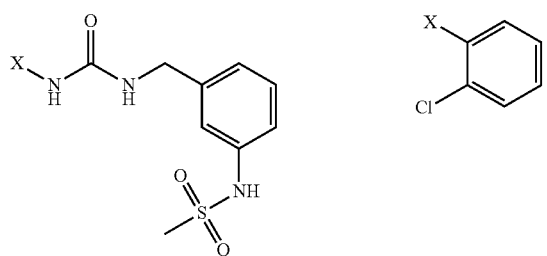 | ![2-Cl phenyl] | | | |
| 280 | 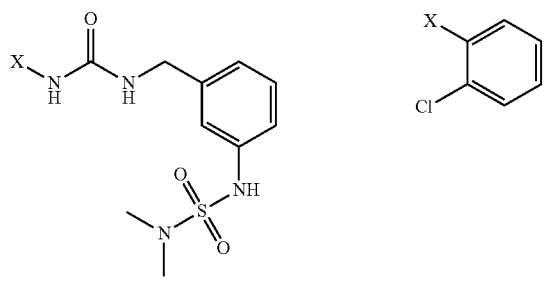 | ![2-Cl phenyl] | | | |
| 281 | 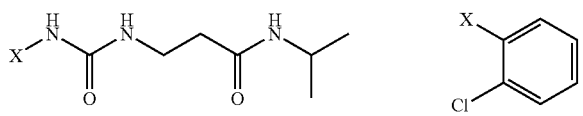 | ![2-Cl phenyl] | | | |
| 282 | 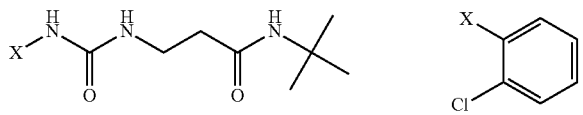 | ![2-Cl phenyl] | | | |
| 283 | 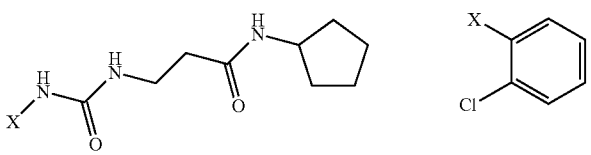 | ![2-Cl phenyl] | | | |

TABLE A-continued
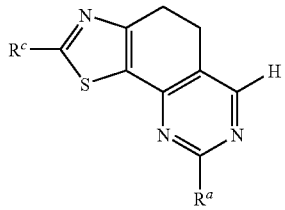
| Ex. No. | Rc = | Ra | mp [° C.] | HPLC method | RT [min] |
|---|---|---|---|---|---|
| 284 | | 2-Cl-C6H4 | | | |
| 285 | | 2-Cl-C6H4 | | | |
| 286 | | 2-Cl-C6H4 | | A | 2.90 |
| 287 | | 2-Cl-C6H4 | | | |
| 288 | | 2-Cl-C6H4 | | A | 2.58 |
| 289 | | 2-Cl-C6H4 | | A | 2.80 |
| 290 | | 2-Cl-C6H4 | | A | 2.57 |
| 291 | | 2-Cl-C6H4 | | A | 2.42 |
| 292 | | 2-Cl-C6H4 | | | |

TABLE A-continued
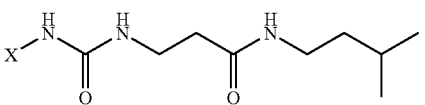
(IA)
| Ex. No. | Rc = 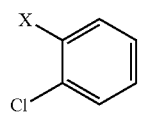 | Ra | mp [° C.] | HPLC method | RT [min] |
|---|---|---|---|---|---|
| 293 | 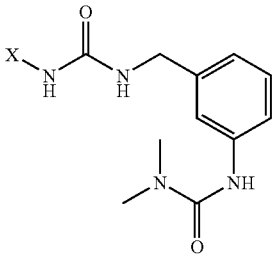 | 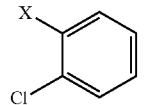 | | A | 2.77 |
| 294 | 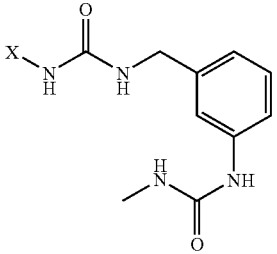 | 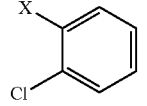 | | | |
| 295 | 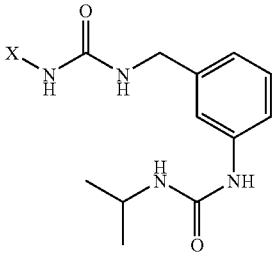 | 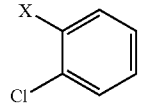 | | | |
| 296 | 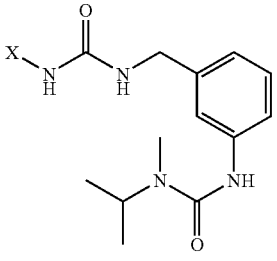 | 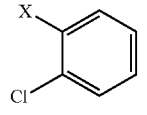 | | | |
| 297 | | | | | |

TABLE A-continued

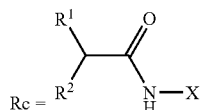

| Ex. No. | Rc = | Ra | mp [° C.] | HPLC method | RT [min] |
|---|---|---|---|---|---|
| 298 | 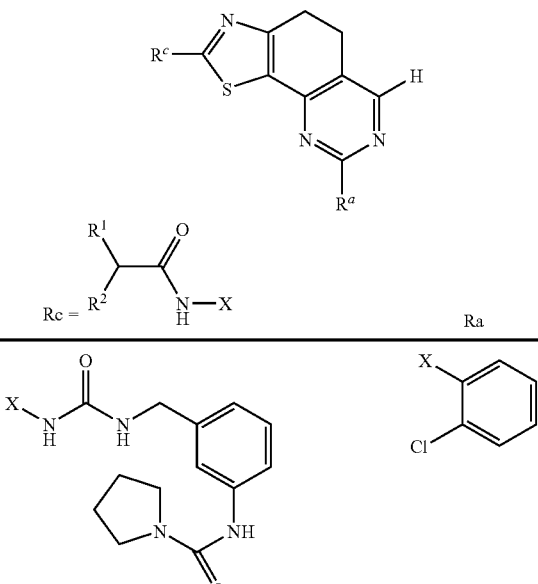 | 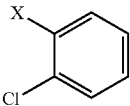 | | | |
| 299 | 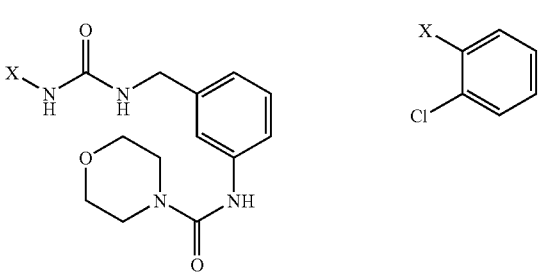 | 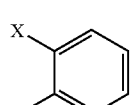 | | | |

Biological Test

The compounds of formula (I) mentioned by way of example are characterised by an affinity for PI3-kinase, i.e. in the test by an $IC_{50}$ value of below 800 nmol/liter.

In order to determine the inhibitory activity of the compounds on PI3Kγ, an in-vitro kinase assay was used. The expression and purification of $G\beta_1\gamma_2$-His and p101-GST/p110γ from Sf9-cells (*Spodoptera frugiperda* 9) has already been described (Maier et al., J. Biol. Chem. 1999 (274) 29311-29317). Alternatively, the following method was used to determine the activity:

10 μl of the compound to be tested were placed on 96 well PVDF filter plates (0.45 μM) and incubated for 20 min with 30 μl lipid vesicles ($PIP_2$ (0.7 μg/well), phosphatidylethanolamine (7.5 μg/well), phosphatidylserine (7.5 μg/well), sphingomyelin (0.7 μg/well) and phosphatidylcholine (3.2 μg/well)) which contained 1-3 ng PI3K☐ and 20-60 ng G☐$_1$☐$_2$-His. The reaction was started by the addition of 10 μl reaction buffer (40 mM Hepes, pH 7.5, 100 mM NaCl, 1 mM EGTA, 1 mM ☐-glycerophosphate, 1 mM DTT, 7 mM $MgCl_2$ and 0.1% BSA; 1 μM ATP and 0.2 μCi [☐-$^{33}$P]-ATP) and incubated for 120 min at ambient temperature. The reaction solution was sucked through the filters by the application of a vacuum and washed with 200 μl PBS. After the plates had been dried at 50° C. the radioactivity remaining in the plates was determined after the addition of 50 μl scintillation liquid using a Top-Count measuring device.

Ranges of Indications

It has been found that the compounds of formula (I) are characterised by a variety of possible applications in the therapeutic field. Particular mention should be made of those applications for which the compounds of formula (I) according to the invention are preferably used by virtue of their pharmaceutical activity as PI3-kinase modulators.

Generally speaking, these are diseases in whose pathology PI3-kinases are implicated, particularly inflammatory and allergic diseases. Particular mention should be made of inflammatory and allergic respiratory complaints, inflammatory diseases of the gastrointestinal tract, inflammatory diseases of the motor apparatus, inflammatory and allergic skin diseases, inflammatory eye diseases, diseases of the nasal mucosa, inflammatory or allergic ailments which involve autoimmune reactions or inflammation of the kidneys. The treatment may be symptomatic, adaptive, curative or preventative.

Respiratory complaints deserving special mention would be chronic and/or obstructive respiratory complaints. The compounds of formula 1 according to the invention may, by virtue of their pharmacological properties, bring about a reduction in
   Tissue damage
   Inflammation of the airways
   bronchial hyperreactivity
   the process of reconstruction of the lung as a result of inflammation
   worsening of the disease (progression).

The compounds according to the invention are particularly preferred for preparing a medicament for the treatment of chronic bronchitis, acute bronchitis, bronchitis caused by bacterial or viral infection or fungi or helminths, allergic bronchitis, toxic bronchitis, chronic obstructive pulmonary disease (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases such as e.g. pulmonary fibrosis, asbestosis and silicosis and alveolitis; hyperreactive airways, nasal polyps, pulmonary oedema such as e.g. toxic pulmonary oedema and ARDS/IRDS, pneumonitis of different origins, e.g. radiation-induced or caused by aspiration or infectious pneumonitis, collagenoses such as lupus erythematodes, systemic scleroderma, sarcoidosis or Boeck's disease.

The compounds of formula (I) are also suitable for the treatment of diseases of the skin, such as e.g. psoriasis, contact dermatitis, atopic dermatitis, alopecia areata (circular hair loss), erythema exsudativum multiforme (Stevens-Johnson Syndrome), dermatitis herpetiformis, sclerodermy, vitiligo, nettle rash (urticaria), lupus erythematodes, follicular and surface pyodermy, endogenous and exogenous acne, acne rosacea and other inflammatory or allergic or proliferative skin diseases.

Moreover, the compounds of formula (I) are suitable for therapeutic use in cases of inflammatory or allergic complaints which involve autoimmune reactions, such as e.g. inflammatory bowel diseases, e.g. Crohn's disease or ulcerative colitis; diseases of the arthritis type, such as e.g. rheumatoid or psoriatic arthritis, osteoarthritis, rheumatoid spondylitis and other arthritic conditions or multiple sclerosis.

The following general inflammatory or allergic diseases may also be mentioned, which can be treated with medicaments containing compounds of formula (I):

inflammation of the eye, such as e.g. conjunctivitis of various kinds, e.g. caused by infections with fungi or bacteria, allergic conjunctivitis, irritable conjunctivitis, drug-induced conjunctivitis, keratitis, uveitis diseases of the nasal mucosa, such as e.g. allergic rhinitis/sinusitis or nasal polyps inflammatory or allergic conditions, such as e.g. systemic lupus erythematodes, chronic hepatitis, kidney inflammations such as glomerulonephritis, interstitial nephritis or idiopathic nephrotic syndrome.

Other diseases which may be treated with a drug containing compounds of formula (I) on the basis of their pharmacological activity include toxic or septic shock syndrome, atherosclerosis, middle ear infections (otitis media), hypertrophy of the heart, cardiac insufficiency, stroke, ischaemic reperfusion injury or neurodegenerative diseases such as Parkinson's disease or Alzheimer's.

Combinations

The compounds of formula (I) may be used on their own or in combination with other active substances of formula (I). If desired the compounds of formula (I) may also be used in combination with W, where W denotes a pharmacologically active substance and (for example) is selected from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors, preferably PI3-☐Kinase inhibitors. Moreover, double or triple combinations of W may be combined with the compounds of formula (I). Combinations of W might be, for example:

W denotes a betamimetic, combined with an active substance selected from among the anticholinergics, corticosteroids, PDE4-inhibitors, EGFR-inhibitors and LTD4-antagonists, W denotes an anticholinergic, combined with an active substance selected from among the betamimetics, corticosteroids, PDE4-inhibitors EGFR-inhibitors and LTD4-antagonists, W denotes a corticosteroid, combined with an active substance selected from among the PDE4-inhibitors, EGFR-inhibitors and LTD4-antagonists W denotes a PDE4-inhibitor, combined with an active substance selected from among the EGFR-inhibitors and LTD4-antagonists W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5.6-diethyl-indan-2-ylamino)-1-hydroxy-ethyl]-8-hydroxy-1H-quinoline-2-one 4-hydroxy-7-[2-{[2-{[3-(2-phenylethoxy)propyl]sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazole-3-yl]-2-methyl-2-butylamino}ethanol 5-hydroxy-8-(1-hydroxy-2-isopropylaminobutyl)-2H-1,4-benzoxazin-3-(4H)-on 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2.4.6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1.1 dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other specified compounds are:
tropenol 2,2-diphenylpropionate methobromide
scopine 2,2-diphenylpropionate methobromide
scopine 2-fluoro-2,2-diphenylacetate methobromide
tropenol 2-fluoro-2,2-diphenylacetate methobromide
tropenol 3,3',4,4'-tetrafluorobenzilate methobromide
scopine 3,3',4,4'-tetrafluorobenzilate methobromide
tropenol 4,4'-difluorobenzilate methobromide
scopine 4,4'-difluorobenzilate methobromide
tropenol 3,3'-difluorobenzilate methobromide
scopine 3,3'-difluorobenzilate methobromide
tropenol 9-hydroxy-fluorene-9-carboxylate methobromide
tropenol 9-fluoro-fluorene-9-carboxylate methobromide
scopine 9-hydroxy-fluorene-9-carboxylate methobromide
scopine 9-fluoro-fluorene-9-carboxylate methobromide
tropenol 9-methyl-fluorene-9-carboxylate methobromide
scopine 9-methyl-fluorene-9-carboxylate methobromide
cyclopropyltropine benzilate methobromide
cyclopropyltropine 2,2-diphenylpropionate methobromide
cyclopropyltropine 9-hydroxy-xanthene-9-carboxylate methobromide
cyclopropyltropine 9-methyl-fluorene-9-carboxylate methobromide
cyclopropyltropine 9-methyl-xanthene-9-carboxylate methobromide
cyclopropyltropine 9-hydroxy-fluorene-9-carboxylate methobromide
cyclopropyltropine methyl 4,4'-difluorobenzilate methobromide
tropenol 9-hydroxy-xanthene-9-carboxylate methobromide
scopine 9-hydroxy-xanthene-9-carboxylate methobromide
tropenol 9-methyl-xanthene-9-carboxylate-methobromide
scopine 9-methyl-xanthene-9-carboxylate-methobromide
tropenol 9-ethyl-xanthene-9-carboxylate methobromide
tropenol 9-difluoromethyl-xanthene-9-carboxylate methobromide
scopine 9-hydroxymethyl-xanthene-9-carboxylate methobromide As corticosteroids it is preferable to use compounds selected from among prednisolone, prednisone, butixocort propionate, flunisolide, beclomethasone, triamcinolone, budesonide, fluticasone, mometasone, ciclesonide, rofleponide, dexamethasone, betamethasone, deflazacort, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothioate (S)-(2-oxo-tetrahydro-furan-3S-yl)6,9-difluoro-11-hydroxy-16-methyl-3-oxo-17-propionyloxy-androsta-1,4-diene-17-carbothioate, etiprednol-dichloroacetate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxy-phenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4.3-a]pyridine 9-cyclopentyl-5,6-dihydro-7-ethyl-3-(tert-butyl)-9H-pyrazolo[3,4-c]-1,2,4-triazolo[4.3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and
1-(((R)-3-(2-(6,7-difluoro-2-quinolinyl)ethenyl)phenyl)-3-(2-(2-hydroxy-2-propyl)phenyl)thio)methylcyclopropane-acetic acid,
1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid
[2-[[2-(4-tert-butyl-2-thiazolyl)-5-benzofuranyl]oxymethyl]phenyl]acetic acid
optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and
4-[(3-chloro-4-fluorophenyl)amino]-6-{[4-(morpholin-4-yl)-1-oxo-2-buten-1-yl]-amino}-7-cyclopropylmethoxy-quinazoline
4-[(3-chloro-4-fluorophenyl)amino]-6-{[4-(N,N-diethylamino)-1-oxo-2-buten-1-yl]amino}-7-cyclopropyl-methoxy-quinazoline
4-[(3-chloro-4-fluorophenyl)amino]-6-{[4-(N,N-dimethylamino)-1-oxo-2-buten-1-yl]amino}-7-cyclopropyl-methoxy-quinazoline
4-[(R)-(1-phenyl-ethyl)amino]-6-{[4-(morpholin-4-yl)-1-oxo-2-buten-1-yl]amino}-7-cyclopentyloxy-quinazoline
4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline
4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline
4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline
4-[(3-chloro-4-fluoro-phenyl)amino]-6-[2-((S)-6-methyl-2-oxo-morpholin-4-yl)-ethoxy]-7-methoxy-quinazoline
4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline
4-[(3-chloro-4-fluorophenyl)amino]-6-{[4-(N,N-dimethylamino)-1-oxo-2-buten-1-yl]amino}-7-cyclopentyloxy-quinazoline
4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline
4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline
4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline
4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline
4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline
4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline
4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline
4-[(3-chloro-4-fluorophenyl)amino]-6-{[4-(N-cyclopropyl-N-methyl-amino)-1-oxo-2-buten-1-yl]amino}-7-cyclopentyloxy-quinazoline
4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline
4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline
4-[(3-ethynyl-phenyl)amino]-6.7-bis-(2-methoxy-ethoxy)-quinazoline
4-[(3-chloro-4-fluorophenyl)amino]-7-[3-(morpholin-4-yl)-propyloxy]-6-[(vinyl-carbonyl)amino]-quinazoline
4-[(R)-(1-phenyl-ethyl)amino]-6-(4-hydroxy-phenyl)-7H-pyrrolo[2,3-d]pyrimidine
3-cyano-4-[(3-chloro-4-fluorophenyl)amino]-6-{[4-(N,N-dimethylamino)-1-oxo-2-buten-1-yl]amino}-7-ethoxy-quinoline
4-{[3-chloro-4-(3-fluoro-benzyloxy)-phenyl]amino}-6-(5-{[(2-methanesulphonyl-ethyl)amino]methyl}-furan-2-yl)quinazoline
4-[(R)-(1-phenyl-ethyl)amino]-6-{[4-((R)-6-methyl-2-oxo-morpholin-4-yl)-1-oxo-2-buten-1-yl]amino}-7-methoxy-quinazoline
4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline
4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline
4-[(3-ethynyl-phenyl)amino]-6-{[4-(5.5-dimethyl-2-oxo-morpholin-4-yl)-1-oxo-2-buten-1-yl]amino}-quinazoline
4-[(3-chloro-4-fluoro-phenyl)amino]-6-[2-(2.2-dimethyl-6-oxo-morpholin-4-yl)-ethoxy]-7-methoxy-quinazoline
4-[(3-chloro-4-fluoro-phenyl)amino]-6-[2-(2.2-dimethyl-6-oxo-morpholin-4-yl)-ethoxy]-7-[(R)-(tetrahydrofuran-2-yl)methoxy]-quinazoline
4-[(3-chloro-4-fluoro-phenyl)amino]-7-[2-(2.2-dimethyl-6-oxo-morpholin-4-yl)-ethoxy]-6-[(S)-(tetrahydrofuran-2-yl)methoxy]-quinazoline
4-[(3-chloro-4-fluoro-phenyl)amino]-6-{2-[4-(2-oxo-morpholin-4-yl)-piperidin-1-yl]-ethoxy}-7-methoxy-quinazoline
4-[(3-chloro-4-fluoro-phenyl)amino]-6-[1-(tert.-butyloxycarbonyl)-piperidin-4-yloxy]-7-methoxy-quinazoline
4-[(3-chloro-4-fluoro-phenyl)amino]-6-(trans-4-amino-cyclohexan-1-yloxy)-7-methoxy-quinazoline
4-[(3-chloro-4-fluoro-phenyl)amino]-6-(trans-4-methanesulphonylamino-cyclohexan-1-yloxy)-7-methoxy-quinazoline
4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline
4-[(3-chloro-4-fluoro-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(methoxymethyl)carbonyl]-piperidin-4-yloxy}-7-methoxy-quinazoline
4-[(3-chloro-4-fluoro-phenyl)amino]-6-(piperidin-3-yloxy)-7-methoxy-quinazoline
4-[(3-chloro-4-fluoro-phenyl)amino]-6-[1-(2-acetylamino-ethyl)-piperidin-4-yloxy]-7-methoxy-quinazoline
4-[(3-chloro-4-fluoro-phenyl)amino]-6-(tetrahydropyran-4-yloxy)-7-ethoxy-quinazoline
4-[(3-chloro-4-fluoro-phenyl)amino]-6-((S)-tetrahydrofuran-3-yloxy)-7-hydroxy-quinazoline
4-[(3-chloro-4-fluoro-phenyl)amino]-6-(tetrahydropyran-4-yloxy)-7-(2-methoxy-ethoxy)-quinazoline
4-[(3-chloro-4-fluoro-phenyl)amino]-6-{trans-4-[(dimethylamino)sulphonylamino]-cyclohexan-1-yloxy}-7-methoxy-quinazoline
4-[(3-chloro-4-fluoro-phenyl)amino]-6-{trans-4-[(morpholin-4-yl)carbonylamino]-cyclohexan-1-yloxy}-7-methoxy-quinazoline
4-[(3-chloro-4-fluoro-phenyl)amino]-6-{trans-4-[(morpholin-4-yl)sulphonylamino]-cyclohexan-1-yloxy}-7-methoxy-quinazoline
4-[(3-chloro-4-fluoro-phenyl)amino]-6-(tetrahydropyran-4-yloxy)-7-(2-acetylamino-ethoxy)-quinazoline
4-[(3-chloro-4-fluoro-phenyl)amino]-6-(tetrahydropyran-4-yloxy)-7-(2-methanesulphonylamino-ethoxy)-quinazoline
4-[(3-chloro-4-fluoro-phenyl)amino]-6-{1-[(piperidin-1-yl)carbonyl]-piperidin-4-yloxy}-7-methoxy-quinazoline
4-[(3-chloro-4-fluoro-phenyl)amino]-6-(1-aminocarbonylmethyl-piperidin-4-yloxy)-7-methoxy-quinazoline
4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline
4-[(3-chloro-4-fluoro-phenyl)amino]-6-(trans-4-ethanesulphonylamino-cyclohexan-1-yloxy)-7-methoxy-quinazoline
4-[(3-chloro-4-fluoro-phenyl)amino]-6-(1-methanesulphonyl-piperidin-4-yloxy)-7-ethoxy-quinazoline
4-[(3-chloro-4-fluoro-phenyl)amino]-6-(1-methanesulphonyl-piperidin-4-yloxy)-7-(2-methoxy-ethoxy)-quinazoline
4-[(3-chloro-4-fluoro-phenyl)amino]-6-[1-(2-methoxy-acetyl)-piperidin-4-yloxy]-7-(2-methoxy-ethoxy)-quinazoline
4-[(3-chloro-4-fluoro-phenyl)amino]-6-(cis-4-acetylamino-cyclohexan-1-yloxy)-7-methoxy-quinazoline
4-[(3-ethynyl-phenyl)amino]-6-[1-(tert.-butyloxycarbonyl)-piperidin-4-yloxy]-7-methoxy-quinazoline
4-[(3-ethynyl-phenyl)amino]-6-(tetrahydropyran-4-yloxy)-7-methoxy-quinazoline
4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline
4-[(3-chloro-4-fluoro-phenyl)amino]-6-{cis-4-[(morpholin-4-yl)carbonylamino-cyclohexan-1-yloxy}-7-methoxy-quinazoline
4-[(3-chloro-4-fluoro-phenyl)amino]-6-{1-[2-(2-oxopyrrolidin-1-yl)ethyl]-piperidin-4-yloxy}-7-methoxy-quinazoline
4-[(3-chloro-4-fluoro-phenyl)amino]-6-{1-[(morpholin-4-yl)carbonyl]-piperidin-4-yloxy}-7-(2-methoxy-ethoxy)-quinazoline
4-[(3-ethynyl-phenyl)amino]-6-(1-acetyl-piperidin-4-yloxy)-7-methoxy-quinazoline
4-[(3-ethynyl-phenyl)amino]-6-(1-methyl-piperidin-4-yloxy)-7-methoxy-quinazoline
4-[(3-ethynyl-phenyl)amino]-6-(1-methanesulphonyl-piperidin-4-yloxy)-7-methoxy-quinazoline
4-[(3-chloro-4-fluoro-phenyl)amino]-6-(1-methyl-piperidin-4-yloxy)-7(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxyethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-N-methyl-amino)-cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2.2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptine, cabergoline, alpha-dihydroergokryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimethindene, clemastine, bamipine, cexchlorpheniramine, pheniramine, doxylamine, chlorophenoxamine, dimenhydrinate, diphenhydramine, promethazine, ebastine, desloratadine and meclozine, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The PAF-antagonists used are preferably compounds selected from among 4-(2-chlorophenyl)-9-methyl-2-[3(4-morpholinyl)-3-propanon-1-yl]-6H-thieno-[3,2-f]-[1,2,4]triazolo[4,3-a][1,4]diazepine 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepine, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The PI3-kinase-δ-inhibitors used are preferably compounds selected from among: IC87114-(6-aminopurin-9-ylmethyl)-3-(2-chlorophenyl)-6.7-dimethoxy-3H-quinazolin-4-one; 2-(6-aminopurin-o-ylmethyl)-6-bromo-3-(2-chlorophenyl)-3H-quinazolin-4-one; 2-(6-aminopurin-o-ylmethyl)-3-(2-chlorophenyl)-7-fluoro-3H-quinazolin-4-one; 2-(6-aminopurin-9-ylmethyl)-6-chloro-3-(2-chlorophenyl)-3H-quinazolin-4-one; 2-(6-aminopurin-9-ylmethyl)-3-(2-chlorophenyl)-5-fluoro-3H-quinazolin-4-one; 2-(6-aminopurin-o-ylmethyl)-5-chloro-3-(2-chlorophenyl)-3H-quinazolin-4-one; 2-(6-aminopurin-9-ylmethyl)-3-(2-chlorophenyl)-5-methyl-3H-quinazolin-4-one; 2-(6-aminopurin-9-ylmethyl)-8-chloro-3-(2-chlorophenyl)-3H-quinazolin-4-one; 2-(6-aminopurin-9-ylmethyl)-3-biphenyl-2-yl-5-chloro-3H-quinazolin-4-one; 5-chloro-2-(9H-purin-6-ylsulphanylmethyl)-3-o-tolyl-3H-quinazolin-4-one; 5-chloro-3-(2-fluorophenyl)-2-(9H-purin-6-yl-sulphanylmethyl)-3H-quinazolin-4-one; 2-(6-aminopurin-9-ylmethyl)-5-chloro-3-(2-fluorophenyl)-3H-quinazolin-4-one; 3-biphenyl-2-yl-5-chloro-2-(9H-purin-6-ylsulphanylmethyl)-3H-quinazolin-4-one; 5-chloro-3-(2-methoxyphenyl)-2-(9H-purin-6-yl-sulphanylmethyl)-3H-quinazolin-4-one; 3-(2-chlorophenyl)-5-fluoro-2-(9H-purin-6-yl-sulphanylmethyl)-3H-quinazolin-4-one; 3-(2-chlorophenyl)-6.7-dimethoxy-2-(9H-purin-6-yl-sulphanylmethyl)-3H-quinazolin-4-one; 6-bromo-3-(2-chlorophenyl)-2-(9H-purin-6-yl-sulphanylmethyl)-3H-quinazolin-4-one; 3-(2-chlorophenyl)-8-trifluoromethyl-2-(9H-purin-6-ylsulphanylmethyl)-3H-quinazolin-4-one; 3-(2-chlorophenyl)-2-(9H-purin-6-ylsulphanylmethyl)-3H-benzo[g]quinazolin-4-one; 6-chloro-3-(2-chlorophenyl)-2-(9H-purin-6-yl-sulphanylmethyl)-3H-quinazolin-4-one; 8-chloro-3-(2-chlorophenyl)-2-(9H-purin-6-yl-sulphanylmethyl)-3H-quinazolin-4-one; 3-(2-chlorophenyl)-7-fluoro-2-(9H-purin-6-yl-sulphanylmethyl)-3H-quinazolin-4-one; 3-(2-chlorophenyl)-7-nitro-2-(9H-purin-6-yl-sulphanylmethyl)-3H-quinazolin-4-one; 3-(2-chlorophenyl)-6-hydroxy-2-(9H-purin-6-yl-sulphanylmethyl)-3H-quinazolin-4-one; 5-chloro-3-(2-chlorophenyl)-2-(9H-purin-6-yl-sulphanylmethyl)-3H-quinazolin-4-one; 3-(2-chlorophenyl)-5-methyl-2-(9H-purin-6-yl-sulphanylmethyl)-3H-quinazolin-4-one; 3-(2-chlorophenyl)-6.7-difluoro-2-(9H-purin-6-yl-sulphanylmethyl)-3H-quinazolin-4-one; 3-(2-chlorophenyl)-6-fluoro-2-(9H-purin-6-yl-sulphanylmethyl)-3H-quinazolin-4-one; 2-(6-aminopurin-9-ylmethyl)-3-(2-isopropylphenyl)-5-methyl-3H-quinazolin-4-one; 2-(6-aminopurin-9-ylmethyl)-5-methyl-3-o-tolyl-3H-quinazolin-4-one; 3-(2-fluorophenyl)-5-methyl-2-(9H-purin-6-yl-sulphanylmethyl)-3H-quinazolin-4-one; 2-(6-aminopurin-9-ylmethyl)-5-chloro-3-o-tolyl-3H-quinazolin-4-one; 2-(6-aminopurin-9-ylmethyl)-5-chloro-3-(2-methoxy-phenyl)-3H-quinazolin-4-one; 2-(2-amino-9H-purin-6-ylsulphanylmethyl)-3-cyclopropyl-5-methyl-3H-quinazolin-4-one; 3-cyclopropylmethyl-5-methyl-2-(9H-purin-6-ylsulphanylmethyl)-3H-quinazolin-4-one; 2-(6-aminopurin-9-ylmethyl)-3-cyclopropylmethyl-5-methyl-3H-quinazolin-4-one; 2-(2-amino-9H-purin-6-ylsulphanylmethyl)-3-cyclopropylmethyl-5-methyl-3H-quinazolin-4-one; 5-methyl-3-phenethyl-2-(9H-purin-6-ylsulphanylmethyl)-3H-quinazolin-4-one; 2-(2-amino-9H-purin-6-ylsulphanylmethyl)-5-methyl-3-phenethyl-3H-quinazolin-4-one; 3-cyclopentyl-5-methyl-2-(9H-purin-6-ylsulphanylmethyl)-3H-quinazolin-4-one; 2-(6-aminopurin-9-ylmethyl)-3-cyclopentyl-5-methyl-3H-quinazolin-4-one; 3-(2-chloropyridin-3-yl)-5-methyl-2-(9H-purin-6-ylsulphanylmethyl)-3H-quinazolin-4-one; 2-(6-aminopurin-9-ylmethyl)-3-(2-chloropyridin-3-yl)-5-methyl-3H-quinazolin-4- one; 3-methyl-4-[5-methyl-4-oxo-2-(9H-purin-6-ylsulphanylmethyl)-4H-quinazolin-3-yl]-benzoic acid; 3-cyclopropyl-5-methyl-2-(9H-purin-6-ylsulphanylmethyl)-3H-quinazolin-4-one; 2-(6-aminopurin-9-ylmethyl)-3-cyclopropyl-5-methyl-3H-quinazolin-4-one; 5-methyl-3-(4-nitrobenzyl)-2-(9H-purin-6-ylsulphanylmethyl)-3H-quinazolin-4-one; 3-cyclohexyl-5-methyl-2-(9H-purin-6-ylsulphanylmethyl)-3H-quinazolin-4-one; 2-(6-aminopurin-9-ylmethyl)-3-cyclohexyl-5-methyl-3H-quinazolin-4-one; 2-(2-amino-9H-purin-6-ylsulphanylmethyl)-3-cyclo-hexyl-5-methyl-3H-quinazolin-4-one; 5-methyl-3-(E-2-phenylcyclopropyl)-2-(9H-purin-6-ylsulphanylmethyl)-3H-quinazolin-4-one; 3-(2-chlorophenyl)-5-fluoro-2-[(9H-purin-6-ylamino)methyl]-3H-quinazolin-4-one; 2-[(2-amino-9H-purin-6-ylamino)methyl]-3-(2-chlorophenyl)-5-fluoro-3H-quinazolin-4-one; 5-methyl-2-[(9H-purin-6-ylamino)methyl]-3-o-tolyl-3H-quinazolin-4-one; 2-[(2-amino-9H-purin-6-ylamino)methyl]-5-methyl-3-o-tolyl-3H-quinazolin-4-one; 2-[(2-fluoro-9H-purin-6-ylamino)methyl]-5-methyl-3-o-tolyl-3H-quinazolin-4-one; (2-chlorophenyl)-dimethylamino-(9H-purin-6-ylsulphanylmethyl)-3H-quinazolin-4-one; 5-(2-benzyloxyethoxy)-3-(2-chlorophenyl)-2-(9H-purin-6-ylsulphanylmethyl)-3H-quinazolin-4-one; 3-(2-chlorophenyl)-5-fluoro-4-oxo-3,4-dihydro-quinazolin-2-ylmethyl 6-aminopurine-9-carboxylate; N-[3-(2-chlorophenyl)-5-fluoro-4-oxo-3,4-dihydro-quinazolin-2-ylmethyl]-2-(9H-purin-6-ylsulphanyl)-acetamide; 2-[1-(2-fluoro-9H-purin-6-ylamino)ethyl]-5-methyl-3-o-tolyl-3H-quinazolin-4-one; 5-methyl-2-[1-(9H-purin-6-ylamino)ethyl]-3-o-tolyl-3H-quinazolin-4-one; 2-(6-dimethylaminopurin-9-ylmethyl)-5-methyl-3-o-tolyl-3H-quinazolin-4-one; 5-methyl-2-(2-methyl-6-oxo-1,6-dihydro-purin-7-ylmethyl)-3-o-tolyl-3H-quinazolin-4-one; 5-methyl-2-(2-methyl-6-oxo-1,6-dihydro-purin-9-ylmethyl)-3-o-tolyl-3H-quinazolin-4-one; 2-(amino-dimethylaminopurin-9-ylmethyl)-5-methyl-3-o-tolyl-3H-quinazolin-4-one; 2-(2-amino-9H-purin-6-ylsulphanylmethyl)-5-methyl-3-o-tolyl-3H-quinazolin-4-one; 2-(4-amino-1,3,5-triazin-2-ylsulphanylmethyl)-5-methyl-3-o-tolyl-3H-quinazolin-4-one; 5-methyl-2-(7-methyl-7H-purin-6-ylsulphanylmethyl)-3-o-tolyl-3H-quinazolin-4-one; 5-methyl-2-(2-oxo-1,2-dihydro-pyrimidin-4-ylsulphanylmethyl)-3-o-tolyl-3H-quinazolin-4-one; 5-methyl-2-purin-7-ylmethyl-3-o-tolyl-3H-quinazolin-4-one; 5-methyl-2-purin-9-ylmethyl-3-o-tolyl-3H-quinazolin-4-one; 5-methyl-2-(9-methyl-9H-purin-6-ylsulphanylmethyl)-3-o-tolyl-3H-quinazolin-4-one; 2-(2,6-diamino-pyrimidin-4-ylsulphanylmethyl)-5-methyl-3-o-tolyl-3H-quinazolin-4-one; 5-methyl-2-(5-methyl-[1,2,4]triazolo[1.5-a]pyrimidin-7-ylsulphanylmethyl)-3-0-tolyl-3H-quinazolin-4-one; 5-methyl-2-(2-methylsulphanyl-9H-purin-6-ylsulphanylmethyl)-3-o-tolyl-3H-quinazolin-4-one; 2-(2-hydroxy-9H-purin-6-ylsulphanylmethyl)-5-methyl-3-o-tolyl-3H-quinazolin-4-one; 5-methyl-2-(1-methyl-1H-imidazol-2-ylsulphanylmethyl)-3-o-tolyl-3H-quinazolin-4-one; 5-methyl-3-0-tolyl-2-(H-[1,2,4]triazol-3-ylsulphanylmethyl)-3H-quinazolin-4-one; 2-(2-amino-chloro-purin-9-ylmethyl)-5-methyl-3-o-tolyl-3H-quinazolin-4-one; 2-(6-aminopurin-7-ylmethyl)-5-methyl-3-o-tolyl-3H-quinazolin-4-one; 2-(7-amino-1,2,3-triazolo[4,5-d]pyrimidin-3-yl-methyl)-5-methyl-3-o-tolyl-3H-quinazolin-4-one; 2-(7-amino-1,2,3-triazolo[4,5-d]pyrimidin-1-yl-methyl)-5-methyl-3-o-tolyl-3H-quinazolin-4-one; 2-(6-amino-9H-purin-2-ylsulphanylmethyl)-5-methyl-3-o-tolyl-3H-quinazolin-4-one; 2-(2-amino-6-ethylamino-pyrimidin-4-ylsulphanylmethyl)-5-methyl-3-o-tolyl-3H-quinazolin-4-one; 2-(3-amino-5-methylsulphanyl-1,2,4-triazol-1-yl-methyl)-5-methyl-3-o-tolyl-3H-quinazolin-4-one; 2-(5-amino-3-methylsulphanyl-1,2,4-triazol-1-ylmethyl)-5-methyl-3-o-tolyl-3H-quinazolin-4-one; 5-methyl-2-(6-methylaminopurin-9-ylmethyl)-3-o-tolyl-3H-quinazolin-4-one; 2-(6-benzylaminopurin-9-ylmethyl)-5-methyl-3-o-tolyl-3H-quinazolin-4-one; 2-(2,6-diaminopurin-9-ylmethyl)-5-methyl-3-o-tolyl-3H-quinazolin-4-one; 5-methyl-2-(9H-purin-6-ylsulphanylmethyl)-3-o-tolyl-3H-quinazolin-4-one; 3-isobutyl-5-methyl-2-(9H-purin-6-ylsulphanylmethyl)-3H-quinazolin-4-one; N-{2-[5-methyl-4-oxo-2-(9H-purin-6-ylsulphanylmethyl)-4H-quinazolin-3-yl]-phenyl}-acetamide; 5-methyl-3-(E-2-methyl-cyclohexyl)-2-(9H-purin-6-ylsulphanylmethyl)-3H-quinazolin-4-one; 2-[5-methyl-4-oxo-2-(9H-purin-6-ylsulphanylmethyl)-4H-quinazolin-3-yl]-benzoic acid; 3-{2-[(2-dimethylaminoethyl)methylamino]phenyl}-5-methyl-2-(9H-purin-6-ylsulphanylmethyl)-3H-quin-azolin-4-one; 3-(2-chlorophenyl)-5-methoxy-2-(9H-purin-6-ylsulphanylmethyl)-3H-quinazolin-4-one; 3-(2-chlorophenyl)-5-(2-morpholin-4-yl-ethylamino)-2-(9H-purin-6-ylsulphanylmethyl)-3H-quinazolin-4-one; 3-benzyl-5-methoxy-2-(9H-purin-6-ylsulphanylmethyl)-3H-quinazolin-4-one; 2-(6-aminopurin-9-ylmethyl)-3-(2-benzyloxyphenyl)-5-methyl-3H-quinazolin-4-one; 2-(6-aminopurin-9-ylmethyl)-3-(2-hydroxyphenyl)-5-methyl-3H-quinazolin-4-one; 2-(1-(2-amino-9H-purin-6-ylamino)ethyl)-5-methyl-3-o-tolyl-3H-quinazolin-4-one; 5-methyl-2-[1-(9H-purin-6-ylamino)propyl]-3-o-tolyl-3H-quinazolin-4-one; 2-(1-(2-fluoro-9H-purin-6-ylamino)propyl)-5-methyl-3-o-tolyl-3H-quinazolin-4-one; 2-(1-(2-amino-9H-purin-6-ylamino)propyl)-5-methyl-3-o-tolyl-3H-quinazolin-4-one; 2-(2-benzyloxy-1-(9H-purin-6-ylamino)ethyl)-5-methyl-3-o-tolyl-3H-quinazolin-4-one; 2-(6-aminopurin-9-ylmethyl)-5-methyl-3-{2-(2-(1-methylpyrrolidin-2-yl)-ethoxy)-phenyl}-3H-quinazolin-4-one; 2-(6-aminopurin-9-ylmethyl)-3-(2-(3-dimethylamino-propoxy)-phenyl)-5-methyl-3H-quinazolin-4-one; 2-(6-aminopurin-9-ylmethyl)-5-methyl-3-(2-prop-2-ynyloxyphenyl)-3H-quinazolin-4-one; 2-(2-(1-(6-aminopurin-9-ylmethyl)-5-methyl-4-oxo-4H-quinazolin-3-yl]-phenoxy}-acetamide; 5-chloro-3-(3,5-difluoro-phenyl)-2-[1-(9H-purin-6-ylamino)-propyl]-3H-quinazolin-4-one; 3-phenyl-2-[1-(9H-purin-6-ylamino)-propyl]-3H-quinazolin-4-one; 5-fluoro-3-phenyl-2-[1-(9H-purin-6-ylamino)-propyl]-3H-quinazolin-4-one; 3-(2,6-difluoro-phenyl)-5-methyl-2-[1-(9H-purin-6-ylamino)-propyl]-3H-quinazolin-4-one; 6-fluoro-3-phenyl-2-[1-(9H-purin-6-ylamino)-ethyl]-3H-quinazolin-4-one; 3-(3,5-difluoro-phenyl)-5-methyl-2-[1-(9H-purin-6-ylamino)-ethyl]-3H-quinazolin-4-one; 5-fluoro-3-phenyl-2-[1-(9H-purin-6-ylamino)-ethyl]-3H-quinazolin-4-one; 3-(2.3-difluoro-phenyl)-5-methyl-2-[1-(9H-purin-6-ylamino)-ethyl]-3H-quinazolin-4-one; 5-methyl-3-phenyl-2-[1-(9H-purin-6-ylamino)-ethyl]-3H-quinazolin-4-one; 3-(3-chloro-phenyl)-5-methyl-2-[1-(9H-purin-6-ylamino)-ethyl]-3H-quinazolin-4-one; 5-methyl-3-phenyl-2-[(9H-purin-6-ylamino)-methyl]-3H-quinazolin-4-one; 2-[(2-amino-9H-purin-6-ylamino)-methyl]-3-(3,5-difluoro-phenyl)-5-methyl-3H-quinazolin-4-one; 3-{2-[(2]-diethylamino-ethyl)-methyl-amino]-phenyl)-5-methyl-2-[(9H-purin-6-ylamino)-methyl]-3H-quinazolin-4-one; 5-chloro-3-(2-fluoro-phenyl)-2-[(9H-purin-6-ylamino)-methyl]-3H-quinazolin-4-one; 5-chloro-2-[(9H-purin-6-ylamino)-methyl]-3-o-tolyl-3H-quinazolin-4-one; 5-chloro-3-(2-chloro-phenyl)-2-[(9H-purin-6-ylamino)-methyl]-3H-quinazolin-4-one; 6-fluoro-3-(3-fluoro-phenyl)-2-[1-(9H-purin-6-ylamino)-ethyl]-3H-quinazolin-4-one; 2-[1-(2-amino-9H-purin-6-ylamino)-ethyl]-5-chloro-3-(3-fluorophenyl)-3H-quinazolin-4-one; and the pharmaceutically acceptable salts and solvates thereof.

Formulations

The compounds according to the invention may be administered by oral, transdermal, inhalative, parenteral or sublingual route. The compounds according to the invention are present as active ingredients in conventional preparations, for example in compositions consisting essentially of an inert pharmaceutical carrier and an effective dose of the active substance, such as for example tablets, coated tablets, capsules, lozenges, powders, solutions, suspensions, emulsions, syrups, suppositories, transdermal systems etc. An effective dose of the compounds according to the invention is between 0.1 and 5000, preferably between 1 and 500, more preferably between 5-300 mg/dose for oral administration, and between 0.001 and 50, preferably between 0.1 and 10 mg/dose for intravenous. subcutaneous or intramuscular administration. Examples of inhalable formulations include inhalable powders, propellant-containing metered-dose aerosols or propellant-free inhalable solutions. Within the scope of the present invention the term propellant-free inhalable solutions also includes concentrates or sterile ready-to-use inhalable solutions. For use by inhalation it is preferable to use powders, ethanolic or aqueous solutions. For inhalation, according to the invention, solutions containing 0.01 to 1.0, preferably 0.1 to 0.5% active substance are suitable. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable formulations include, for example, tablets, capsules, suppositories, solutions, syrups, emulsions or dispersible powders. Corresponding tablets may be obtained for example by mixing the active substance(s) with known excipients, for example inert diluents, such as calcium carbonate, calcium phosphate or lactose, disintegrants such as maize starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

The inhalable powders which may be used according to the invention may contain the active substance according to the invention either on its own or in admixture with suitable physiologically acceptable excipients.

If the active substances according to the invention are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 and 150 μm, most preferably between 15 and 80 μm. In some cases it may seem appropriate to add finer excipient fractions with an average particle size of 1 to 9 μm to the excipient mentioned above. These finer excipients are also selected from the group of possible excipients listed hereinbefore. Finally, in order to prepare the inhalable powders according to the invention, micronised active substances according to the invention, preferably with an average particle size of 0.5 to 10 μm, more preferably from 1 to 5 μm, are added to the excipient mixture. Processes for producing the inhalable powders according to the invention by grinding and micronising and finally mixing the ingredients together are known from the prior art.

The inhalable powders according to the invention may be administered using inhalers known from the prior art.

Inhalation aerosols containing propellant gas according to the invention may contain active substances according to the invention dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The above-mentioned propellant gases may be used on their own or in admixture. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances according to the invention may be administered in the form of propellant-free inhalable solutions and suspensions. The solvent used may be an aqueous or alcoholic, preferably an ethanolic solution. The solvent may be water on its own or a mixture of water and ethanol.

The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing the active substance according to the invention are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

The addition of editic acid (EDTA) or one of the known salts thereof, sodium edetate, as stabiliser or complexing agent may optionally be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance according to the invention, only benzalkonium chloride and sodium edetate. In another preferred embodiment, no sodium edetate is present.

A therapeutically effective daily dose is between 1 and 2000 mg, preferably 10-500 mg per adult.

The Examples which follow illustrate the present invention without restricting its scope:

Examples of Pharmaceutical Formulations

| A) Tablets | per tablet |
|---|---|
| active substance | 100 mg |
| lactose | 140 mg |
| maize starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, granulated while wet and dried. The granulate, the rest of the corn starch and the magnesium stearate are screened and mixed together. The mixture is compressed to form tablets of a suitable shape and size.

| B) Tablets | per tablet |
|---|---|
| active substance | 80 mg |
| corn starch | 190 mg |
| lactose | 55 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) Coated tablets | per coated tablet |
|---|---|
| Active substance | 5 mg |
| Corn starch | 41.5 mg |
| Lactose | 30 mg |
| Polyvinylpyrrolidone | 3 mg |
| Magnesium stearate | 0.5 mg |
| | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in a known manner with a covering consisting essentially of sugar and talc. The finished coated tablets are polished with wax

| D) Capsules | per capsule |
|---|---|
| Active substance | 50 mg |
| Corn starch | 268.5 mg |
| Magnesium stearate | 1.5 mg |
| | 320 mg |

The substance and corn starch are mixed and moistened with water. The moist mass is screened and dried. The dry granules are screened and mixed with magnesium stearate. The finished mixture is packed into size 1 hard gelatine capsules.

| E) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) Suppositories | |
|---|---|
| Active substance | 50 mg |
| Solid fat | 1650 mg |
| | 1700 mg |

The hard fat is melted. At 40° C. the ground active substance is homogeneously dispersed. It is cooled to 38° C. and poured into slightly chilled suppository moulds.

| G) Oral suspension | |
|---|---|
| active substance | 50 mg |
| hydroxyethylcellulose | 50 mg |
| sorbic acid | 5 mg |
| sorbitol (70%) | 600 mg |
| glycerol | 200 mg |
| flavouring | 15 mg |
| water ad | 5 ml |

Distilled water is heated to 70° C. Hydroxyethyl-cellulose is dissolved therein with stirring. After the addition of sorbitol solution and glycerol the mixture is cooled to ambient temperature. At ambient temperature, sorbic acid, flavouring and substance are added. To eliminate air from the suspension it is evacuated with stirring.

and 50 mg of active substance.

| H) Metered-dose aerosol (suspension) | |
|---|---|
| active substance | 0.3 wt. % |
| sorbitolan trioleate | 0.6 wt. % |
| HFA134A:HFA227 2:1 | 99.1 wt. % |

The suspension is transferred into a conventional aerosol container with a metering valve. Preferably, 50 µl of suspension are delivered per spray. The active substance may also be metered in higher doses if desired.

| I) Metered-dose aerosol (solution) | |
|---|---|
| active substance | 0.3 wt. %. % |
| abs. ethanol | 20 wt. % |
| aqueous HCl 0.01 mol/l | 2.0 wt. % |
| HFA134A | 77.7 wt. % |

The solution is produced in the usual way by mixing the individual ingredients together.

| J) Inhalable powder | |
|---|---|
| active substance | 80 µg |
| lactose monohydrate | ad 10 mg |

The powder for inhalation is produced in the usual way by mixing the individual ingredients together.

The invention claimed is:
1. A compound of the formula (I),

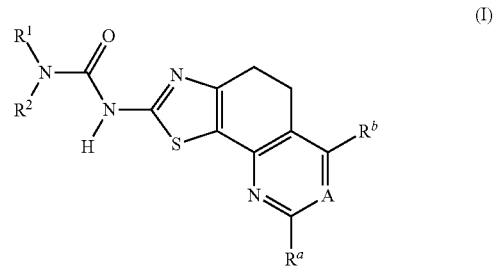

wherein
A denotes N;
$R^a$ denotes hydrogen or an optionally substituted group selected from among $C_1$-$C_8$-alkyl, $C_2$-$C_8$-alkenyl, $C_2$-$C_8$-alkynyl, $C_3$-$C_8$-cycloalkyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_4$-alkyl, spiro, $C_3$-$C_8$-heterocycloalkyl and $C_3$-$C_8$-heterocycloalkyl-$C_1$-$C_4$-alkyl,
$R^b$ denotes hydrogen, OH or $NH_2$
or an optionally substituted group selected from among $C_1$-$C_8$-alkyl, $C_3$-$C_8$-cycloalkyl, $C_2$-$C_8$-alkenyl, $C_2$-$C_8$-alkynyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl- $C_1$-$C_4$-alkyl, spiro, $C_3$-$C_8$-heterocycloalkyl, $CONH_2$, $C_6$-$C_{14}$-aryl-NH, $C_3$-$C_8$-heterocycloalkyl-NH— and O—$C_1$-$C_3$-alkyl, $R^1$ denotes hydrogen or an optionally substituted group selected from among $C_1$-$C_8$-alkyl, $C_3$-$C_8$-cycloalkyl, $C_2$-$C_8$-alkenyl, $C_2$-$C_8$-alkynyl and $C_6$-$C_{14}$-aryl-$C_1$-$C_5$-alkyl-;
or $R^2$ denotes hydrogen or an optionally substituted group selected from among $C_1$-$C_8$-alkyl, $C_3$-$C_8$-cycloalkyl, $C_2$-$C_8$-alkenyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_6$-alkyl, $C_9$-$C_{13}$-spiro, $C_3$-$C_8$-heterocycloalkyl, $C_3$-$C_8$-heterocycloalkyl-$C_1$-$C_6$-alkyl- and $C_6$-$C_{14}$-aryl-$C_1$-$C_6$-alkyl-;
or $R^1$ and $R^2$ together form an optionally substituted five-, six- or seven-membered ring consisting of carbon atoms and optionally 1 to 2 heteroatoms, selected from among oxygen, sulphur and nitrogen;
or $R^1$ and $R^2$ together form an optionally substituted nine- to thirteen-membered spirocyclic ring,
or $R^2$ denotes a group selected from among general formulae (A1) to (A18)

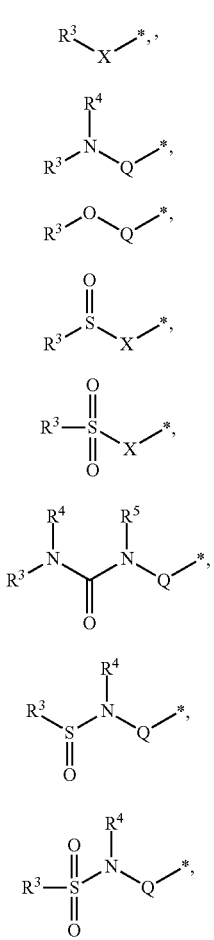
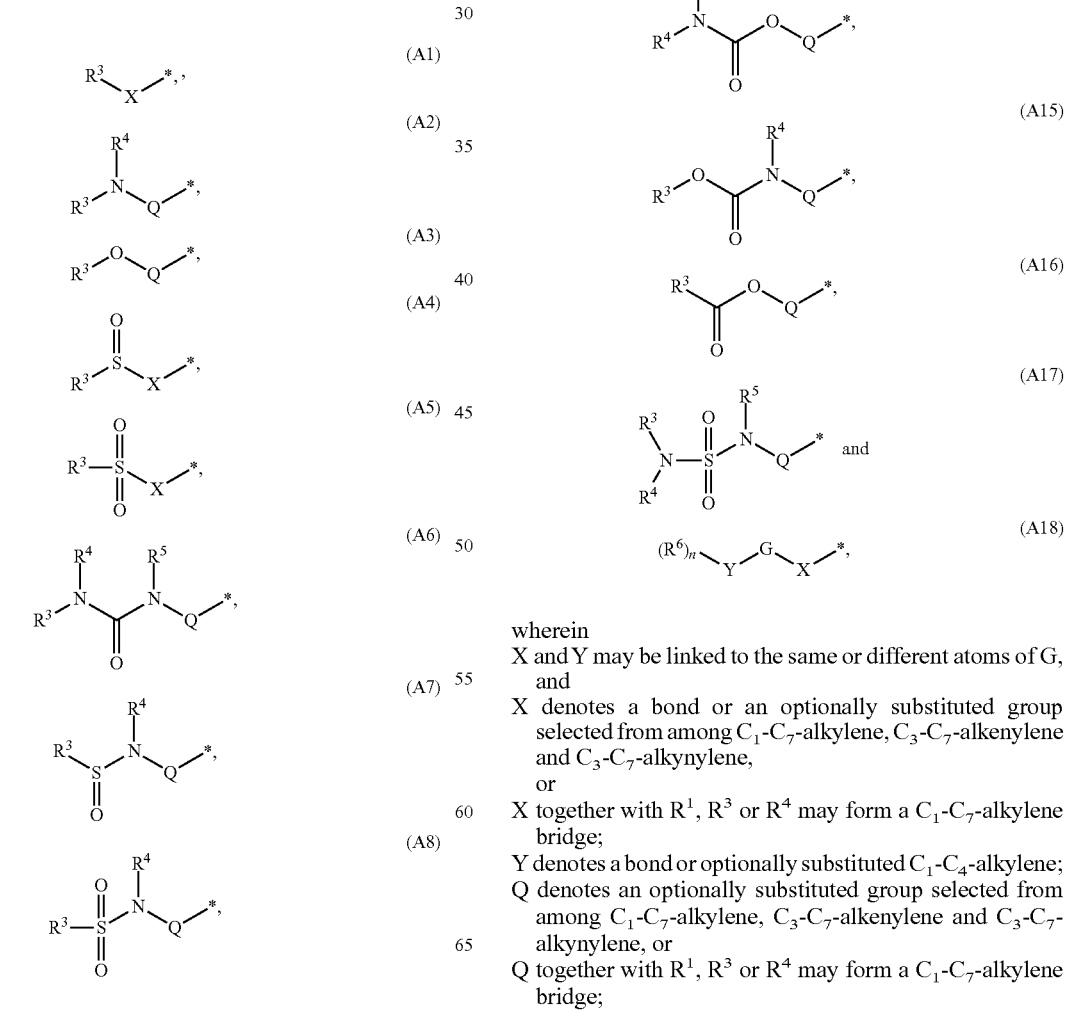

wherein
X and Y may be linked to the same or different atoms of G, and

X denotes a bond or an optionally substituted group selected from among $C_1$-$C_7$-alkylene, $C_3$-$C_7$-alkenylene and $C_3$-$C_7$-alkynylene,
or X together with $R^1$, $R^3$ or $R^4$ may form a $C_1$-$C_7$-alkylene bridge;

Y denotes a bond or optionally substituted $C_1$-$C_4$-alkylene;

Q denotes an optionally substituted group selected from among $C_1$-$C_7$-alkylene, $C_3$-$C_7$-alkenylene and $C_3$-$C_7$-alkynylene, or Q together with $R^1$, $R^3$ or $R^4$ may form a $C_1$-$C_7$-alkylene bridge;

R³, R⁴, R⁵ which may be identical or different, denote hydrogen or an optionally substituted group selected from among $C_1$-$C_8$-alkyl, $C_3$-$C_8$-cycloalkyl, $C_2$-$C_6$-haloalkyl, $C_1$-$C_4$-alkyl-$C_3$-$C_8$-cycloalkyl, $C_3$-$C_8$-cycloalkyl-$C_1$-$C_4$-alkyl, $NR^7R^8$, $NR^7R^8$—$C_1$-$C_4$-alkyl, $C_1$-$C_4$-alkoxy, $C_1$-$C_4$-alkoxy-$C_1$-$C_4$-alkyl, $C_6$-$C_{14}$-aryl and $C_5$-$C_{10}$-heteroaryl;

or in each case two of the substituents

R³, R⁴, R⁵ together form an optionally substituted five-, six- or seven-membered ring, consisting of carbon atoms and optionally 1-2 heteroatoms, selected from among oxygen, sulphur and nitrogen;

G denotes a saturated, partially saturated or unsaturated ring system consisting of 3-10 C atoms, wherein optionally up to 6 C atoms are replaced by heteroatoms selected from among nitrogen, oxygen and sulphur;

R⁶ which may be identical or different, denote hydrogen or an optionally substituted group selected from among =O, $C_1$-$C_8$-alkyl, $C_2$-$C_6$-alkenyl $C_3$-$C_8$-cycloalkyl, $C_2$-$C_6$-haloalkyl, $C_6$-$C_{14}$-aryl, $C_5$-$C_{10}$-heteroaryl and $C_3$-$C_8$-heterocycloalkyl, or a group selected from among $NR^7R^8$, $OR^7$, —CO—$C_1$-$C_3$-alkyl-$NR^7R^8$, —O—$C_1$-$C_3$-alkyl-$NR^7R^8$, $CONR^7R^8$, $NR^7COR^8$, —CO—$C_1$-$C_3$-alkyl-$NR^7$(CO)$OR^8$, —O(CO)$NR^7R^8$, $NR^7$(CO)$NR^8R^9$, $NR^7$(CO)$OR^8$, (CO)$OR^7$, —O(CO)$R^7$, $COR^7$, (SO)$R^7$, $(SO_2)R^7$, $(SO_2)NR^7R^8$, $NR^7(SO_2)R^8$, $NR^7(SO_2)NR^8R^9$, CN, —$C_1$-$C_3$-alkyl-$C_6$-$C_{14}$-aryl, —NH—CO—NH—$C_1$-$C_3$-alkyl and halogen;

n denotes 1, 2 or 3

R⁷, R⁸, R⁹ which may be identical or different, denote hydrogen or an optionally substituted group selected from among $C_1$-$C_8$-alkyl, $C_3$-$C_8$-cycloalkyl, $C_1$-$C_6$-haloalkyl, $C_1$-$C_4$-alkyl-$C_3$-$C_8$-cycloalkyl, $C_3$-$C_8$-cycloalkyl-$C_1$-$C_3$-alkyl, $C_6$-$C_{14}$-aryl, $C_1$-$C_4$-alkyl-$C_6$-$C_{14}$-aryl, $C_6$-$C_{14}$-aryl-$C_1$-$C_4$-alkyl, $C_3$-$C_8$-heterocycloalkyl, $C_1$-$C_5$-alkyl-$C_3$-$C_8$-heterocycloalkyl, $C_3$-$C_8$-heterocycloalkyl-$C_1$-$C_4$-alkyl, $C_1$-$C_4$-alkyl (CO)— and $C_1$-$C_4$-alkyl-O(CO)—;

or in each case two of the substituents

R⁷, R⁸, R⁹ together form an optionally substituted five-, six- or seven-membered ring, consisting of carbon atoms and optionally 1-2 heteroatoms, selected from among oxygen, sulphur and nitrogen;

optionally in the form of the tautomers, the racemates, the enantiomers, the diastereomers and the mixtures thereof, as well as optionally the pharmacologically acceptable acid addition salts thereof, with the proviso that the following compounds are excluded:
a) 8-phenyl-4,5-dihydro-thiazolo[4,5-h]quinazolin-2-yl)-urea
b) 1-methyl-3-(8-phenyl-4,5-dihydro-thiazolo[4,5-h]quinazolin-2-yl)-urea
c) 1,1-dimethyl-3-(8-phenyl-4,5-dihydro-thiazolo[4,5-h]quinazolin-2-yl)-urea
d) 1-(2-dimethylamino-ethyl)-3-(8-phenyl-4,5-dihydro-thiazolo[4,5-h]quinazolin-2-yl)-urea
e) 4-methyl-piperazine-1-carboxylic acid (8-phenyl-4,5-dihydro-thiazolo[4,5-h]quinazolin-2-yl)-amide
f) piperidine-1-carboxylic acid (8-phenyl-4,5-dihydro-thiazolo[4,5-h]quinazolin-2-yl)-amide
g) pyrrolidine-1-carboxylic acid (8-phenyl-4,5-dihydro-thiazolo[4,5-h]quinazolin-2-yl)-amide
h) 1-methyl-3-(8-o-tolyl-4,5-dihydro-thiazolo[4,5-h]quinazolin-2-yl)-urea
i) (8-o-tolyl-4,5-dihydro-thiazolo[4,5-h]quinazolin-2-yl)-urea
j) 1,1-dimethyl-3-(8-o-tolyl-4,5-dihydro-thiazolo[4,5-h]quinazolin-2-yl)-urea and
k) [8-(2-methoxy-phenyl)-4,5-dihydro-thiazolo[4,5-h]quinazolin-2-yl]-urea and
l) morpholine-4-carboxylic acid (8-phenyl-4,5-dihydro-thiazolo[4,5-h]quinazolin-2-yl)-amide.

2. The compound according to claim 1, wherein

X, Y, Q and G may have the meaning specified and $R^a$ denotes hydrogen or a group selected from among $C_1$-$C_8$-alkyl, $C_2$-$C_8$-alkenyl, $C_2$-$C_8$-alkynyl, $C_3$-$C_8$-cycloalkyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_4$-alkyl, spiro, $C_3$-$C_8$-heterocycloalkyl and $C_3$-$C_8$-heterocycloalkyl-$C_1$-$C_4$-alkyl, which may optionally be substituted by one or more of the groups, which may be identical or different, selected from among $C_1$-$C_6$-alkyl, $C_2$-$C_6$-alkenyl, $C_2$-$C_6$-alkynyl, $C_2$-$C_6$-alkynyl-$NR^5R^6$, $C_3$-$C_8$-cycloalkyl, $C_1$-$C_6$-haloalkyl, halogen, OH, $C_1$-$C_4$-alkoxy, CN, $NO_2$, $NR^{10}R^{11}$, $OR^{10}$, $COR^{10}$, $COOR^{10}$, $CONR^{10}R^{11}$, $NR^{10}COR^{11}$, $NR^{10}$(CO)$NR^{11}R^{12}$, O(CO)$NR^{10}R^{11}$, $NR^{10}$(CO)$OR^{11}$, $SO_2R^{10}$, $SOR^{10}$, $SO_2NR^{10}R^{11}$, $NR^{10}SO_2NR^{11}R^{12}$ and $NR^{10}SO_2R^{11}$;

or $R^a$ is optionally substituted by a group of general formula (B)

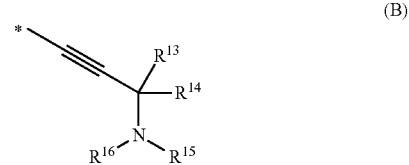

(B)

wherein,

R¹³ to R¹⁶ which may be identical or different, represent hydrogen or $C_1$-$C_6$-alkyl, or two of the substituents R¹³ to R¹⁶ together form an optionally substituted five-, six- or seven-membered ring, consisting of carbon atoms and optionally 1-2 heteroatoms, selected from among oxygen, sulphur and nitrogen;

R¹⁰, R¹¹, R¹² which may be identical or different, denote hydrogen or a group selected from among $C_1$-$C_6$-alkyl, $C_2$-$C_6$-alkenyl, $C_2$-$C_6$-alkynyl, $C_3$-$C_8$-cycloalkyl and $C_1$-$C_6$ haloalkyl;

or in each case two of the groups

R¹⁰, R¹¹, R¹² together form a five-, six- or seven-membered ring, consisting of carbon atoms and optionally 1-2 heteroatoms, selected from among oxygen, sulphur and nitrogen;

$R^b$ denotes hydrogen, OH or $NH_2$ or an optionally substituted group selected from among $C_1$-$C_8$-alkyl, $C_3$-$C_8$-cycloalkyl, $C_2$-$C_8$-alkenyl, $C_2$-$C_8$-alkynyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl- $C_1$-$C_4$-alkyl, spiro, $C_3$-$C_8$-heterocycloalkyl, $CONH_2$, $C_6$-$C_{14}$-aryl-NH, $C_3$-$C_8$-heterocycloalkyl-NH— and O—$C_1$-$C_3$-alkyl, which may optionally be substituted by one or more of the groups, which may be identical or different, selected from among $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, halogen, OH, OMe, CN, $NH_2$, NHMe and $NMe_2$;

$R^1$ denotes hydrogen or a group selected from among $C_1$-$C_8$-alkyl, $C_3$-$C_8$-cycloalkyl, $C_2$-$C_8$-alkenyl, $C_2$-$C_8$-alkynyl and $C_6$-$C_{14}$-aryl-$C_1$-$C_5$-alkyl, which may optionally be substituted by one or more of the groups, which may be identical or different, selected from among halogen, COOH, $NH_2$, OH, CN, $C_1$-$C_6$-alkyl, OMe, —NH(CO)-alkyl and —(CO)O-alkyl, $R^2$ denotes hydrogen or a group selected from among $C_1$-$C_8$ alkyl, $C_3$-$C_8$-cycloalkyl, $C_2$-$C_8$-alkenyl, $C_3$-$C_8$-cycloalkenyl, $C_1$-$C_6$-haloalkyl, $C_6$-$C_{14}$-aryl, $C_6$-$C_{14}$-aryl-$C_1$-$C_5$-alkyl, $C_5$-$C_{10}$-heteroaryl, $C_3$-$C_8$-cycloalkyl-$C_1$-$C_4$-alkyl, $C_3$-$C_8$-cycloalkenyl-$C_1$-$C_4$-alkyl, $C_5$-$C_{10}$-heteroaryl-$C_1$-$C_6$-alkyl, $C_9$-$C_{13}$-spiro, $C_3$-$C_8$-heterocycloalkyl, $C_3$-$C_8$-heterocycloalkyl-$C_1$-$C_6$-alkyl- and $C_6$-$C_{14}$-aryl-$C_1$-$C_6$-alkyl, which may optionally be substituted by one or more of the groups, which may be identical or different, selected from among halogen, $NH_2$, OH, CN, $C_1$-$C_6$-alkyl, OMe, —NH(CO)-alkyl, =O, COOH and —(CO)O-alkyl, or $R^1$ and $R^2$ together form a five-, six- or seven-membered ring consisting of carbon atoms and optionally 1 to 2 heteroatoms, selected from among oxygen, sulphur and nitrogen, which may optionally be substituted by one or more of the groups, which may be identical or different, selected from among halogen, $NH_2$, OH, CN, $C_1$-$C_6$-alkyl, OMe, —NH(CO)—$C_1$-$C_4$-alkyl, and —(CO)O—$C_1$-$C_4$-alkyl, or $R^1$ and $R^2$ together form an optionally substituted nine- to thirteen-membered spirocyclic ring, or $R^2$ denotes a group selected from among general formulae (A1) to (A18)

(A1)

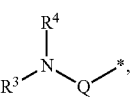
(A2)

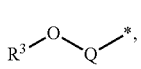
(A3)

(A4)

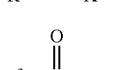
(A5)

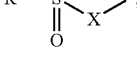

-continued

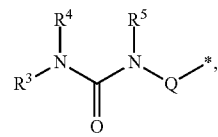
(A6)

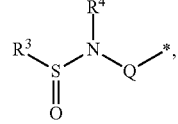
(A7)

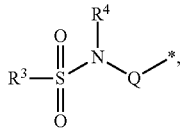
(A8)

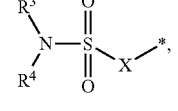
(A9)

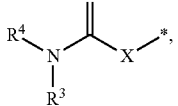
(A10)

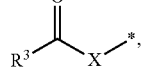
(A11)

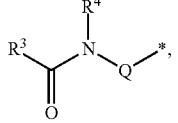
(A12)

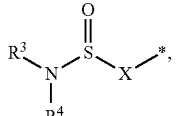
(A13)

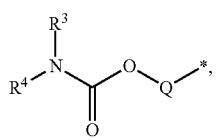
(A14)

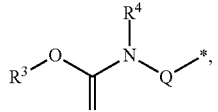
(A15)

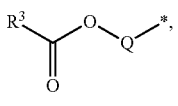
(A16)

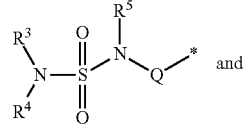
(A17)

and

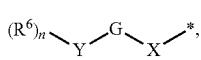
(A18)

wherein $R^3$, $R^4$, $R^5$ which may be identical or different, denote hydrogen or a group selected from among $C_1$-$C_8$-alkyl, $C_3$-$C_8$-cycloalkyl, $C_2$-$C_6$-haloalkyl, $C_1$-$C_4$-alkyl-$C_3$-$C_8$-cycloalkyl, $C_3$-$C_8$-cycloalkyl-$C_1$-$C_4$-alkyl, $NR^7R^8$, $NR^7R^8$—$C_1$-$C_4$-alkyl, $C_1$-$C_4$-alkoxy, $C_1$-$C_4$-alkoxy-$C_1$-$C_4$-alkyl, $C_6$-$C_{14}$-aryl and $C_5$-$C_{10}$-heteroaryl, which may optionally be substituted by one or more of the groups, which may be identical or different, selected from among halogen, $NH_2$, OH, CN, $NR^9R^{10}$, —NH(CO)—$C_1$-$C_4$-alkyl and MeO, or in each case two of the substituents $R^3$, $R^4$, $R^5$ together form a five-, six- or seven-membered ring, consisting of carbon atoms and optionally 1-2 heteroatoms, selected from among oxygen, sulphur and nitrogen; which may optionally be substituted by one or more of the groups, which may be identical or different, selected from among halogen, $NH_2$, OH, CN, $NR^9R^{10}$, —NH(CO)—$C_1$-$C_4$-alkyl and MeO, $R^6$ which may be identical or different, denote hydrogen or a group, selected from among $C_1$-$C_8$-alkyl, $C_2$-$C_6$-alkenyl $C_3$-$C_8$-cycloalkyl, $C_2$-$C_6$-haloalkyl, $C_6$-$C_{14}$-aryl, $C_5$-$C_{10}$-heteroaryl and $C_3$-$C_8$-heterocycloalkyl, which may optionally be substituted by one or more of the groups, which may be identical or different, selected from among $NH_2$, NHMe, $NMe_2$, OH, OMe, CN, —$C_1$-$C_3$-alkyl-$C_6$-$C_{14}$-aryl, —NH—CO—NH—$C_1$-$C_3$-alkyl, $C_1$-$C_6$-alkyl and —(CO)O—$C_1$-$C_6$-alkyl or a group selected from among =O, $NR^7R^8$, $OR^7$, —CO—$C_1$-$C_3$-alkyl-$NR^7R^8$, —O—$C_1$-$C_3$-alkyl-$NR^7R^8$, $CONR^7R^8$, $NR^7COR^8$, —CO—$C_1$-$C_3$-alkyl-$NR^7(CO)OR^8$, —O(CO)$NR^7R^8$, $NR^7(CO)NR^8R^9$, $NR^7(CO)OR^8$,(CO)$OR^7$, —O(CO)$R^7$, $COR^7$, (SO)$R^7$, $(SO_2)R^7$, $(SO_2)NR^7R^8$, $NR^7(SO_2)R^8$, $NR^7(SO_2)NR^8R^9$, CN and halogen;

n denotes 1, 2 or 3

$R^7$, $R^8$, $R^9$ which may be identical or different, denote hydrogen or a group selected from among $C_1$-$C_8$-alkyl, $C_3$-$C_8$-cycloalkyl, $C_2$-$C_6$-haloalkyl, $C_1$-$C_4$-alkyl-$C_3$-$C_8$-cycloalkyl, $C_3$-$C_8$-cycloalkyl-$C_1$-$C_3$-alkyl, $C_6$-$C_{14}$-aryl, $C_1$-$C_4$-alkyl-$C_6$-$C_{14}$-aryl, $C_6$-$C_{14}$-aryl-$C_1$-$C_4$-alkyl, $C_3$-$C_8$-heterocycloalkyl, $C_1$-$C_5$-alkyl-$C_3$-$C_8$-heterocycloalkyl, $C_3$-$C_8$-heterocycloalkyl-$C_1$-$C_4$-alkyl, $C_1$-$C_4$-alkyl(CO)— and $C_1$-$C_4$-alkyl-O(CO), which may optionally be substituted by one or more of the groups, which may be identical or different, selected from among halogen, $NH_2$, OH, CN, OMe, NHMe, $NMe_2$, $C_1$-$C_6$-alkyl and (CO)O$C_1$-$C_6$-alkyl, or in each case two of the substituents $R^7$, $R^8$, $R^9$ together form a five-, six- or seven-membered ring, consisting of carbon atoms and optionally 1-2 heteroatoms, selected from among oxygen, sulphur and nitrogen; which may optionally be substituted by one or more of the groups, which may be identical or different, selected from among halogen, $NH_2$, OH, CN, OMe, NHMe, $NMe_2$, $C_1$-$C_6$-alkyl and (CO)O$C_1$-$C_6$-alkyl.

3. The compound according to claim 2, wherein

A, $R^a$ and $R^1$ to $R^{16}$ may have the meaning specified and $R^b$ denotes hydrogen.

4. The compound according to claim 2, wherein

A, $R^1$ to $R^{16}$ may have the meaning specified, $R^a$ denotes $C_6$-$C_{14}$-aryl or $C_1$-$C_6$-alkyl wherein $R^a$ may optionally be substituted by one or more of the groups, which may be identical or different, selected from among $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, halogen, OH, $C_1$-$C_4$-alkoxy, CN, $NO_2$, $NR^{10}R^{11}$, $OR^{10}$, $COR^{10}$, $COOR^{10}$, $CONR^{10}R^{11}$, $NR^{10}COR^{11}$, $NR^{10}(CO)NR^{11}R^{12}$, $O(CO)NR^{10}R^{11}$, $NR^{10}(CO)OR^{11}$, $SO_2R^{10}$, $SOR^{10}$, $SO_2NR^{10}R^{11}$, $NR^{10}SO_2NR^{11}R^{12}$ and $NR^{10}SO_2R^{11}$; and $R^b$ denotes hydrogen.

5. The compound according to claim 4, wherein

A, $R^a$ and $R^b$ may have the meaning specified and $R^1$ denotes hydrogen, $C_1$-$C_5$-alkyl or $C_3$-$C_8$-cycloalkyl, $R^2$ denotes hydrogen, $C_1$-$C_5$-alkyl or $C_3$-$C_8$-cycloalkyl, phenyl or $R^1$ and $R^2$ together form an optionally substituted five- or six-membered ring consisting of carbon atoms and optionally 1 to 2 nitrogen atoms, or $R^1$ and $R^2$ together form an optionally substituted nine- to thirteen-membered spirocyclic ring, or $R^1$, $R^2$ which may be identical or different, denote a group selected from among general formulae (A1)-A(17), wherein X denotes a bond or an optionally substituted $C_1$-$C_3$-alkylene, or X together with $R^1$, $R^3$ or $R^4$ may form a 5- or 6-membered heterocyclic group;

Q denotes an optionally substituted $C_1$-$C_3$-alkylene,

Q together with $R^1$, $R^3$ or $R^4$ may form a $C_1$-$C_7$-alkylene bridge;

$R^3$, $R^4$, $R^5$ which may be identical or different, denote hydrogen or an optionally substituted group selected from among $C_1$-$C_4$-alkyl, $C_1$-$C_4$-alkoxy, $C_3$-$C_6$-cycloalkyl, $C_3$-$C_8$-heterocycloalkyl, —$C_1$-$C_3$-alkyl-$C_3$-$C_6$-cycloalkyl, phenyl and $C_5$-$C_{10}$-heteroaryl or in each case two of the substituents $R^3$, $R^4$, $R^5$ together form an optionally substituted five- or six-membered ring, consisting of carbon atoms and optionally 1-2 heteroatoms, selected from among oxygen and nitrogen.

6. The compound according to claim 4, wherein

A, $R^a$ and $R^b$ may have the meaning specified and $R^1$ denotes H, Me $R^2$ denotes hydrogen or a group of general formulae (A18), wherein X denotes a bond or an optionally substituted group selected from among $C_1$-$C_7$alkylene, $C_3$-$C_7$-alkenylene and $C_3$-$C_7$-alkynylene, or X together with $R^1$ may form a C1-7 alkylene bridge Y denotes a bond or methylene, ethylene;

X and Y may be linked to the same or different atoms of G, and

G denotes a saturated, partially saturated or unsaturated ring system consisting of 3-10 C atoms, wherein optionally up to 6 C atoms are replaced by heteroatoms selected from among nitrogen, oxygen and sulphur;

$R^6$ which may be identical or different, denote hydrogen or an optionally substituted group selected from among =O, $C_1$-$C_4$-alkyl, $C_2$-$C_6$-alkenyl, $C_3$-$C_6$-cycloalkyl, $C_6$-$C_{14}$-aryl, $C_5$-$C_6$-heterocycloalkyl, and $C_5$-$C_6$-heteroaryl or a group selected from among $NR^7R^8$, $OR^7$, —O—$C_1$-$C_3$-alkyl-$NR^7R^8$, $CONR^7R^8$, CO—$C_1$-$C_3$-alkyl-$NR^7R^8$, $NR^7COR^8$, $NR^7(CO)OR^8$, —CO—$C_1$-$C_3$-alkyl-$NR^7(CO)OR^8$, $NR^7(CO)NR^8R^9$, $NR^7(CO)OR^8$, $(CO)OR^7$, $COR^7$, $(SO_2)R^7$, —$C_1$-$C_3$-alkyl-$C_6$-$C_{14}$-aryl, —NH—CO—NH—$C_1$-$C_3$-alkyl and CN n denotes 1 or 2

$R^7$, $R^8$, $R^9$ which may be identical or different, denote hydrogen or an optionally substituted group selected from among $C_1$-$C_5$-alkyl, $C_1$-$C_4$-alkyl-$C_6$-$C_{14}$-aryl, $C_3$-$C_6$-heterocycloalkyl, $C_1$-$C_5$-alkyl-$C_3$-$C_8$-heterocycloalkyl- and $C_3$-$C_6$-cycloalkyl, or in each case two of the substituents $R^7$, $R^8$, $R^9$ together form an optionally substituted five- or six-membered ring, consisting of carbon atoms and optionally 1-2 heteroatoms, selected from among oxygen and nitrogen.

7. A pharmaceutical composition comprising a pharmaceutically effective amount of a compound according to claim 1.

8. The pharmaceutical composition according to claim 7, comprising as a further active substance, one or more compounds which are selected from the categories of the betamimetics, anticholinergics, corticosteroids, other PDE4-inhibitors, LTD4-antagonists, EGFR-inhibitors, dopamine angonists, H1-antihistamines, PAF-antagonists and PI3-kinase inhibitors or double or triple combinations thereof.

* * * * *